US009457033B2

(12) United States Patent
Malouin et al.

(10) Patent No.: US 9,457,033 B2
(45) Date of Patent: Oct. 4, 2016

(54) STEROID ALKALOIDS AND USES THEREOF AS ANTIMICROBIAL AGENTS AGAINST ELECTRON TRANSPORT-DEFICIENT MICROBES AND AS POTENTIATORS FOR ANTIMICROBIAL AGENTS AGAINST PATHOGENIC BACTERIA

(75) Inventors: François Malouin, Eastman (CA); Gabriel Mitchell, Shawinigan-Sud (CA); Kamal Bouarab, Sherbrooke (CA); Eric Marsault, Sherbrooke (CA); Felix Chagnon, Waterloo (CA); Simon Boulanger, Sherbrooke (CA); Isabelle Guay, Magog (CA)

(73) Assignee: SOCPRA SCIENCES ET GENIE, S.E.C., Sherbrooke (CA)

( * ) Notice: Subject to any disclaimer, the term of this patent is extended or adjusted under 35 U.S.C. 154(b) by 0 days.

(21) Appl. No.: 13/984,991

(22) PCT Filed: Feb. 15, 2012

(86) PCT No.: PCT/CA2012/050087
§ 371 (c)(1),
(2), (4) Date: Oct. 4, 2013

(87) PCT Pub. No.: WO2012/109752
PCT Pub. Date: Aug. 23, 2012

(65) Prior Publication Data
US 2014/0018312 A1 Jan. 16, 2014

Related U.S. Application Data

(60) Provisional application No. 61/442,948, filed on Feb. 15, 2011.

(51) Int. Cl.
| | |
|---|---|
| *A61K 31/58* | (2006.01) |
| *A01N 45/00* | (2006.01) |
| *A61K 31/7036* | (2006.01) |
| *C07J 43/00* | (2006.01) |
| *A61K 31/395* | (2006.01) |
| *A61L 2/16* | (2006.01) |
| *C07J 7/00* | (2006.01) |
| *C07J 41/00* | (2006.01) |
| *C07J 51/00* | (2006.01) |

(52) U.S. Cl.
CPC .............. *A61K 31/58* (2013.01); *A01N 45/00* (2013.01); *A61K 31/395* (2013.01); *A61K 31/7036* (2013.01); *C07J 43/003* (2013.01); *C07J 43/006* (2013.01); *A61L 2/16* (2013.01); *C07J 7/002* (2013.01); *C07J 7/006* (2013.01); *C07J 7/007* (2013.01); *C07J 7/0085* (2013.01); *C07J 41/005* (2013.01); *C07J 41/0055* (2013.01); *C07J 51/00* (2013.01); *G01N 2800/52* (2013.01)

(58) Field of Classification Search
CPC ............... A61K 31/58; A61K 31/395; A61K 31/7036; C07J 43/006; A01N 45/00
USPC ...................... 514/37, 173, 171, 41; 435/375
See application file for complete search history.

(56) References Cited

U.S. PATENT DOCUMENTS

| | | | |
|---|---|---|---|
| 2,770,618 | A | 11/1956 | Kuhn et al. |
| 3,013,008 | A | 12/1961 | Esters et al. |
| 3,419,661 | A | 12/1968 | Elder et al. |
| 3,515,784 | A | 6/1970 | Wendt et al. |
| 3,558,608 | A | 1/1971 | Klimstra et al. |
| 2003/0216361 | A1 | 11/2003 | Pettit et al. |
| 2009/0074677 | A1 | 3/2009 | Marx et al. |
| 2010/0221245 | A1 | 9/2010 | Kunin |

FOREIGN PATENT DOCUMENTS

| | | |
|---|---|---|
| CA | 2395642 | 7/2001 |
| CN | 101054399 A | 10/2007 |
| CN | 101406564 | 4/2009 |
| CN | 101664555 | 3/2010 |
| FR | 2813019 | 2/2002 |
| FR | 2953138 | 6/2011 |
| WO | 0108670 | 2/2001 |
| WO | 0149279 | 7/2001 |
| WO | 2007025064 | 3/2007 |
| WO | 2009089024 | 7/2009 |
| WO | 2009090063 | 7/2009 |

(Continued)

OTHER PUBLICATIONS

Mates et al., "Membrane potential in anaerobically growing *Staphylococcus aureus* and its relationship to gentamicin uptake. Antimicrob", Agents Chemother., (1983), 23:526-530.

(Continued)

*Primary Examiner* — Kristin Vajda
(74) *Attorney, Agent, or Firm* — Goudreau Gage Dubuc; Julie Gauvreau

(57) ABSTRACT

The present invention includes novel compounds based on the tomatidine skeleton as well as composition comprising these compounds alone and in combination with known compounds, which exhibit antimicrobial activity against extracellular or intracellular electron transport-deficient microbes and/or increase the antimicrobial activity of aminoglycoside antibiotics against their targets, and which are useful as antibacterial agents for treatment or prophylaxis of monomicrobiotic or polymicrobic bacterial infections or for the reduction of antibiotic resistance development in animals or in humans, or for use as antiseptics or agents for sterilization or disinfection.

32 Claims, 11 Drawing Sheets

(56) References Cited

FOREIGN PATENT DOCUMENTS

| WO | 2011067501 | 6/2011 |
| WO | 2011120044 | 9/2011 |

OTHER PUBLICATIONS

Mead et al., "Food-related illness and death in the United States", Emerg Infect Dis, (1999), 5: 607-625.

Melter et al., "Small colony variants of *Staphylococcus aureus*—review", Folia Microbiol (Praha), (2010) ,55: 548-558.

Miller et al., "Single and combination antibiotic therapy of *Staphylococcus aureus* experimental endocarditis: emergence of gentamicin-resistant mutants", Antimicrob Agents Chemother, (1978), 14: 336-343.

Mingyu et al., "Multicolor, One- and Two-Photon Imaging of Enzymatic Activities in Live Cells with Fluorescently Quenched Activity-Based Probes (qABPs)", JACS, (2011), 133(31): 12009-12020.

Mitchell et al., "Tomatidine Inhibits the Replication of *Staphylococcus aureus* Small-Colony Variants in Cystic Fibrosis Airway Epithelial Cells". Antimicrob. Agents Chemother., 2011, 55 :1937-1945.

Mitchell et al., "Tomatidine acts in synergy with aminoglycoside antibiotics against multiresistant *Staphylococcus aureus* and prevents virulence gene expression", J. Antimicrob. Chemother., (2012), 67: 559-568.

Mitchell et al., "Outcome and prevention of *Pseudomonas aeruginosa—Staphylococcus aureus* interactions during pulmonary infections in cystic fibrosis", In Cystic Fibrosis, InTech Open Access Publisher, ISBN 979-953-307-059-8, (2012).

Mitchell et al., "Tomatidine Potentiates the Bactericidal Activity of Aminoglycosides Against Multi-Resistant *Staphylococcus aureus* Strains. Interscience Conference on Antimicrobial Agents and Chemotherapy", Abstr. E-1831, Chicago, Sep. 17-20, 2011.

Mitchell et al., "A role for sigma factor B in the emergence of *Staphylococcus aureus* small-colony variants and elevated biofilm production resulting from an exposure to aminoglycosides", Microb Pathog, (2010a), 48: 18-27.

Mitchell et al., "*Staphylococcus aureus* sigma B-dependent emergence of small-colony variants and biofilm production following exposure to Pseudomonas aeruginosa 4-hydroxy-2-heptylquinoline-N-oxide", (2010b), BMC Microbiol 10: 33.

Mitchell et al., Defects in the cystic fibrosis transmembrane conductance regulator (CFTR) increase *Staphylococcus aureus* intracellular infection of human pulmonary cells. Abstr. 100th Gen. Meet., (2010c), Am. Soc. Microbiol., abstr. D-1179.

Mitchell et al., "Tomatidine (TO) affects virulence regulators of prototypical *Staphylococcus aureus* (SA) and small-colony variants (SCV) of cystic fibrosis patients", Abstr. 49th Intersci. Conf. Antimicrob. Agents Chemother., abstr. C1-1341, (2009).

Moisan et al., "Transcription of virulence factors in *Staphylococcus aureus* small-colony variants isolated from cystic fibrosis patients is influenced by SigB", J Bacteriol (2006), 188: 64-76.

Nagy, E., "Anaerobic infections: update on treatment considerations", Drugs, (2010) 70: 841-858.

Palmer, et al., "Protease-activated receptor regulation of Cl-secretion in Calu-3 cells requires prostaglandin release and CFTR activation", Am J Physiol Cell Physiol, (2006), 290: C1189-1198.

Parkins et al., "Newer antibacterial agents and their potential role in cystic fibrosis pulmonary exacerbation management", J Antimicrob Chemother, (2010), 65: 1853-1861.

Proctor et al., "Small colony variants: a pathogenic form of bacteria that facilitates persistent and recurrent infections", Nat Rev Microbiol, (2006), 4: 295-305.

Pyorala et al., "Coagulase-negative staphylococci-emerging mastitis pathogens", Vet Microbiol, (2009), 134: 3-8.

Qazi et al., "N-acylhomoserine lactones antagonize virulence gene expression and quorum sensing in *Staphylococcus aureus*", Infect Immun, (2006), 74: 910-919.

Ragle et al., "Prevention and treatment of *Staphylococcus aureus* pneumonia with a beta-cyclodextrin derivative", Antimicrob Agents Chemother, (2010), 54, 298-304.

Roddick, J.G., "Steroidal glycoalkaloid alpha-tomatine", Phytochemistry, (1974), 13: 9-25.

Rupnik et al- "Clostridium difficile infection: new developments in epidemiology and pathogenesis", Nat Rev Microbiol, (2009), 7: 526-536.

Sears et al., "Management and treatment of staphylococcal mastitis", Vet Clin North Am Food Anim Pract, (2003), 19: 171-185, vii.

Sendi et al., "*Staphylococcus aureus* as an intracellular pathogen: the role of small colony variants", Trends Microbiol, (2009),17: 54-58.

Shah, P.M. "The need for new therapeutic agents: what is the pipeline?", Clin Microbiol Infect, (2005), 11 Suppl 3: 36-42.

Sibley et al., "The relevance of the polymicrobial nature of airway infection in the acute and chronic management of patients with cystic fibrosis", Curr Opin Investig Drugs, (2009), 10: 787-794.

Sibley et al., "The polymicrobial nature of airway infections in cystic fibrosis: Cangene Gold Medal Lecture", Can J Microbiol, (2011), 57: 69-77.

Simons et al., "Dual effects of plant steroidal alkaloids on *Saccharomyces cerevisiae*", Antimicrob Agents Chemother, (2006), 50: 2732-2740.

Songer, J.G. "Clostridia as agents of zoonotic disease", Vet Microbiol, (2010), 140: 399-404.

Songer et al., "Clostridial enteric infections in pigs", J. Vet. Diagn. Invest. (2005),17:528-536.

Stepan et al., "Molecular diagnostics of clinically important staphylococci", Folia Microbiol (Praha), (2004), 49: 353-386.

Stewart, P.S. "Mechanisms of antibiotic resistance in bacterial biofilms", Int J Med Microbiol, (2002), 292: 107-113.

Talbot et al., "Bad bugs need drugs: an update on the development pipeline from the Antimicrobial Availability Task Force of the Infectious Diseases Society of America", Clin Infect Dis, (2006), 42: 657-668.

Tenhagen et al, "Prevalence of mastitis pathogens and their resistance against antimicrobial agents in dairy cows in Brandenburg, Germany", J Dairy Sci, (2006), 89(7): 2542-51.

Tuchscherr et al., "*Staphylococcus aureus* phenotype switching: an effective bacterial strategy to escape host immune response and establish a chronic infection". EMBO Mol Med, (2011), (in press).

Van Immerseel et al., "Clostridium perfringens in poultry: an emerging threat for animal and public health", Avian Pathol., (2004), 33:537-549.

Vergison et al., "National survey of molecular epidemiology of *Staphylococcus aureus* colonization in Belgian cystic fibrosis patients", J. of Antimicrob Chemother, (2007), 59:893-899.

Vial et al., "Burkholderia pseudomallei, B. thailandensis, and B. ambifaria produce 4-hydroxy-2-alkylquinoline analogues with a methyl group at the 3 position that is required for quorum-sensing regulation", J Bacteriol, (2008), 190: 5339-5352.

Voggu et al., "Microevolution of cytochrome bd oxidase in Staphylococci and its implication in resistance to respiratory toxins released by Pseudomonas", J Bacteriol, (2006), 188: 8079-8086.

Vuong et al., "*Staphylococcus epidermidis* infections"m, Microbes Infect, (2002), 4: 481-489.

Wellinghausen et al., "Characterization of clinical Enterococcus faecalis small-colony variants", J Clin Microbiol, (2009), 47: 2802-2811.

Wilson et al., "Selection and characterization of strains of *Staphylococcus aureus* displaying unusual resistance to aminoglycosides", Antimicrob Agents Chemother, (1976),10: 519-525.

Witte et al., "Emergence and spread of antibiotic-resistant Gram-positive bacterial pathogens", Int J Med Microbiol, (2008), 298: 365-377.

Wong, et al., "A Concise Synthesis of Atipamezole", Synthesis (1995), 139-140.

IPRP in PCT/CA2012/050087 to Socpra Sciences Et Génie, S.E.C. et al. (Aug. 29, 2013).

Adam, et al., "Solanum-Alkaloide XXVI, Praparative trennung stereoisomerer Imino-choelstane und weiterer Steroide durch

(56) References Cited

OTHER PUBLICATIONS

Dunnschicht-Chromatographie unter Verwendung von Jod als indifferentes Nachweisreagens", Z. chem., 1963, 3(3), p. 100-102.
Adam, et al., "Solanum-Alkaloide XXXIX, Synthese von 22,26-imino-5alpha-cholestan-3beta-olen aus 3beta acetoxy-pregn-5-en-20-on und deren sterische zuordnung", Tetrahedron, 1964, 20(7), p. 1707-1718.
Armas, et al., "Steroidal N-Nitrosoamines. Part 4. Intramolecular Functionalization of N-Nitroamine Radicals: Synthesis of 1,4-Nitroimine Compounds", J. Chem. Soc. Perkin Trans. I, 1988, I2, p. 3255-3265.
Bird, et al., "Soladunalinidine, a new steroidal alkaloid from Solanum dunalianum", Tett. Lett., 1978, 2, p. 159-160.
Bird, et al., "Structures of the Steroidal Alkaloids 25-Isosolaforidine and Solacallinidine Isolated from Solanum Gallium", Aust. J. Chem., 1979, 32(3), p. 597-609.
Chagnon et al., "Unraveling the structure-activity relationship of tomatidine, a steroid alkaloid with antibiotic properties against persistent form of *Staphylococcus aureus*", Eur J Med Chem, Jun. 10, 2014; 80:605-20. (Abstract).
Coleman, et al., "Characterization of Plant-Derived Saponin Natural Products against Candida albicans", ACS Chem. Biol., 2010, 5(3), p. 321-332.
Kircher, et al., "Preparation of Some Unsaturated Side-Chain Derivatives of Cholesterol", J. Org. Chem., 1982, 47 (9), p. 1722-1724.
Kraml, "Agents affecting Lipid Metabolism. XXVI. Specificity of Some Inhibitors of the Late Stages of Cholesterol Biosynthesis", Lipids, 1967, 2(1), p. 5-7.
Kusano, et al., "Antifungal Properties of Solanum Alkaloids", Chem. Pharm. Bull., 1987, 35(12), p. 4862-4967.
Lavie, et al., "Inhibitory Effect of Steroidal Alakloids on Drug Transport and Multidrug Resistance in Human Cancer Cells", Anticancer Res., 2001, 21(2A), p. 1189-1194.
Maxwell, et al. "3beta-Aminospirosolane alkaloids from Solanum triste", J. Nat. Prod., 1995, 58(4), p. 625-628.
Maxwell, et al. "3-Aminospirosolane alkaloids from Solanum arboreum", Phytochemistry, 1996, 43(4), p. 913-915.
Mazur, et al., "The synthesis of the Steroidal Sapogenins", J. Am. Chem. Soc., 1960, 82(22), p. 5889-5908.
McKenna, "Steroidal Alkaloids", Quaterly reviews, Chemical Society, 1953, 7(3), p. 231-254.
Meccia, et al., "On the Configuration of Solaquidine", J. Nat. Prod., 1987, 50(4), p. 642-645.
Milner, et al., "Bioactivities of Glycoalkaloids and Their Aglycones from Solanum Species", J. Agric. Food Chem., 2011, 59, p. 3454-3484.
Nagaoka, et al., "Steroidal alkaloids from roots of tomato stock", Phytochem. 1993, 34(4), p. 1153-1157.
Nino, et al. "Biological activities of steroidal alkaloids isolated from Solanum leucocarpum", Pharmaceutical Biology, 2009, 47(3), p. 255-259.
Paulsen, et al., "Monosaccharide mit stickstoffhaltigem Ring, XIV Untersuchungen uber die magnetische Anisotropie der Amidgruppe", Chem. Ber., 1967, 100(10), p. 3385-3396.
Rowan, et al., "Antifungal stress metabolites from Solanum aviculare", Phytochem., 1983, 22(9), p. 2102-2104.
Quyen, et al., "Synthesis of the Steroid Alkaloid Soladunalinidine and Other 5alpha-Spirosolan-3-amines", Liebigs Ann. Chem., 1990, 6, p. 519-524.
Sato, et al., "New Dihydro Derivatives of Tomatidine and Solasodine", J. Am. Chem. Soc., 1956, 78(13), p. 3150-3153.
Sato, et al., "Chemistry of the Spiroaminoketal Side Chain of Solasodine and Tomatidine. IV. Chemistry of the Tomatidine Side Chain", J. Org. Chem., 1960, 25, p. 1962-1965.
Sato, et al., "Structure of Tomatillidine", J. Org. Chem., 1965, 30(3), p. 754-760.
Sato, et al., "Alkaloids from Solanum congestiflorum", J. Org. Chem., 1969, 34(6), p. 1577-1582.

Schreiber, et al., "Uber Tomatid-5-en-3beta-ol aus *Solanum dulcamara* L. und dessen abbau zu 3beta-acetoxypregna-5,16-dien-20-on", Justus Liebigs Annalen der Chemie, 1965, 34(6), p. 1577-1582.
Tschesche, et al., "Zur Biogenese Des Aza-Oxa-Spiran-Systems Der Steroidalkoide Vom Spirosolan-typ in sonaceen", Phytochem, 1978, 17(2), p. 251-255.
Tschesche, et al., "Zur Syntheese von 22,26-Epiminocholestanolen", Chem Ber., 1978b, 111(2), p. 801-802.
Ubuka, "Experimental isovalthinuria. III. Induction by bile acids, and hypocholesterolemic agents", Acta med. Okayama, 1963, 17(6), p. 273-278.
Uhle, "The Synthesis of Azaoxaspirane Steroid Alkaloids", J. Am. Chem. Soc., 1961, 83(6), p. 1460-1472.
Xie, et al. "Structure-Activity Relationship of Aza-Steroids as PI-PLC Inhibitors", Bioorg. Med. Chem., 2001, 9(5), p. 1073-1083.
Zha, et al. "Synthesis and in vitro antitumor activities of novel soladulcidine derivatives", Zhongguo Yaoke Daxue Xuebao (Journal of China Phamraceutical University), 2010, 41(6), p. 493-498.
Google English translation of CN101054399 to Tian.
Google English translation of CN101406564 to Gang et al.
Google English translation of CN101664555 to Jie et al.
ISR and WO in PCT/CA2012/050087 to Socpra Sciences Et Génie, S.E.C. et al. (Aug. 29, 2013).
European Search Opinion and Supplementary Search Report in EP2675822 to Socpra Sciences Et Génie, S.E.C. et al. (Jul. 2, 2014).
Devkota et al., "Bioactive 5.alpha.-pregnane-type steroidal alkaloids from Sarcococca hookeriana", Journal of Natural Products, American Chemical Society, 2008, 71(8), p. 1481-1484.
Alexander et al., "Factors influencing the internalization of *Staphylococcus aureus* and impacts on the course of infections in humans", Appl Microbiol Biotechnol, (2001), 56: 361-366.
Allegrucci et al., "Formation of *Streptococcus pneumoniae* non-phase-variable colony variants is due to increased mutation frequency present under biofilm growth conditions", J Bacteriol, (2008), 190: 6330-6339.
Archer G.L., "*Staphylococcus aureus*: a well-armed pathogen", Clin Infect Dis, (1998), 26: 1179-1181.
Atalla et al., "Characterization of a *Staphylococcus aureus* small colony variant (SCV) associated with persistent bovine mastitis", Foodborne Pathog, (2008), Dis 5: 785-799.
Ayesa et al. "Solid-phase parallel synthesis and SAR of 4-amidofuran-3-one inhibitors of cathepsin S: effect of sulfonamides P3 substituents on potency and selectivity", Bioorg Med Chem, (2009) 1307-24.
Bad Bug Book, *Bacillus cereus* and other *Bacillus* spp. Foodborne Pathogenic Microorganisms and Natural Toxins Handbook, Food and Drug Administration, (www.fda.gov), (2012).
Bednarek et al., "Plant-microbe interactions: chemical diversity in plant defense", Science, (2009) 324: 746-748.
Beierlein et al., "New developments in vaccines, inhibitors of anthrax toxins, and antibiotic therapeutics for Bacillus anthracis", Curr Med Chem., (2011), 18(33):5083-94.
Black, J.G., "Microbiology: Principles and Explorations" 7th ed. John Wiley & Sons (2008).
Bolger et al., In vitro and in vivo activity of 16,17-dehydro-epipregnanolones: 17,20-bond torsional energy analysis and D-ring conformation. Pharm Res, (2008) 1996, 13, 1488-94.
Bouarab et al., "Plant stress response agents affect *Staphylococcus aureus* virulence genes. Abstr. 47th Intersci. Conf. Antimicrob", Agents Chemother., abstr., (2007), C1-1483.
Boulanger et al., "Tomatidine is bactericidal against *Staphylococcus aureus* in co-culture with Pseudomonas aeriginosa strains producing HQNO", Interscience Conference on Antimicrobial Agents and Chemotherapy, Abstr. F-1998, San Francisco, Sep. 9-12, 2012.
Brouillette et al., "Persistence of a *Staphylococcus aureus* small-colony variant under antibiotic pressure in vivo", FEMS Immunol Med Microbiol, (2004), 41: 35-41.
Brouillette et al., "Mouse mastitis model of infection for antimicrobial compound efficacy studies against intracellular and extracellular forms of *Staphylococcus aureus*" Vet. Microbiol. (2004b), 101:253-262.

(56) References Cited

OTHER PUBLICATIONS

Bryan et al., "Mechanisms of aminoglycoside resistance of anaerobic bacteria and facultative bacteria grown anaerobically", J Antimicrob Chemother, (1981) 8 Suppl D: 1-8.
Canadian Cystic Fibrosis Foundation (2007) Patient data registry report. Toronto, ON, Canada.
Casey et al., "Staphylococci", Int J Antimicrob Agents 29 Suppl, (2007), 3: S23-32.
Chagnon et al., "Unraveling the structure-activity relationship of tomatidine, a steroid alkaloid with antibiotic properties against persistent form of *Staphylococcus aureus*", 96th Canadian Chemistry Conference and Exhibition, Canadian Society for Chemistry, Abstr. 01555, Quebec City, May 26-30, 2013.
Chagnon et al., "Steroidal alkaloids as aminoglycoside-enhancing drugs", 96th Canadian Chemistry Conference and Exhibition, Canadian Society for Chemistry, Abstr. 01464, Quebec City, May 26-30, 2013.
Chagnon et al. "Optimisation of a novel steroid alkaloid antibiotic efficient against persistent form of *Staphylococcus aureus*", 95th Canadian Chemistry Conference and Exhibition, Canadian Society for Chemistry, Calgary, May 26-30, 2012.
Chambers et al., "Waves of resistance: *Staphylococcus aureus* in the antibiotic era", Nat Rev Microbiol (2009), 7: 629-641.
Chastre et al., "Ventilator-associated pneumonia", Am J Respir Crit Care Med, (2002), 165: 867-903.
Chatterjee et al., "Enhanced post-stationary-phase survival of a clinical thymidine-dependent small-colony variant of *Staphylococcus aureus* results from lack of a functional tricarboxylic acid cycle", J Bacteriol, (2007),189: 2936-2940.
Clinical and Laboratory Standards Institute (CLSI), "Methods for dilution antimicrobial susceptibility tests for bacteria: Approved Standard", (2006).
Cystic Fibrosis Foundation, "Patient registry annual report. Washington, D.C.", (2008).
Dasenbrook et al., "Association between respiratory tract methicillin-resistant *Staphylococcus aureus* and survival in cystic fibrosis", Jama, (2010), 303: 2386-2392.
Deslouches et al., "Activity of the De Novo Engineered Antimicrobial Peptide WLBU2 against Pseudomonas aeruginosa in Human Serum and Whole Blood: Implications for Systemic Applications. Antimicrob. Agents chemother", (2005), 49: 3208-3216.
Eliopoulos et tal., "Antimicrobial combinations", In Antibiotics in Laboratory Medicine, 4th ed. (V. Lorian, Ed.), (1996), pp. 330-396. Williams and Wilkins, Baltimore, MD.
Friedman, M. "Tomato glycoalkaloids: role in the plant and in the diet", J Agric Food Chem, (2002) 50(21): 5751-5780.
Galli, J., "Recurrent upper airway infections and bacterial biofilms", J Laryngol Otol, (2007) 121: 341-344.
Gattuso et al., "Plant Stress Response Agents Affect *Staphylococcus aureus* Virulence Genes", Interscience Conference on Antimicrobial Agents and Chemotherapy (ICAAC), (2007): 17-20.
Gibson et al., "Pathophysiology and Management of Pulmonary Infections in Cystic Fibrosis", Am J Respir Crit Care Med, (2003), 168: 918-951.
Ginnes et al., "Respiration. In *Escherichia coli* and *Salmonella*", Cellular and Molecular Biology, (1996), p. 217-261. Ed. F. C. Neidhardt. American Society for Microbiology, Washington.
Goerke et al., "Regulatory and genomic plasticity of *Staphylococcus aureus* during persistent colonization and infection"Int J Med Microbiol, (2004), 294: 195-202.
Gonzalez-Lamothe et al., "Plant antimicrobial agents and their effects on plant and human pathogens". Int J Mol Sci, (2009), 10: 3400-3419.
Guay et al., Antibacterial spectrum and structure-activity relationship of tomatidine analogs. Interscience Conference on Antimicrobial Agents and Chemotherapy, Abstr. F-1997, San Francisco, Sep. 9-12, 2012.
Guillet et al. "Human Listeriosis Caused by Listeria ivanovii", Emerging Infectious Diseases, (2010), 16:136-138.
Harlid et al., "Respiratory tract colonization and infection in patients with chronic tracheostomy. A one-year study in patients living at home", Am J Respir Crit Care Med, (1996), 154: 124-129.
Harrison, F., "Microbial ecology of the cystic fibrosis lung", Microbiology, (2007), 153: 917-923.
Hecht, D.W., "Anaerobes: antibiotic resistance, clinical significance, and the role of susceptibility testing", Anaerobe, (2006), 12: 115-121.
Hoffman et al., "Selection for *Staphylococcus aureus* small-colony variants due to growth in the presence of Pseudomonas aeruginosa", Proc Natl Acad Sci U S A, (2006),103: 19890-19895.
Jacques et al., Biofilm formation in bacterial pathogens of veterinary importance. Anim Health Res Rev, (2010), 11: 97-121.
Kessler et al., "Secreted LasA of Pseudomonas aeruginosa is a staphylolytic protease", J Biol Chem, (1993), 268: 7503-7508.
Kloos et al., "Update on clinical significance of coagulase-negative Staphylococci", Clin Microbiol Rev, (1994), 7: 117-140.
Li et al., Expeditious synthesis of hippuristanol and congeners with potent antiproliferative activities, Chemistry (2009), 15, 10356-9.
Lightbown et al., "Inhibition of cytochrome systems of heart muscle and certain bacteria by the antagonists of dihydrostreptomycin: 2-alkyl-4-hydroxyquinoline N-oxides", Biochem J, (1956), 63: 130-137.
Lyczak et al., "Lung infections associated with cystic fibrosis", Clin Microbiol Rev, (2002), 15: 194-222.
Machan et al., "2-Heptyl-4-hydroxyquinoline N-oxide, an antistaphylococcal agent produced by Pseudomonas aeruginosa", J Antimicrob Chemother, (1992), 30: 615-623.
Malouin et al., "Identification of antimicrobial compounds active against intracellular *Staphylococcus aureus*", FEMS Immunol. Med. Microbiol, (2005), 45:245-252.
Martin-Hernandez et al., "Effects of targeted replacement of the tomatinase gene on the interaction of Septoria lycopersici with tomato plants", Mol Plant Microbe Interact, (2000),13: 1301-1311.

STEROID ALKALOIDS AND USES THEREOF AS ANTIMICROBIAL AGENTS AGAINST ELECTRON TRANSPORT-DEFICIENT MICROBES AND AS POTENTIATORS FOR ANTIMICROBIAL AGENTS AGAINST PATHOGENIC BACTERIA

CROSS-REFERENCE TO RELATED APPLICATIONS

This application is a National Entry Application of PCT application no. PCT/CA2012/050087* filed on Feb. 15, 2012 and published in English under PCT Article 21(2), claiming benefit of U.S. Provisional applications Ser. No. 61/442,948, filed on Feb. 15, 2011. All documents above are incorporated herein in their entirety by reference.

FIELD OF THE INVENTION

The present invention relates to novel antimicrobial compounds and potentiators for antimicrobial compounds. More specifically, the present invention is concerned with the use of steroid alkaloids as antimicrobial agents, and potentiators of the antimicrobials activity of aminoglycosides against pathogenic bacterial strains, methods of manufacturing same, disinfection, sterilization or antisepsis methods using the same.

BACKGROUND OF THE INVENTION

*Staphylococci*

*Staphylococci* are widely disseminated Gram-positive opportunistic bacterial pathogens responsible for many medical problems in humans, including skin and soft-tissue infections, surgical infections, endocarditis and hospital-acquired bacteriemia (Casey et al., 2007; Kloos and Bannerman, 1994). These bacteria are also the cause of several diseases in animals such as birds, cows, dogs, poultries, rabbits and others (Jacques et al., 2010; Pyorala and Taponen, 2009; Stepan et al., 2004). *Staphylococci* are divided in coagulase-positive species, *Staphylococcus aureus* (*S. aureus*) being the most clinically relevant of this group, and coagulase-negative species, such as *Staphylococcus epidermidis* (*S. epidermidis*), the most prevalent pathogen associated with infections of implanted medical devices (Vuong and Otto, 2002). The emergence and spread of resistance to multiple antibiotics in *staphylococci* is now considered a real health treat and impaired therapeutic endeavor to combat these bacteria (Witte et al., 2008).

*S. aureus* is an opportunistic pathogen that has extraordinary versatility. Diseases caused by this pathogen can affect several hosts, organs and body sites and may become both life threatening as well as chronic (Archer, 1998; Goerke and Wolz, 2004). For example, *S. aureus* is associated with significant mortality rates in hospitals and increased health costs (Talbot et al., 2006), but is also the most common cause of difficult-to-treat bovine mastitis (Sears and McCarthy, 2003). The ability of *S. aureus* to cause a broad spectrum of diseases is related to its numerous virulence factors (Archer, 1998) and it is likely that the coordinated or selected expression of specific groups of virulence factors contribute to the development of specific types of infections. For example, the formation of biofilms and the persistence within non-phagocytic host cells seem to facilitate the development of chronic infections by offering the bacterium protection against the host immune system and the action of antibiotics (Alexander and Hudson, 2001; Brouillette et al., 2004; Galli et al., 2007; Stewart, 2002).

Bacterial Small-Colony Variants

Bacterial small-colony variants (SCVs) are derived from normal bacterial strains and show a slow-growth phenotype (i.e., they produce small colonies when cultivated on solid media). *S. aureus* SCVs are known to form biofilms (Mitchell et al., 2010a; Mitchell et al., 2010b) and persist within non-phagocytic host cells (Sendi and Proctor, 2009). SCVs are bacteria with a dysfunctional oxidative metabolism causing an alteration in the expression of virulence factors, a slow growth and a loss of colony pigmentation (Proctor et al., 2006). This dysfunctional oxidative metabolism causes a decreased susceptibility to aminoglycosides because these antibiotics require the proton-motive force in order to penetrate the bacterium (Bryan and Kwan, 1981). In *S. aureus*, the SCV phenotype results from mutations affecting the electron-transport system and several SCV isolates are auxotrophic for either hemin or menadione, which are needed to synthesize electron-transport system components. SCVs can also be auxotrophic for thiamine because thiamine is required for the biosynthesis of menadione. Other SCVs are no longer able to synthesize thymidine due to mutations in the folate pathway and this also results in a defect in electron transport although the fundamental basis of this is not well understood (Proctor et al., 2006). Some SCVs present yet unknown auxotrophy but still have in common electron transport deficiency which may result, for example, from a defect in the bacterial $F_0F_1$-ATPase (Proctor et al., 2006). *S. aureus* SCVs are isolated from chronic infections, such as lung infections in cystic fibrosis (CF) patients and from osteomyelitis, septic arthritis, bovine mastitis and infection of orthopedic devices (Atalla et al., 2008; Moisan et al., 2006; Proctor et al., 2006). SCVs that are MRSA (methicillin-resistant *S. aureus*) and multiresistant to several class of antibiotics have also been reported (Vergison et al, 2007). It is now thought that switching from the normal to the SCV phenotype is an integral part of the pathogenesis of *S. aureus* and that novel therapeutic strategies targeting SCVs are needed to combat infections caused by bacterial species capable of generating electron transport-deficient SCVs (Tuchscherr et al., 2011).

The SCV phenotype is widespread among microbes. SCVs have been described for several bacterial species and have been recovered from many different clinical specimens such as abscesses, blood, bones and joints, the respiratory tract and soft tissues (Proctor et al., 2006). For examples, SCVs were detected among the *staphylococci* such as *S. aureus*, *S. epidermidis*, *Staphylococcus lugdunensis* and *Staphylococcus capitis*, among the enteric-disease causing bacteria such as *Salmonella* serovars, *Shigella* spp., *Escherichia coli* and *Vibrio cholerae*, among the nosocomial pathogens such as *Pseudomonas aeruginosa*, *Burkholderia cepacia*, *Escherichia coli*, *Serratia marcescens*, *Stenotrophomonas maltophilia* and *Enterococcus faecalis*, among the respiratory tract pathogens such as *Streptococcus pneumoniae* and *Corynebacterium* spp., among uro-genital pathogens such as *Neisseria gonorrhoeae* and also in a variety of other species such as *Brucella melitensis* and *Lactobacillus lactophilus* (Allegrucci and Sauer, 2008; Melter and Radojevic, 2010; Proctor et al., 2006; Wellinghausen et al., 2009). In most of these cases, the SCV phenotype is consequent to a defect in the electron transport chain either caused by alteration of electron transport proteins, restriction in necessary coenzymes, cofactors or precursors or an overall reduction of some metabolic pathways such as the tricarboxilic cycle that ultimately affect and reduce electron transport (Chatterjee et al., 2007; Proctor et al., 2006).

Anaerobic Bacteria

Anaerobic bacteria predominantly constitute the indigenous flora of human and are the source of infections affecting virtually all organs (Nagy, 2010), and the prevalence of antibiotic resistance in several anaerobic pathogens is increasing (Hetch et al., 2006; Nagy, 2010). Among the numerous anaerobic bacteria causing human diseases are the clostridia (Hetch et al., 2006; Nagy, 2010), also known to be sources of infections in animals (Songer, 2010). The better example is probably *Clostridium difficile*, now considered to be an important cause of infections associated with healthcare (Rupnik et al., 2009). Another good example is *Clostridium perfringens*, which is the third in incidence among pathogen causing food-borne illness in the USA (Mead et al., 1999; Songer, 2010) and diseases in pigs and chickens (Van Immerseel et al., 2004; Songer and Uzal, 2005).

Cystic Fibrosis

Although cystic fibrosis (CF) is fundamentally a genetic disorder, the majority of patients afflicted by this disease will ultimately succumb from respiratory failure subsequent to chronic bacterial infections (Lyczak et al., 2002). More recent investigations reveal that the CF airways are colonized by complex polymicrobial communities constituted of numerous microorganisms, encompassing more bacterial species than originally thought, and suggest that interactions between these microorganisms influence the course of the disease (Sibley and Surette, 2011). Some focus has been directed toward understanding the outcome of the interactions between *P. aeruginosa* and *S. aureus* because they are often co-isolated from the CF airways (Harrison, 2007; Hoffman et al., 2006; Mitchell et al., 2010b). The polymicrobial nature of CF lung infections needs to be considered in the development of novel therapeutic approaches (Sibley et al., 2009; Sibley and Surette, 2011).

*Staphylococcus aureus* is one of the most common pulmonary pathogens recovered from North American CF patients (Canadian Cystic Fibrosis Foundation, 2007; Cystic Fibrosis Foundation, 2008). While it is well accepted that antibiotic therapy leads to improvement of lung function and may reduce morbidity associated with CF, decisions regarding which antibiotics to use and when to treat remain largely empirical (Lyczak et al., 2002; Parkins and Elborn, 2010). Consequently, many antibiotics are currently used to treat CF patients infected with bacteria, including aminoglycoside antibiotics (Gibson et al., 2003; Lyczak et al., 2002). A major problem encountered by CF patients is the emergence of bacteria resistant to antibiotics. For example, the prevalence of methicillin-resistant *Staphylococcus aureus* (MRSA), most often multi-resistant to antibiotics (Chambers and Deleo, 2009), is increasing among CF patients (Parkins and Elborn, 2010). MRSA infections has been associated with a decline of lung function in CF patients (Dasenbrook et al., 2010).

Bovine Mastitis

Bovine mastitis is the most frequently occurring and costly disease affecting dairy producers. The transmittable bacterium *Staphylococcus aureus*, the coagulase-negative staphylococci and also many streptococci (*S. agalactiae, S. dysgalactiae, S. uberis* and others) are amongst the most common causes of intramammary infections leading to bovine mastitis (Tenhagen et al., 2006) and current antibiotic therapies usually fail to eliminate the infection from dairy herds (Sears, P. M. and K. K. McCarthy, 2003). Both the normal and SCV phenotypes of pathogenic bacteria were recovered from mastitis cases (Atalla et al., 2008).

Antibiotic-Resistant Bacteria

Infections caused by antibiotic-resistant bacteria represent an overwhelming growing problem both in human and veterinary medicine. One reason explaining this widespread of drug resistances is that the currently available antibiotics have been largely designed on a limited number of chemical scaffolds, which allowed pathogens to adapt and circumvent common antibiotic action mechanisms (Shah, 2005; Talbot et al., 2006).

Foodborne Bacteria and Illnesses

A number of bacterial species such as *Listeria* spp. and *Bacillus* spp. can contaminate food and cause infections in humans. To name a few, *Listeria monocytogenes, L. ivanovii*, and *Bacillus cereus* can cause listeriosis (Guillet et al, 2010) and food poisoning (Bad Bug Book, FDA). *Bacillus subtilis, B. coagulans, B. licheniformis* and *B. sphaericus* are also known to cause illnesses. *Bacillus anthracis* causes anthrax and can often be acquired by contact with food producing animals and cattle (beef cattle, sheeps, etc.) and this bacterium is also well-known for its endospores that have been used as biological weapons (Beierlein and Anderson, 2011).

It would be highly desirable to identify antibiotic compounds targeting electron transport-deficient microbes (e.g., SCVs and anaerobe bacteria) and/or potentiating the growth inhibitory activity of aminoglycosides against pathogenic bacteria (e.g., antibiotic-resistant bacteria and/or those causing chronic infections) and/or reducing bacterial resistance development toward aminoglycosides. It would also be highly desirable to identify antibiotic compounds that can be used to reduce bacterial colonization in food, preserve food or treat infections caused by foodborne pathogens.

The present description refers to a number of documents, the content of which is herein incorporated by reference in their entirety.

SUMMARY OF THE INVENTION

The present invention relates in part to the discovery that steroid alkaloids specifically and selectively inhibit the growth of electron transport-deficient microbes.

In accordance with one aspect, the present invention provides steroid alkaloids for use as antibiotic-like compounds with antimicrobial activity against pathogenic electron transport-deficient microbes (e.g., SCVs, anaerobe bacteria, bacteria affected by another organism producing inhibitors of the electron transport chain).

In accordance with another aspect, the present invention provides steroid alkaloids for use as agents potentiating the antimicrobial activity of aminoglycosides against a variety of bacteria that do not have electron-transport deficiency.

In accordance with another aspect, the present invention provides steroid alkaloids for use as agents reducing the development of bacterial resistance toward aminoglycosides.

Compounds

More specifically, in accordance with one aspect, the present invention provides a compound of formula:

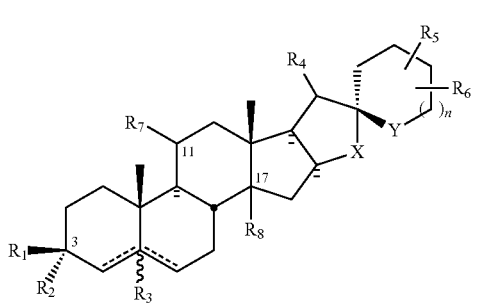 (1.0)

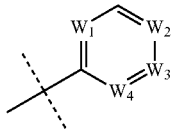 Het1

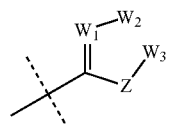 Het2

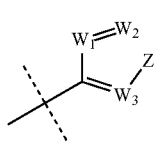 Het3

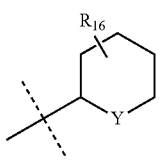 Het4 wherein, (1) R1 is H, OH, NH$_2$, NHR12, N(R12)$_2$ or OR12; and R2=H; or (2) R2 is H, OH, NH$_2$, NHR12, N(R12)$_2$ or OR12; and R1=H; or (3) R1 and R2 together form =O or =NR12; R3 is α-H, β-H, α-alkyl, β-alkyl, α-OH or β-OH, or is absent when the double bond is present either in C4=C5, or in C5=C6; - - - - - is an optional double bond; R4-R6 are identical or different and are H, alkyl, OH, OR12, NHR12 or N(R12)$_2$; R7 is H, α-OH or β-OH; R8 is α-H, β-H, α-OH or β-OH; X and Y are identical or different and are O, NR12 or CH$_2$; R12 is H, alkyl, aryl, COalkyl, COaryl, CO$_2$alkyl, CO$_2$aryl, CONHalkyl, CONHaryl, SO$_3$H, SO$_2$alkyl, SO$_2$aryl, SO$_2$N(R12)$_p$, PO$_3$H$_2$, CO-amino-acid, CH$_2$—NH—R14, C(=NH)NHR4, (CH$_2$)$_m$CO$_2$H, (CH$_2$)$_m$SO$_3$H, (CH$_2$)$_m$NH$_2$ (CH$_2$)$_m$NHC(=NH)NH$_2$, or (CH$_2$)$_m$—C(=NH)NH$_2$; NHalkyl or NHaryl; R14 is H, alkyl, aryl, COalkyl, COOalkyl, COaryl, CO$_2$aryl, SO$_2$alkyl, SO$_2$aryl, SO$_2$N(R12)$_p$ or CO-amino-acid; n is 0-5; m is 1-5; p=1-2, wherein the compound of formula 1.0 is not tomatidine or solasodine;

or

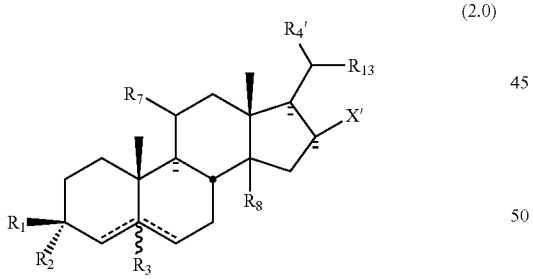 (2.0)

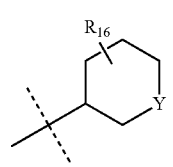 Het5

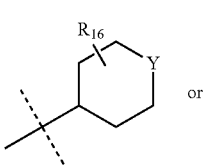 Het6 or

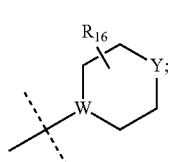 Het7

X' is H, OR14 or NHR14, wherein R14 is H, alkyl, aryl, COalkyl, COaryl, CO$_2$alkyl, CO$_2$aryl, CONHalkyl, CONHaryl, SO$_3$H, SO$_2$alkyl, SO$_2$aryl, SO$_2$N(R12)$_p$, PO$_3$H$_2$, CO-amino-acid, CH$_2$—NH—R14, C(=NH)NHR4, (CH$_2$)$_m$CO$_2$H, (CH$_2$)$_m$SO$_3$H, (CH$_2$)$_m$NH$_2$ (CH$_2$)$_m$NHC(=NH)NH$_2$, or (CH$_2$)$_2$, C(=NH)NH$_2$; R1, R2, R3, R7 and R8 are as defined above; R4' is H, alkyl or aryl; R13 is NHR15, wherein R15 is H, alkyl, aryl, COalkyl, COaryl, CO$_2$alkyl, CO$_2$aryl, CONHalkyl, CONHaryl, SO$_3$H, SO$_2$alkyl, SO$_2$aryl, SO$_2$N(R12)$_p$, PO$_3$H$_2$, CO-amino-acid, CH$_2$—NH—R14, C(=NH)NHR4, (CH$_2$)$_m$CO$_2$H, (CH$_2$)$_m$SO$_3$H, (CH$_2$)$_m$NH$_2$ (CH$_2$)$_m$NHC(=NH)NH$_2$, or (CH$_2$)$_m$—C(=NH)NH$_2$; or wherein W1, W2, W3, W4 are identical or different and are independently N or CH; R16 is H, alkyl or aryl; Y is CH$_2$, NH, N-alkyl, N—COalkyl, N—COaryl, N—SO$_2$alkyl, N—SO$_2$aryl, NH—C(=NH)NH$_2$, N—CO$_2$alkyl or N—CO$_2$aryl; and Z is NH, NR17, S or O, where R17 is H, alkyl, aryl, COalkyl, COaryl, CO$_2$alkyl, CO$_2$aryl, CONHalkyl, CONHaryl, SO$_3$H, SO$_2$alkyl, SO$_2$aryl, SO$_2$N(R12)$_p$, PO$_3$H$_2$, CO-amino-acid, CH$_2$—NH—R14, C(=NH)NHR4, (CH$_2$)$_m$CO$_2$H, (CH$_2$)$_m$SO$_3$H, (CH$_2$)$_m$NH$_2$, (CH$_2$)$_m$NHC (=NH)NH₂, or (CH₂)ₘ—C(=NH)NH₂; wherein the compound of formula 2.0 is not dihydrosolacongestidine; or

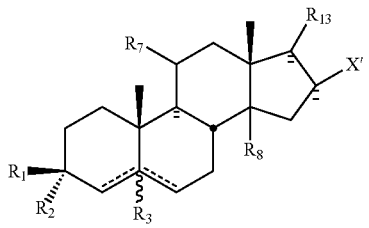

(3.0)

wherein R1, R2, R3, R7, R8, R13 and X' are as defined above; or

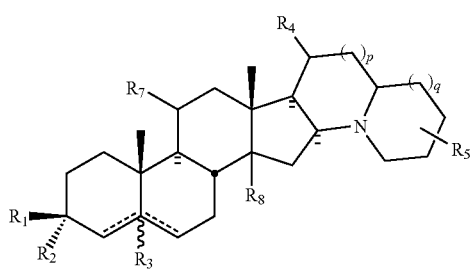

(4.0)

wherein R1, R2, R3, R4, R5, R7 and R8 are as defined above; p is 0-5; and q is 0-5, wherein the compound of formula 4.0 is not demissidine.

In a specific embodiment of the compound, the compound is of formula 1.0 and (i) R1 is OR12 or H; (ii) R2 is OR12 or H; (iii) R3 is H; (iv) R4 is CH₃; (v) R5 is H; (vi) R6 is CH₃; (vii) R7 is H; (ix) R8 is H; (x) n is 1; (xi) X is O; (xii) Y is NH; or (xiii) any combination of (i) to (xii).

In another specific embodiment of the compound, the compound is of formula 1.1:

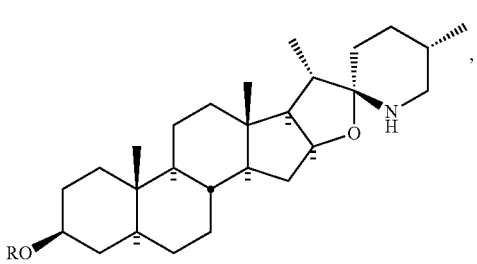

(1.1)

wherein R is alkyl, aryl, COalkyl, COaryl, CO₂alkyl, CO₂aryl, CONHalkyl, CONHaryl, SO₃H, SO₂alkyl, SO₂aryl, SO₂N(R12)ₚ, PO₃H₂, CO-amino-acid, CH₂—NH—R14, C(=NH)NHR4, (CH₂)ₘCO₂H, (CH₂)ₘSO₃H, (CH₂)ₘNH₂ (CH₂)ₘNHC(=NH)NH₂, or (CH₂)ₘ—C(=NH)NH₂; NHalkyl or NHaryl.

In another specific embodiment of the compound, the compound is of formula 1.0 and R1 is OR12, R2 is H, R3 is H, R4 is CH₃, R5 is H, R6 is CH₃, R7 is H, R8 is H, R12 is SO₃H, n is 1, X is O and Y is NH.

In another specific embodiment of the compound, the compound is of formula 1.0 and R1 is OR12, R2 is H, R3 is H, R4 is CH₃, R5 is H, R6 is CH₃, R7 is H, R8 is H, R12 is PO₃H₂, n is 1, X is O and Y is NH.

In another specific embodiment of the compound, the compound is of formula 1.0 and R1 is OR12, R2 is H, R3 is H, R4 is CH₃, R5 is H, R6 is CH₃, R7 is H, R8 is H, R12 is (CH₂)ₘCO₂H, n is 1, m is 1, X is O and Y is NH.

In another specific embodiment of the compound, the compound is of formula 1.0 and R1 is OR12, R2 is H, R3 is H, R4 is CH₃, R5 is H, R6 is CH₃, R7 is H, R8 is H, R12 is (CH₂)ₘNH₂, n is 1, m is 2, X is O and Y is NH.

In another specific embodiment of the compound, the compound is of formula 1.0 and R1 is OR12, R2 is H, R3 is H, R4 is CH₃, R5 is H, R6 is CH₃, R7 is H, R8 is H, R12 is (CH₂)ₘCH₂, n is 1, m is 1, X is O and Y is NH.

In another specific embodiment of the compound, the compound is of formula 1.0 and R1 is OR12, R2 is H, R3 is H, R4 is CH₃, R5 is H, R6 is CH₃, R7 is H, R8 is H, R12 is (CH₂)ₘNHC(=NH)NH₂, n is 1, m is 2, X is O and Y is NH.

In another specific embodiment of the compound, the compound is of formula 1.0 and R1 is H, R2 is OR12, R3 is H, R4 is CH₃, R5 is H, R6 is CH₃, R7 is H, R8 is H, R12 is H, n is 1, X is O and Y is NH.

In another specific embodiment of the compound, the compound is of formula 1.0 and R1 and R2 together form =O, R3 is H, R4 is CH₃, R5 is H, R6 is CH₃, R7 is H, R8 is H, n is 1, X is O and Y is NH.

In another specific embodiment of the compound, the compound is of formula 1.0 and R1 is NH2, R2 is H, R3 is H, R4 is CH₃, R5 is H, R6 is CH₃, R7 is H, R8 is H, n is 1, X is O and Y is NH.

In another specific embodiment of the compound, the compound is of formula 1.0 and R1 is OR12, R2 is H, R3 is H, R4 is CH₃, R5 is H, R6 is as defined above, R7 is H, R8 is H, R12 is a protective group, n is 1, X is O and Y is NH.

In another specific embodiment of the compound, the compound is of formula 2.0 and (i) R1 is OH; (ii) R2 is H; (iii) R3 is H; (iv) R4' is CH₃; (v) R7 is H; (vi) R8 is H; or (vii) any combination of (i) to (vi).

In another specific embodiment of the compound, the compound is of formula 2.0 and R1 is OR12, R2 is H, R3 is H, R4' is CH₃, R7 is H, R8 is H, R12 is H, X is H, and R13 is of formula Het1, wherein W1, W2 and W3 are CH and W4 is N.

In another specific embodiment of the compound, the compound is of formula 2.0 and wherein R1 is OR12, R2 is H, R3 is H, R4' is CH₃, R7 is H, R8 is H, R12 is H, X is H, and R13 is of formula Het2, wherein W1 is N, W2 and W3 are CH and Z is S.

In another specific embodiment of the compound, the compound is of formula 2.0 and wherein R1 is OR12, R2 is H, R3 is H, R4' is CH₃, R7 is H, R8 is H, R12 is H, X is H, and R13 is of formula Het4, wherein Y is NH and R16 is H.

In another specific embodiment of the compound, the compound is of formula 2.0 and wherein R1 is OR12, R2 is H, R3 is H, R4' is CH₃, R7 is H, R8 is H, R12 is H, X is OR14, R14 is CH₃, and R13 is of formula Het4, wherein Y is NH and R16 is H.

In another specific embodiment of the compound, the compound is of formula 3.0 and (i) R1 is OR12; (ii) R2 is H; (iii) R3 is H; (iv) R7 is H; (v) R8 is H; (vi) R12 is H; or (vii) any combination of (i) to (vi).

In another specific embodiment of the compound, the compound is of formula 3.0 and R1 is OR12, R2 is H, R3 is H, R7 is H, R8 is H, R12 is H, X is H, and R13 is of formula Het3, wherein W1 is N, W2 and W3 are CH and Z is S.

In another specific embodiment of the compound, the compound is of formula 3.0 and wherein R1 is OR12, R2 is H, R3 is H, R7 is H, R8 is H, R12 is H, X is H, and R13 is of formula Het3, wherein with W1 is N, W2 and W3 are CH and Z is NH.

In another specific embodiment of the compound, the compound is of formula 4.0 and wherein R1 is OR12, R2 is H, R3 is H, R7 is H, R8 is H and R12 is H.

In accordance with another aspect, the present invention provides a compound of formula:

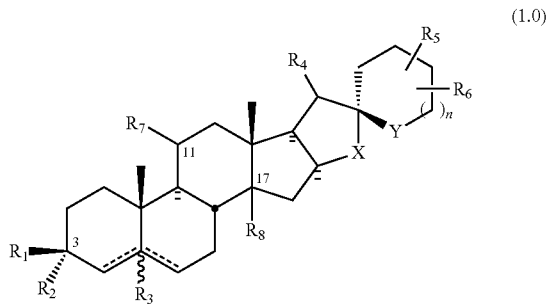

(1.0)

wherein, (1) R1 is H, OH, $NH_2$, NHR12, $N(R12)_2$, N(R12)(R12'), OR12 or SR12; and R2=H; or (2) R2 is H, OH, $NH_2$, NHR12, $N(R12)_2$, N(R12)(R12'), OR12 or SR12; and R1=H; or (3) R1 and R2 together form =O or =NR12; R3 is α-H, β-H, α-alkyl, β-alkyl, α-OH or β-OH, or is absent when the double bond is present either in C4=C5, or in C5=C6; - - - - - is an optional double bond; R4-R6 are identical or different and are H, alkyl, OH, OR18, NHR18 or N(R18)(R18'); R7 is H, α-OH or β-OH; R8 is α-H, β-H, α-OH or β-OH; X and Y are identical or different and are O, NR19, or $CH_2$; R12 and R12' are identical or different and are H, alkyl, aryl, COalkyl, COaryl, $CO_2$alkyl, $CO_2$aryl, CONHalkyl, CONHaryl, $SO_3H$, $SO_2$alkyl, $SO_2$aryl, $SO_2N(R14)_p$, $PO_3H_2$, CO—CH(R20)$NH_2$, $(CH_2)_m$—NH—R14, C(=NH)NHR21, $CH_3OCH_2$, Silylalkyl, $(CH_2)_mCO_2H$, $(CH_2)_mSO_3H$, $(CH_2)_mNH_2$, $(CH_2)_mNHC(=NH)NH_2$, $(CH_2)_m$—C(=NH)$NH_2$, NHalkyl or NHaryl; R14, R22 and R22' are identical or different and are H, alkyl, aryl, COalkyl, $CO_2$alkyl, COaryl, $CO_2$aryl, $SO_2$alkyl, $SO_2$aryl, $SO_2N(alkyl)_p'$ or CO—CH(R20)$NH_2$; R18 and R18' are identical or different and are H, alkyl, aryl, COalkyl, COaryl, CONHalkyl, CONHaryl, $SO_3H$, $SO_2$alkyl, $SO_2$aryl, $SO_2N(alkyl)_{p''}$, $PO_3H_2$, CO—CH(R20')$NH_2$, $(CH_2)_{n''}$—NH—R22, C(=NH)NHR21', $(CH_2)_mCO_2H$, $(CH_2)_mSO_3H$, $(CH_2)_mNH_2$, $(CH_2)_mNHC(=NH)NH_2$, $(CH_2)_m$—C(=NH)$NH_2$, NHalkyl or NHaryl; R19 is H, alkyl, aryl, COH, COalkyl, COaryl, $CO_2$alkyl, $CO_2$aryl, CONHalkyl, CONHaryl, $SO_3H$, $SO_2$alkyl, $SO_2$aryl, $SO_2N(Ralkyl)_{p'''}$, $PO_3H_2$, CO—CH(R20'')$NH_2$, $(CH_2)_{n'''}$—NH—R22', C(=NH)NHR21'', $(CH_2)_{m''}$—$CO_2H$, $(CH_2)_{m''}$—$SO_3H$, $(CH_2)_{m''}$—$NH_2$, $(CH_2)_{m''}$—NHC(=NH)$NH_2$, $(CH_2)_{m''}$C(=NH)$NH_2$, NHalkyl or NHaryl; R20, R20' and R20'' are identical or different and correspond to the side chain of any L- and D-amino acid; R21, R21' and R21'' are identical or different are H, alkyl, OH, Oalkyl, Oaryl, NHalkyl, NHaryl, $N(alkyl)_2$, $N(aryl)_2$, or N(alkyl)(aryl); n, n', n'' and n''' are identical or different and are 0-5; m, m' and m'' are identical or different and are 1-5; and p, p', p'' and p''' are identical or different and are 1-2; wherein the compound of formula 1.0 is not tomatidine, solasodine, 3α-hydroxytomatidine or 3-oxo-tomatidine; or

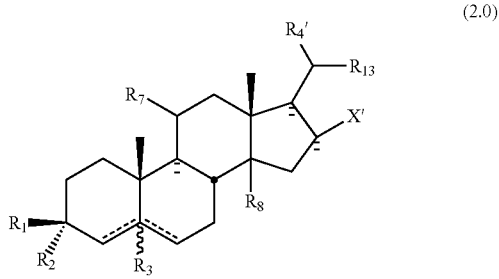

(2.0)

wherein, R1, R2, R3, R7 and R8 are as defined above; - - - - - is an optional double bond; X' is H, OR15 or NHR15, wherein R15 is H, alkyl, aryl, COalkyl, COaryl, CONHalkyl, CONHaryl, $SO_3H$, $SO_2$alkyl, $SO_2$aryl, $SO_2N(R14)_p$, $PO_3H_2$, COCH(R20)$NH_2$, $(CH_2)_{n'}$—NH—R14, C(=NH)NHR21, $(CH_2)_mCO_2H$, $(CH_2)_mSO_3H$, $(CH_2)_mNH_2$, $(CH_2)_mNHC(=NH)NH_2$, $(CH_2)_m$—C(=NH)$NH_2$, alkylNHalkyl, alkylNalkyl, $alkylN(alkyl)_2$, $alkylNH_2$, $alkylNHCO_2alkyl$ or Silylalkyl; wherein p, n', R14, R21 and m are as defined above; R4' is H, alkyl or aryl; R13 is halogen, $N(CH_3)_2$, OR15', NHR15' or COR15', wherein R15' is defined as is R15 and is identical or different from R15; or

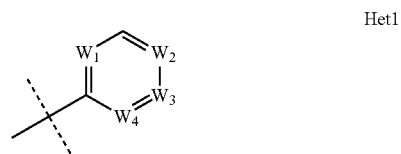

Het1

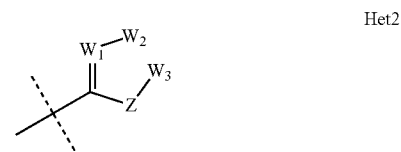

Het2

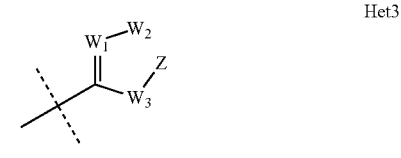

Het3

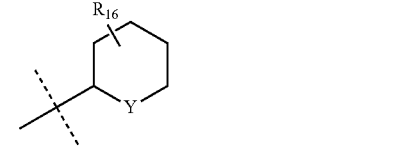

Het4

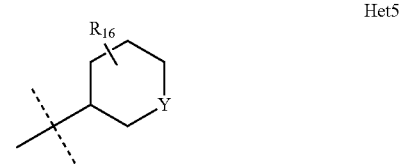

Het5

-continued

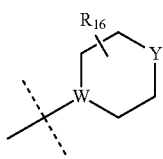

Het6 wherein W, W1, W2, W3, W4 are identical or different and are N or CH or CR16; R16 is H, alkyl, aryl, NHR15' or OR15', wherein R15' is as defined above; Y is $CH_2$, NH, N-alkyl, N—COalkyl, N—COaryl, N—$SO_2$alkyl, N—$SO_2$aryl, NH—C(=NH)$NH_2$, N—$CO_2$alkyl or N—$CO_2$aryl; and Z is NH, NR15', S or O, wherein R15' is as defined above; wherein the compound of formula 2.0 is not dihydrosolacongestidine, pregnan-3β-ol-20-amine, pregnan-3β-ol-20-(N,N-dimethylamino)propyl)amine or pregnane-3,20-diol; or

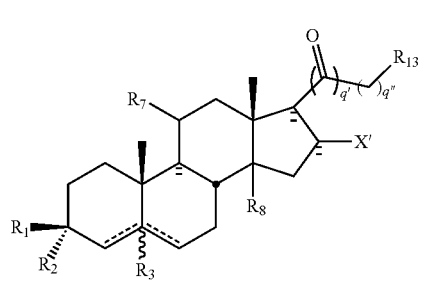

(3.0)

wherein R1, R2, R3, R7, R8, R13 and X' are as defined above; - - - - is an optional double bond; and q' and q" are identical or different and are 0-1; wherein the compound of formula 3.0 is not pregnanolone, pregnan-3β-ol-20-(aminopropyl)amine, pregnan-3β-ol-20-(aminobutyl)amine or O-t-butyldimethylsilylpregnanolone; or

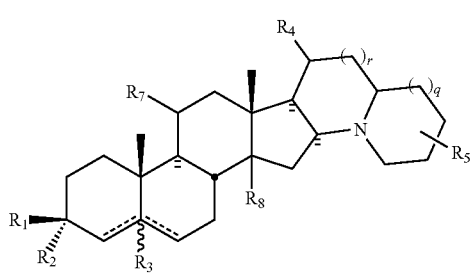

(4.0)

wherein R1, R2, R3, R4, R5, R7, R8 are as defined above; - - - - - is an optional double bond; r is 0-5; and q is 0-5, wherein the compound of formula 4.0 is not demissidine; or

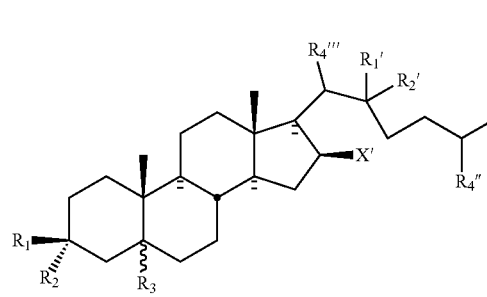

(5.0)

wherein R1, R2, R3 and R12 are as defined above; R4" and R4'" are identical or different and are H or $CH_3$; R1' and R2' are identical or different and are H, OH, Oalkyl or NHalkyl; and X' is as defined above; or a salt, stereoisomer or any mixture of stereoisomers of the compound of formula 1.0, 2.0, 3.0, 4.0 or 5.0.

In a specific embodiment, the compound is of formula 1.0 and
(i) R1 is OR12 or H;
(ii) R2 is OR12 or H;
(iii) R3 is H;
(iv) R4 is an alkyl;
(v) R5 is H;
(vi) R6 is an alkyl;
(vii) R7 is H;
(viii) R8 is H;
(ix) n is 1;
(x) X is O;
(xi) Y is NR19;
(xii) there is no double bond; or
(xiii) any combination of (i) to (xii).

In another specific embodiment, the compound is of formula 1.0 and
(xiv) R1 is OR12 and R2 is H;
(xv) R3 is H;
(xvi) R4 is CH3;
(xvii) R5 is H;
(xviii) R6 is CH3;
(xix) R7 is H;
(xx) R8 is H;
(xxi) n is 1;
(xxii) X is O;
(xxiii) Y is NR19;
(xxiv) there is no double bond; or
(xxv) any combination of (xiv) to (xxiv).

In another specific embodiment, the compound is of formula 1.0 and R3 is H, R4 is alkyl, R5 is H, R6 is alkyl, R7 is H, R8 is H, n is 1, X is O, Y is NR19 or $N^+R(R19)$(R19') and there is no double bond. In another specific embodiment, Y is NR19. In another specific embodiment, R1 is H, R2 is OR12, R4 is $CH_3$ and R6 is $CH_3$. In another specific embodiment, R1 is OR12, R2 is H, R4 is $CH_3$ and R6 is $CH_3$. In another specific embodiment, R12 is $SO_3H$ and R19 is H. In another specific embodiment, R12 is $PO_3H_2$ and R19 is H. In another specific embodiment, R12 is $(CH_2)_m$—$CO_2H$, m is 1 and R19 is H. In another specific embodiment, R12 is $(CH_2)_mNH_2$, m is 2 and R19 is H. In another specific embodiment, R12 is alkyl, and R19 is H. In another specific embodiment, R12 is $(CH_2)_mNHC(=NH)NH_2$, m is 2 and R19 is H. In another specific embodiment, 1 is NH2 and R2 is H or R1 is H and R2 is NH2R4 is $CH_3$, R6 is $CH_3$, and R19 is H. In another specific embodiment, R12 is a $CH_3OCH_2$ and R19 is H.

In another specific embodiment, R12 is H and R19 is COH. In another specific embodiment, R12 is COalkyl, and R19 is COH. In another specific embodiment, COalkyl is $COCH_3$. In another specific embodiment, there is provided a methanesulfonate salt of a compound of the present invention wherein R12 is H and R19 is H. In another specific embodiment, there is provided a citrate salt of a compound of the present invention, wherein R12 is H and R19 is H. In another specific embodiment, R1 and R2 together form =O, R4 is $CH_3$ and R6 is $CH_3$ and R19 is (C=O)H. In another specific embodiment, R1 and R2 together form =O, R4 is $CH_3$, R6 is $CH_3$ and R19 is H. In another specific embodiment, there is provided a hydrochloride salt of a compound of the present invention. In another specific embodiment, R12 is an alkyl and R19 is COH. In another specific embodiment, the alkyl is —CH$_2$—CH=CH$_2$. In another specific embodiment, 12 is an alkyl and R19 is H. In another specific embodiment. In another specific embodiment, the alkyl is —CH$_2$—CH=CH$_2$. In another specific embodiment, there is provided a hydrochloride salt of a compound of the present invention. In another specific embodiment, there is provided the compound is of formula 1.1:

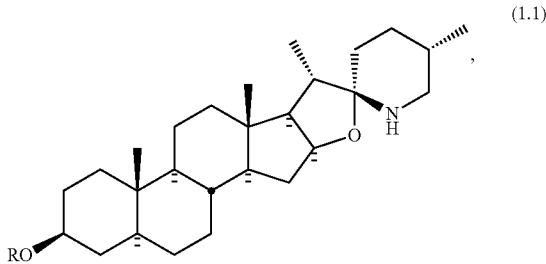

(1.1)

wherein R is defined as R12 in claim 1.

In another specific embodiment, the compound is of formula 2.0 and
(xxvi) R1 is OR12;
(xxvii) R2 is H;
(xxviii) R3 is H or absent;
(xxix) R7 is H;
(xxx) R8 is H;
(xxxi) X' is H or OR15;
(xxxii) there is no double bond; or
(xxxiii) any combination of (xxvi) to (xxxii).

In another specific embodiment, the compound is of formula 2.0 and:
(xxxiv) R1 is OR12;
(xxxv) R2 is H;
(xxxvi) R3 is H or absent;
(xxxvii) R4' is alkyl or aralkyl
(xxxviii) R7 is H;
(xxxix) R8 is H;
(xl) X' is H or OR15;
(xli) there is no double bond; or
(xlii) any combination of (xxxiv) to (xli).

In another specific embodiment, the compound is of formula 2.0 and R1 is OR12, R2 is H, R3 is H or absent, R7 is H, R8 is H, X' is H or OR15. In another specific embodiment, R3 is H. In another specific embodiment, R4' is alkyl. In another specific embodiment, R4' is CH$_3$. In another specific embodiment, R12 is H. In another specific embodiment, X' is H, there is no double bond and R13 is of formula Het1. In another specific embodiment, W1, W2 and W3 are CH, W4 is N and R16 is H. In another specific embodiment, X' is H, there is no double bond and R13 is of formula Het2. In another specific embodiment, W1 is N, W2 and W3 are CH, Z is S and R16 is H. In another specific embodiment, X' is H, there is no double bond and R13 is of formula Het4. In another specific embodiment, Y is NH and R16 is H. In another specific embodiment, X' is OR15, there is no double bond and R13 is of formula Het4. In another specific embodiment, R15 is CH$_3$, Y is NH and R16 is H. In another specific embodiment, R3 is absent, R4' is alkyl, X' is H, R12 is COalkyl, R13 is NHR15, and there is a double bond. In another specific embodiment, R3 is H, R4' is alkyl, X' is H, R12 is H, R13 is NHR15, and there is no double bond. In another specific embodiment, R4' is CH$_3$, R12 is COCH$_3$ and R15 is aryl. In another specific embodiment, the aryl is benzyl. In another specific embodiment, R4' is CH$_3$, R12 is COCH$_3$ and R15 is alkylN(alkyl)$_2$. In another specific embodiment, R15 is (CH$_2$)$_3$—N(CH$_3$)$_2$. In another specific embodiment, R4' is CH$_3$. In another specific embodiment, R3 is H, R4' is alkyl, X' is H, R12 is COalkyl, R13 is NHR15, and there is no double bond. In another specific embodiment, R3 is H, R4' is alkyl, X' is H, R12 is H, R13 is NHR15, and there is no double bond. In another specific embodiment, R4' is CH$_3$, R12 is COCH$_3$. In another specific embodiment, R15 is alkylNHCO$_2$alkyl. In another specific embodiment, R15 is (CH$_2$)$_2$—NHCO$_2$C(CH$_3$)$_3$. In another specific embodiment, R15 is (CH$_2$)$_3$—NHCO$_2$C(CH$_3$)$_3$. In another specific embodiment, R15 is (CH$_2$)$_4$—NHCO$_2$C(CH$_3$)$_3$. In another specific embodiment, R15 is alkylNHCO$_2$alkyl. In another specific embodiment, R15 is (CH$_2$)$_2$—NHCO$_2$C(CH$_3$)$_3$. In another specific embodiment, R15 is (CH$_2$)$_3$—NHCO$_2$C(CH$_3$)$_3$. In another specific embodiment, R15 is (CH$_2$)$_4$—NHCO$_2$C(CH$_3$)$_3$. In another specific embodiment, R15 is (CH$_2$)$_m$NH$_2$. In another specific embodiment, R15 is (CH$_2$)$_2$NH$_2$. In another specific embodiment, there is provided a hydrochloride salt of the compound of the present invention. In another specific embodiment, X' is H, R13 is OR15 and there is no double bond. In another specific embodiment, R15 is H.

In another specific embodiment, the compound is of formula 3.0 and:
(xliii) R1 is OR12;
(xliv) R2 is H;
(xlv) R3 is H;
(xlvi) R7 is H;
(xlvii) R8 is H;
(xlviii) X' is H; or
(xlix) any combination of (xliii) to (xlviii).

In another specific embodiment, R1 is OR12, R2 is H, R3 is H, R7 is H, R8 is H, X' is H and there is no double bond. In another specific embodiment, R12 is H. In another specific embodiment, q' and q" are 0. In another specific embodiment, R12 is Si(CH$_3$)$_2$C(CH$_3$)$_3$. In another specific embodiment, q' and q" are 0. In another specific embodiment, R13 is of formula Het3. In another specific embodiment, R13 is of formula Het3. In another specific embodiment, W1 is N, W2 and W3 are CH and Z is S. In another specific embodiment, W1 is N, W2 and W3 are CH and Z is NH. In another specific embodiment, W1 is N, W2 is CR16, W3 is CH and Z is S. In another specific embodiment, R16 is NH$_2$. In another specific embodiment, there is provided a hydrochloride salt of the compound of the present invention. In another specific embodiment, R12 is Si(CH$_3$)$_2$C(CH$_3$)$_3$. In another specific embodiment, W1 is N, W2 is CR16, W3 is CH and Z is S. In another specific embodiment, R16 is NH$_2$. In another specific embodiment, q' and q" are 1. In another specific embodiment, q' and q" are 1. In another specific embodiment, R13 is N(CH$_3$)$_2$. In another specific embodiment, R13 is Het6. In another specific embodiment, W is N, Y is CH and R16 is H. In another specific embodiment, W is N, Y is NH and R16 is H. In another specific embodiment, there is provided a hydrochloride salt of a compound of the present invention. In another specific embodiment, R13 is NHCH$_3$. In another specific embodiment, there is provided a hydrochloride salt of the compound of the present invention. In another specific embodiment, R13 is halogen. In another specific embodiment, the halogen is bromium.

In another specific embodiment, the compound is of formula 4.0 and
(l) R1 is OR12;
(li) R2 is H;

(lii) R3 is H;
(liii) R7 is H;
(liv) R8 is H;
(lv) R12 is H;
(lvi) there is no double bond; or
(lvii) any combination of (l) to (lvi).

In another specific embodiment, the compound is of formula 5.0 and:
(lviii) R1 is OR12;
(lix) R2 is H;
(lx) R3 is H;
(lxi) R4" is H or $CH_3$;
(lxii) R4'" is H or $CH_3$;
(lxiii) X' is H or OR15;
(lxiv) any combination of (lviii) to (lxiii).

In another specific embodiment, the compound is of formula 5.0 and R1 is OR12, R2 is H, R3 is H, R4" is H or $CH_3$, R4'" is H or $CH_3$, and X' is H or OR15.

In another specific embodiment, wherein R4" and R4'" are $CH_3$. In another specific embodiment, R12 is H. In another specific embodiment, X' is OH and R1' and R2' are H.

In accordance with another aspect, there is provided a compound of the formula 1.0, 2.0, 3.0 or 5.0 as defined herein or a salt, stereoisomer or any mixture of stereoisomers of such compound.

In accordance with another aspect, there is provided a compound as listed in Table 11 below or a salt, stereoisomer or any mixture of stereoisomers of such compound. In accordance with another embodiment, there is provided a compound as listed in Table 11 below which has a moderate to strong potentiation activity and or a moderate to strong antibacterial activity or a salt, stereoisomer or any mixture of stereoisomers of such compound.

Compositions

In accordance with another aspect of the present invention, there is provided a composition comprising the compound as defined above, and (a) an antibiotic; (b) an antiseptic; (c) a disinfectant; (d) a diluent; (e) an excipient; (f) a pharmaceutically acceptable carrier; or (g) any combination of (a)-(f).

In accordance with another aspect of the present invention, there is provided a composition comprising (A) (i) the compound of formula 1.0, 2.0, 3.0, 4.0 or 5.0 as defined herein; (ii) tomatidine; (iii) demissidine; (iv) solasodine; (v) 3α-hydroxytomatidine; (vi) 3-oxo-tomatidine; (vii) pregnanolone; (viii) pregnan-3β-ol-20-amine; (ix) pregnan-3β-ol-20-((N,N-dimethylamino)propyl)amine; (x) pregnan-3β-ol-20-(aminopropyl)amine; (xi) pregnan-3β-ol-20-(aminobutyl)amine; (xii) O-t-butyldimethylsilylpregnanolone; (xiii) pregnane-3,20-diol; (xiv) dihydrosolacongestidine; or (xv) a salt, stereoisomer or any mixture of stereoisomers of any one of (ii) to (xiv); and (B) (a) an antibiotic; (b) an antiseptic; (c) a disinfectant; (d) any combination of (a)-(c).

In a specific embodiment of the composition, said composition is a pharmaceutical composition.

In accordance with another aspect of the present invention, there is provided a composition comprising a combination of: (i) the compound as defined above; and (ii) an aminoglycoside antimicrobial agent. In a specific embodiment of the composition, the composition further comprises (iii) an antiseptic; (iv) a disinfectant; (v) a diluent; (vi) an excipient; (vii) a pharmaceutically acceptable carrier; or (viii) any combination of (iii)-(viii).

In a specific embodiment of the composition, the aminoglycoside antimicrobial agent is amikacin, gentamicin, kanamycin, streptomycin or tobramycin. In a specific embodiment of the composition, the composition further comprises a beta-lactam antimicrobial agent. In a specific embodiment of the composition, the composition comprises a compound of the formula 1.0, 2.0, 3.0 or 5.0 as defined herein or a salt, stereoisomer or any mixture of stereoisomers of such compound. In another specific embodiment of the composition, the composition comprises a compound as listed in Table 11 below or a salt, stereoisomer or any mixture of stereoisomers of such compound. In accordance with yet another embodiment, the composition comprises a compound as listed in Table 11 below which has a moderate to strong potentiation activity and or a moderate to strong antibacterial activity or a salt, stereoisomer or any mixture of stereoisomers of such compound.

Methods

In accordance with another aspect of the present invention, there is provided a method of preventing or treating a microbial infection in a subject, wherein said microbial infection is caused by an electron transport-deficient microbe, said method comprising administering to said subject a therapeutically effective amount of a compound or a composition comprising the compound and a pharmaceutically acceptable carrier, the compound being: (i) of formula 1.0, 2.0, 3.0, 4.0 or 5.0 as defined herein; (ii) tomatidine; (iii) demissidine; (iv) solasodine; (v) 3α-hydroxytomatidine; (vi) 3-oxo-tomatidine; (vii) pregnanolone; (viii) pregnan-3β-ol-20-amine; (ix) pregnan-3β-ol-20-((N,N-dimethylamino)propyl)amine; (x) pregnan-3β-ol-20-(aminopropyl)amine; (xi) pregnan-3β-ol-20-(aminobutyl)amine; (xii) O-t-butyldimethylsilylpregnanolone; (xiii) pregnane-3,20-diol; (xiv) dihydrosolacongestidine; or (xv) a salt, stereoisomer or any mixture of stereoisomers of any one of (ii) to (xiv), whereby said bacterial infection is prevented or treated.

In accordance with another aspect of the present invention, there is provided a method of preventing or treating a microbial infection in a subject, wherein said microbial infection is caused by an electron transport-deficient microbe, said method comprising administering to said subject a therapeutically effective amount of a compound or a composition comprising the compound and a pharmaceutically acceptable carrier, the compound being: (i) of formula 1.0, 2.0 or 3.0 as defined above; (ii) tomatidine; (iii) demissidine; (iv) solasodine; or (v) dihydrosolacongestidine, whereby said bacterial infection is prevented or treated.

In accordance with another aspect of the present invention, there is provided a method of disinfecting and/or sterilizing an object of an electron transport-deficient microbe, said method comprising applying an effective amount of the compound as defined above or of a composition comprising said compound to said object. In a specific embodiment of the method, said object is an animal, an animal tissue, animal cells, a synthetic material or a natural material.

In a specific embodiment of the methods, the electron transport-deficient microbe is an electron transport-deficient bacterium.

In another specific embodiment of the methods, the electron transport-deficient microbe is an intracellular bacteria. In another specific embodiment of the methods, the electron transport-deficient microbe is a bacterial small-colony variant (SCV). In another specific embodiment of the methods, the SCV is a coagulase-positive or -negative *staphylococci*, an enterococci, a *streptococci* of group A, a *streptococci* of group B, a *streptococci* of the viridans group, a *streptococci* of the mitis group, a *Bacillus* spp., a *Listeria* spp., a Corynebacterium, a Lactobacillus or a Gardnerella. In another specific embodiment of the methods, SCV is of the Firmicutes phylum. In another specific embodiment of the methods, the SCV of the Firmicutes phylum is a *Bacillus* spp. or a *Listeria* spp. In another specific embodiment of the methods, the SCV is a *Bacillus subtilis*, a *Bacillus cereus* or a *Listeria monocytogenes*. In another specific embodiment of the methods, the SCV is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Enterococcus faecium, Enterococcus faecalis, Enterococcus hirae, Enterococcus gallinarum, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the methods, the electron transport-deficient microbe is a *staphylococci*. In another specific embodiment of the methods, the *staphylococci* is an antibiotic-resistant *Staphylococcus*. In another specific embodiment of the methods, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the methods, the *staphylococci* is a *Staphylococcus aureus*. In another specific embodiment of the methods, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the methods, the electron transport-deficient microbe is an anaerobe bacterium. In another specific embodiment of the methods, the anaerobe is a *Clostridium*, a *Peptostreptococcus*, a *Peptococcus*, or a *Propionibacterium*. In another specific embodiment of the methods, the electron transport-deficient microbe is a *Clostridium*. In another specific embodiment of the methods, the *Clostridium* is *Clostridium perfringens* or *Clostridium difficile*. In another specific embodiment of the methods, the electron transport-deficient microbe is a facultative anaerobic bacterium grown in the absence of oxygen. In another specific embodiment of the methods, the electron transport-deficient microbe is a bacterium that is affected by another microorganism producing at least one electron transport inhibitor. In another specific embodiment of the methods, the electron transport-deficient microbe is a bacterium that is affected by another organism producing inhibitors of the electron transport chain. In another specific embodiment of the methods, the organism producing inhibitors of the electron transport chain is *Pseudomonas aeruginosa* or any other microorganism found in polymicrobic infections and producing electron transport inhibitors. In another specific embodiment of the methods, polymicrobic infections are infections of the airways in cystic fibrosis patients, hospital-acquired pneumonia, and infections associated with burns, catheters, and endotracheal tubes.

In accordance with another aspect of the present invention, there is provided a method of preventing or treating a microbial infection caused by a bacterial pathogen in a subject, said method comprising administering to said subject a therapeutically effective amount of the compound or composition as defined above, in combination with an aminoglycoside antimicrobial agent.

In accordance with another aspect of the present invention, there is provided a method of disinfecting and/or sterilizing an object of a bacterial pathogen, said method comprising applying an effective amount of the compound as defined above or of a composition comprising the compound, in combination with an aminoglycoside antimicrobial agent to said object.

In accordance with another aspect of the present invention, there is provided a method of preventing or treating a polymicrobial infection involving at least one microorganism that produces at least one electron transport inhibitor in a subject, said method comprising administering to said subject a therapeutically effective amount of the compound or composition as defined herein, whereby said polymicrobial infection is prevented or treated. In a specific embodiment, the polymicrobial infection involving at least one microorganism that produces at least one electron transport inhibitor comprises *Pseudomonas aeruginosa*. In another specific embodiment, the electron transport inhibitor is a 4-hydroxy-2-alkylquinoline or an analogue thereof. In another specific embodiment, the subject has cystic fibrosis. In another specific embodiment, the subject has an polymicrobic hospital-acquired pneumonia or a polymicrobic infection associated with a burn, a catheter, or an endotracheal tube.

In another specific embodiment of the methods, said object is an animal, an animal tissue, animal cells, food (e.g., packaged food preparation, meat, milk, milk products, etc.), a synthetic material or a natural material. In another specific embodiment of the methods, the bacterial pathogen is an intracellular bacterium. In another specific embodiment of the methods, the bacterial pathogen is a coagulase-positive or -negative *staphylococci*, a *streptococci* of group A, a *streptococci* of group B, a *streptococci* of the viridans group, a *streptococci* of the mitis group, a *Bacillus* spp., a *Listeria* spp., a *Corynebacterium*, a *Lactobacillus* or a *Gardnerella*. In another specific embodiment of the methods, the bacterial pathogen is of the Firmicutes phylum. In another specific embodiment of the methods, the bacterial pathogen of the Firmicutes phylum is a *Bacillus* spp. or a *Listeria* spp. In another specific embodiment of the methods, the bacterial pathogen is a *Bacillus subtilis*, a *Bacillus cereus* or a *Listeria monocytogenes*. In another specific embodiment of the methods, the bacterial pathogen is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the methods, the bacterial pathogen is a *staphylococci*. In another specific embodiment of the methods, the *staphylococci* is an antibiotic-resistant *Staphylococcus*. In another specific embodiment of the methods, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the methods, the *staphylococci* is a *Staphylococcus aureus*. In another specific embodiment of the methods, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the methods, the aminoglycoside antimicrobial agent is amikacin, gentamicin, kanamycin, streptomycin or tobramycin. In another specific embodiment of the methods, the methods further comprise a beta-lactam antibiotic. In another specific embodiment of the methods, said infection is a pulmonary infection, a mammary gland infection, a skin and soft tissue infection, a septicemia, a polymicrobic hospital-acquired pneumonia, or a polymicrobic infection associated with a burn, a catheter, or an endotracheal tube.

In accordance with yet another aspect of the present invention there is provided a method for reducing the development of resistance toward aminoglycosides in a bacteria, or treating a bacteria resistant to aminoglycoside in a subject, said method comprising administering to said subject a therapeutically effective amount of the compound or composition as defined herein, whereby said development of resistance toward aminoglycosides in a bacteria is prevented or said bacteria resistant to aminoglycoside is treated. In a specific embodiment, said infection is a pulmonary infection, a mammary gland infection, a skin and soft tissue infection, a septicemia, a polymicrobic hospital-acquired pneumonia, or a polymicrobic infection associated with a burn, a catheter, or an endotracheal tube.

In another specific embodiment of the methods, said subject or object is food, a cow or a human. In another specific embodiment of the methods, said subject is a human.

In a specific embodiment of the methods above, the compound is of the formula 1.0, 2.0, 3.0 or 5.0 as defined herein or a salt, stereoisomer or any mixture of stereoisomers of such compound. In another specific embodiment of the methods, the compound is one listed in Table 11 below or a salt, stereoisomer or any mixture of stereoisomers of such compound. In accordance with yet another embodiment of the method, the compound is one listed in Table 11 below which has a moderate to strong potentiation activity and or a moderate to strong antibacterial activity or a salt, stereoisomer or any mixture of stereoisomers of such compound.

Uses

In accordance with another aspect of the present invention, there is provided a use of the compound as defined above or of a composition comprising the compound, for: (a) preventing or treating a microbial infection in a subject, wherein said microbial infection is caused by an electron transport-deficient microbe; or (b) the disinfection, sterilization and/or antisepsis of an object from a an electron transport-deficient microbe.

In accordance with another aspect of the present invention, there is provided a use of the compound as defined above or of a composition comprising the compound, in the manufacture of a medicament for: (a) preventing or treating a microbial infection in a subject, wherein said microbial infection is caused by an electron transport-deficient microbe; or (b) the disinfection, sterilization and/or antisepsis of an object from a an electron transport-deficient microbe.

In a specific embodiment of the uses, said object is an animal, an animal tissue, animal cells, food (e.g., packaged food preparation, meat, milk, milk products, etc.), a synthetic material or a natural material. In another specific embodiment of the uses, the electron transport-deficient microbe is an electron transport-deficient bacterium. In another specific embodiment of the uses, the electron transport-deficient microbe is an intracellular bacterium. In another specific embodiment of the uses, electron transport-deficient microbe is a bacterial small-colony variant (SCV). In another specific embodiment of the uses, the SCV is a coagulase-positive or -negative *staphylococci*, an enterococci, a *streptococci* of group A, a *streptococci* of group B, a *streptococci* of the viridans group, a *streptococci* of the mitis group, a *Bacillus* spp., a *Listeria* spp., a *Corynebacterium*, a *Lactobacillus* or a *Gardnerella*. In another specific embodiment of the uses, the SCV is of the Firmicutes phylum. In another specific embodiment of the uses, the SCV of the Firmicutes phylum is a *Bacillus* spp. or a *Listeria* spp. In another specific embodiment of the uses, the SCV is a *Bacillus subtilis*, a *Bacillus cereus* or a *Listeria monocytogenes*. In another specific embodiment of the uses, the SCV is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Enterococcus faecium, Enterococcus faecalis, Enterococcus hirae, Enterococcus gallinarum, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the uses, the electron transport-deficient microbe is a *staphylococci*. In another specific embodiment of the uses, the *staphylococci* is an antibiotic-resistant *Staphylococcus*. In another specific embodiment of the uses, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the uses, the *staphylococcus* is a *Staphylococcus aureus*. In another specific embodiment of the uses, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the uses, the electron transport-deficient microbe is an anaerobe bacterium. In another specific embodiment of the uses, the anaerobe is a *Clostridium*, a *Peptostreptococcus*, a *Peptococcus*, or a *Propionibacterium*. In another specific embodiment of the uses, the electron transport-deficient microbe is a *Clostridium*. In another specific embodiment of the uses, the *Clostridium* is *Clostridium perfringens* or *Clostridium difficile*. In another specific embodiment of the uses, the electron transport-deficient microbe is a facultative anaerobic bacterium grown in the absence of oxygen. In another specific embodiment of the uses, the electron transport-deficient microbe is a bacterium that is affected by another microorganism producing at least one electron transport inhibitor. In another specific embodiment of the uses, the electron transport-deficient microbe is a bacterium that is affected by another organism producing inhibitors of the electron transport chain. In another specific embodiment of the uses, the organism producing inhibitors of the electron transport chain is *Pseudomonas aeruginosa* or any other microorganism found in polymicrobic infections and producing electron transport inhibitors. In another specific embodiment of the uses, polymicrobic infections is an infection of the airways of a cystic fibrosis subject, hospital-acquired pneumonia, and infections associated with burns, catheters, and endotracheal tubes.

In accordance with another aspect of the present invention, there is provided a use of the compound as defined above or of a composition comprising the compound, in combination with an aminoglycoside antimicrobial agent, for: (a) preventing or treating a bacterial pathogen infection in a subject; or (b) the disinfection, sterilization and/or antisepsis of an object from a bacterial pathogen.

In accordance with another aspect of the present invention, there is provided a use of the compound as defined above or of a composition comprising the compound, in combination with an aminoglycoside antimicrobial agent, in the manufacture of a medicament for: (a) preventing or treating a bacterial pathogen infection in a subject; or (b) the disinfection, sterilization and/or antisepsis of an object from a bacterial pathogen.

In accordance with another aspect of the present invention, there is provided a use of the compound as defined herein or of a composition comprising the compound, for: (a) preventing or treating a polymicrobial infection involving at least one microorganism that produces at least one electron transport inhibitor; or (b) the disinfection, sterilization and/or antisepsis of an object from a the polymicrobial infection. In a specific embodiment, the polymicrobial infection involving at least one microorganism that produces at least one electron transport inhibitor comprises *Pseudomonas aeruginosa*. In another specific embodiment, the electron transport inhibitor is a 4-hydroxy-2-alkylquinoline or an analogue thereof. In another specific embodiment, the polymicrobial infection is an infection of the airways of a cystic fibrosis subject. In another specific embodiment, the polymicrobial infection is a polymicrobic hospital-acquired pneumonia or a polymicrobic infection associated with a burn, a catheter, or an endotracheal tube.

In another specific embodiment of the uses, said object is an animal, an animal tissue, animal cells, a synthetic material or a natural material. In another specific embodiment of the uses, the bacterial pathogen is an intracellular bacterium. In another specific embodiment of the uses, the bacterial pathogen is a coagulase-positive or -negative *staphylococci*, *streptococci* of group A, *streptococci* of group B, a *streptococci* of the viridans group, a *streptococci* of the mitis group, a *Bacillus* spp., a *Listeria* spp., a *Corynebacterium*, a *Lactobacillus* or a *Gardnerella*. In another specific embodiment of the uses, the bacterial pathogen is of the Firmicutes phylum. In another specific embodiment of the uses, the bacterial pathogen of the Firmicutes phylum is a *Bacillus* spp. or a *Listeria* spp. In another specific embodiment of the uses, the bacterial pathogen is a *Bacillus subtilis*, a *Bacillus cereus* or a *Listeria monocytogenes*. In another specific embodiment of the uses, the bacterial pathogen is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the uses, the bacterial pathogen is a *staphylococci*. In another specific embodiment of the uses, the *staphylococci* is an antibiotic-resistant *Staphylococcus*. In another specific embodiment of the uses, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the uses, the *staphylococci* is a *Staphylococcus aureus*. In another specific embodiment of the uses, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the uses, the aminoglycoside antimicrobial agent is amikacin, gentamicin, kanamycin, streptomycin or tobramycin. In another specific embodiment of the uses, the uses further comprise a beta-lactam antibiotic.

In accordance with yet another aspect of the present invention there is provided a use use of the compound as defined herein or of a composition comprising the compound, for: (a) for reducing the development of resistance toward aminoglycosides in a bacteria, or treating a bacteria resistant to aminoglycoside in a subject.

In another specific embodiment of the uses, said infection is a pulmonary infection, a mammary gland infection, a skin and soft tissue infection, a septicemia, a polymicrobic hospital-acquired pneumonia, or a polymicrobic infection associated with a burn, a catheter, or an endotracheal tube. In another specific embodiment of the uses, said subject or object is food, a cow or a human. In another specific embodiment of the uses, said subject is a human.

In a specific embodiment of the uses above, the compound is of the formula 1.0, 2.0, 3.0 or 5.0 as defined herein or a salt, stereoisomer or any mixture of stereoisomers of such compound. In another specific embodiment of the uses, the compound is one listed in Table 11 below or a salt, stereoisomer or any mixture of stereoisomers of such compound. In accordance with yet another embodiment of the uses, the compound is one listed in Table 11 below which has a moderate to strong potentiation activity and or a moderate to strong antibacterial activity or a salt, stereoisomer or any mixture of stereoisomers of such compound.

Compounds for Use

In accordance with another aspect of the present invention, there is provided a compound as defined above or of a composition comprising the compound, for: (a) preventing or treating a microbial infection in a subject, wherein said microbial infection is caused by an electron transport-deficient microbe; or (b) the disinfection, sterilization and/or antisepsis of an object from an electron transport-deficient microbe.

In accordance with another aspect of the present invention, there is provided a compound use of the compound as defined herein or of a composition comprising the compound, for (a) preventing or treating a polymicrobial infection involving at least one microorganism that produces at least one electron transport inhibitor; or (b) the disinfection, sterilization and/or antisepsis of an object from a the polymicrobial infection. In a specific embodiment, the polymicrobial infection involving at least one microorganism that produces at least one electron transport inhibitor comprises *Pseudomonas aeruginosa*. In another specific embodiment, the electron transport inhibitor is a 4-hydroxy-2-alkylquinoline or an analogue thereof. In another specific embodiment, the polymicrobial infection is an infection of the airways of a cystic fibrosis subject. In another specific embodiment, the polymicrobial infection is a polymicrobic hospital-acquired pneumonia or a polymicrobic infection associated with a burn, a catheter, or an endotracheal tube.

In a specific embodiment of the compound for use, said object is an animal, an animal tissue, animal cells, food (e.g., packaged food preparation, meat, milk, milk products, etc.), a synthetic material or a natural material. In another specific embodiment of the compound for use, the electron transport-deficient microbe is an electron transport-deficient bacterium. In another specific embodiment of the compound for use, the electron transport-deficient microbe is an intracellular bacterium. In another specific embodiment of the compound for use, the electron transport-deficient microbe is a bacterial small-colony variant (SCV). In another specific embodiment of the compound for use, the SCV is a coagulase-positive or -negative *staphylococci*, an enterococci, a *streptococci* of group A, a *streptococci* of group B, a *streptococci* of the viridans group, a *streptococci* of the mitis group, a *Bacillus* spp., a *Listeria* spp., a *Corynebacterium*, a *Lactobacillus* or a *Gardnerella*. In another specific embodiment of the compounds for use, the SCV is of the Firmicutes phylum. In another specific embodiment of the compounds for use, the SCV of the Firmicutes phylum is a *Bacillus* spp. or a *Listeria* spp. In another specific embodiment of the compounds for use, the SCV is a *Bacillus subtilis*, a *Bacillus cereus* or a *Listeria monocytogenes*. In another specific embodiment of the compound for use, the SCV is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Enterococcus faecium, Enterococcus faecalis, Enterococcus hirae, Enterococcus gallinarum, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the compound for use, the electron transport-deficient microbe is a *staphylococci*. In another specific embodiment of the compound for use, the *staphylococci* is an antibiotic-resistant *Staphylococcus*. In another specific embodiment of the compound for use, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the compound for use, the *staphylococcus* is a *Staphylococcus aureus*. In another specific embodiment of the compound for use, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the compound for use, the electron transport-deficient microbe is an anaerobe bacterium. In another specific embodiment of the compound for use, the anaerobe is a *Clostridium*, a *Peptostreptococcus*, a *Peptococcus*, or a *Propionibacterium*. In another specific embodiment of the compound for use, the electron transport-deficient microbe is a *Clostridium*. In another specific embodiment of the compound for use, the *Clostridium* is *Clostridium perfringens* or *Clostridium difficile*. In another specific embodiment of the compound for use, the electron transport-deficient microbe is a facultative anaerobic bacterium grown in the absence of oxygen. In another specific embodiment of the compound for use, the electron transport-deficient microbe is a bacterium that is affected by another microorganism producing at least one electron transport inhibitor. In another specific embodiment of the compound for use, the electron transport-deficient microbe is a bacterium that is affected by another organism producing inhibitors of the electron transport chain. In another specific embodiment of the compound for use, the organism producing inhibitors of the electron transport chain is *Pseudomonas aeruginosa* or any other microorganism found in polymicrobic infections and producing electron transport inhibitors. In another specific embodiment of the compound for use, polymicrobic infections are infections of the airways in a cystic fibrosis patient, hospital-acquired pneumonia, and infections associated with burns, catheters, and endotracheal tubes.

In accordance with another aspect of the present invention, there is provided a compound as defined in above or of a composition comprising the compound, in combination with an aminoglycoside antimicrobial agent for: (a) preventing or treating a microbial infection in a subject, wherein said microbial infection is caused by a bacterial pathogen; or (b) the disinfection, sterilization and/or antisepsis of an object from a bacterial pathogen.

In another specific embodiment of the compound for use, said object is an animal, an animal tissue, animal cells, food, a synthetic material or a natural material. In another specific embodiment of the compound for use, the bacterial pathogen is an intracellular bacterium. In another specific embodiment of the compound for use, the bacterial pathogen is a coagulase-positive or -negative *staphylococci*, a *streptococci* of group A, a *streptococci* of group B, a *streptococci* of the viridans group, a *streptococci* of the mitis group, a *Bacillus* spp., a *Listeria* spp., a *Corynebacterium*, a *Lactobacillus* or a *Gardnerella*. In another specific embodiment of the compounds for use, the bacterial pathogen is of the Firmicutes phylum. In another specific embodiment of the compounds for use, the bacterial pathogen of the Firmicutes phylum is a *Bacillus* spp. or a *Listeria* spp. In another specific embodiment of the compounds for use, the bacterial pathogen is a *Bacillus subtilis*, a *Bacillus cereus* or a *Listeria monocytogenes*. In another specific embodiment of the compound for use, the bacterial pathogen is a *Staphylococcus aureus, Staphylococcus intermedius, Staphylococcus epidermidis, Staphylococcus haemolyticus, Staphylococcus hyicus, Staphylococcus chromogenes, Staphylococcus stimulans, Staphylococcus saprophyticus, Staphylococcus hominis, Staphylococcus lugdunensis, Staphylococcus capitis, Streptococcus pneumoniae, Streptococcus pyogenes, Streptococcus mitis, Streptococcus agalactiae, Streptococcus dysgalactiae, Streptococcus uberis, Streptococcus suis, Streptococcus bovis, Streptococcus intermedius, Bacillus subtilis, Bacillus anthracis, Bacillus cereus, Bacillus coagulans, Listeria monocytogenes* or *Listeria ivanovii*. In another specific embodiment of the compound for use, the bacterial pathogen is a *staphylococci*. In another specific embodiment of the compound for use, the *staphylococci* is an antibiotic-resistant *Staphylococcus*. In another specific embodiment of the compound for use, the *staphylococci* is a *Staphylococcus aureus*, a *Staphylococcus epidermidis*, a *Staphylococcus haemolyticus*, a *Staphylococcus saprophyticus*, or a *Staphylococcus hominis*. In another specific embodiment of the compound for use, the *staphylococci* is a *Staphylococcus aureus*. In another specific embodiment of the compound for use, said *staphylococci* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA). In another specific embodiment of the compound for use, the aminoglycoside antimicrobial agent is amikacin, gentamicin, kanamycin, streptomycin or tobramycin. In another specific embodiment of the compound for use, the composition further comprises a beta-lactam antibiotic.

In accordance with yet another aspect of the present invention there is provided a compound for use or a composition comprising the compound for use, for: (a) for reducing the development of resistance toward aminoglycosides in a bacteria, or treating a bacteria resistant to aminoglycoside in a subject.

In another specific embodiment of the compound for use, said infection is a pulmonary infection, a mammary gland infection, a skin and soft tissue infection, a septicemia, a polymicrobic hospital-acquired pneumonia, or a polymicrobic infection associated with a burn, a catheter, or an endotracheal tube. In another specific embodiment of the compound for use, said subject or object is food, a cow or a human. In another specific embodiment of the compound for use, said subject is a human.

In a specific embodiment of the compounds for use above, the compound is of the formula 1.0, 2.0, 3.0 or 5.0 as defined herein or a salt, stereoisomer or any mixture of stereoisomers of such compound. In another specific embodiment of the compounds for use, the compound is one listed in Table 11 below or a salt, stereoisomer or any mixture of stereoisomers of such compound. In accordance with yet another embodiment of the compounds for use, the compound is one listed in Table 11 below which has a moderate to strong potentiation activity and or a moderate to strong antibacterial activity or a salt, stereoisomer or any mixture of stereoisomers of such compound.

Screening Methods

In accordance with another aspect of the present invention, there is provided a method of identifying a pathogen, the microbial infection of which is treatable by the compound as defined above or a composition comprising the compound, said method comprising contacting said bacterial pathogen with said compound or composition and determining the effect of said compound or composition on the growth or survival of said pathogen, wherein a decrease in the growth or survival of said pathogen in the presence as compared to in the absence of said compound or composition is an indication that said bacterial pathogen is treatable by said compound or composition.

Kits

In accordance with another aspect of the present invention, there is provided a kit comprising the compound defined above or the above-mentioned composition, and instructions to use same in the prevention or treatment of a bacterial infection.

In a specific embodiment of the kit, the kit comprises: (i) one or more compounds defined above; and/or (ii) one or more compositions defined above, and instructions to use same in the prevention or treatment of a microbial infection. In another specific embodiment of the kit, the kit further comprises (iii) an antiseptic; (iv) a disinfectant; (v) a diluent; (vi) an excipient; (vii) a pharmaceutically acceptable carrier; or (viii) any combination of (iii)-(vii). In another specific embodiment of the kit, the kit comprises: (a) an antibiotic; (b) an antiseptic; (c) a disinfectant; (d) any combination of (a)-(c).

More specifically, in accordance with another aspect of the present invention, there is provided a kit comprising the compound as defined above, and instructions to use same in (a) the prevention or treatment of a microbial infection; or (b) the disinfection, sterilization and/or antisepsis of an object.

In a specific embodiment of the kit, the kit further comprises an aminoglycoside antimicrobial agent. In another specific embodiment of the kit, the aminoglycoside antimicrobial agent is amikacin, gentamicin, kanamycin, streptomycin or tobramycin. In another specific embodiment of the kit, the kit further comprises a beta-lactam antimicrobial agent.

In a specific embodiment of the kits above, the compound is of the formula 1.0, 2.0, 3.0 or 5.0 as defined herein or a salt, stereoisomer or any mixture of stereoisomers of such compound. In another specific embodiment of the kits, the compound is one listed in Table 11 below or a salt, stereoisomer or any mixture of stereoisomers of such compound. In accordance with yet another embodiment of the kits, the compound is one listed in Table 11 below which has a moderate to strong potentiation activity and or a moderate to strong antibacterial activity or a salt, stereoisomer or any mixture of stereoisomers of such compound.

In a specific embodiment of the method, use and compositions for uses of the present invention, said subject is an animal (e.g., cattle such as cow; goat, ewe, ass, horse, pig, cat, dog, etc.). In another specific embodiment, said subject is a cow. In another specific embodiment, said subject is a human.

Other advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A displays pictures of samples (10 μl) from bacterial cultures treated with various concentrations of tomatidine for 48 h in the Brain Hearth Infusion (BHI) medium at 35° C. and spotted on agar plated. FIGS. 1B and 1C show the effect of tomatidine (TO), tomatine (TN) (for CF07-S only), erythromycin (ERY) or ciprofloxacin (CIP) on the growth and viability of the normal non electron transport-deficient strain CF07-L and of the electron transport-deficient SCV strain CF07-S, respectively. Concentrations of 16 μg/ml of TO (n=3), 0.5 μg/ml of ERY (n=3) and 1.0 μg/ml of CIP (n=3) were used against CF07-L (FIG. 1B), whereas concentrations of 0.25 μg/ml of TO (n=4), 16 μg/ml of TN (n=3), 0.25 μg/ml of ERY (n=3) and 0.5 μg/ml of CIP (n=2) were used against the SCV strain CF07-S (FIG. 10). The no drug control experiments (Ctrl) are from 4 independent experiments (n=4).

In FIG. 3A, the effect of control antibiotics at approximately 4×MIC (four times their minimal inhibitory concentration (MIC)) on the biosynthesis of proteins (chloramphenicol (CHL), DNA (Norfloxacin (NOR)), RNA (Rifampicin (RIF)) and cell wall peptidoglycan synthesis (Vancomycin (VAN)) was evaluated for the normal strain ATCC 29213. FIG. 3B shows the effect of TO at 125 µg/ml on the biosynthesis of the same four macromolecules in ATCC 29213. FIG. 3C shows the effect of different concentrations of TO on the biosynthesis of the same four macromolecules in ATCC 29213 in the presence of HQNO at 20 µg/ml. Significant decreases of the biosynthesis of proteins in comparison to the three others are indicated (*, P<0.05, one-way ANOVA with Dunnett's post test for A and B and two-way ANOVA with a Bonferroni's post test for C). Results are from three independent experiments and are expressed as percentages of incorporation of radiolabeled molecules by untreated (FIG. 3A), DMSO-treated (FIG. 3B) or HQNO-treated bacteria (FIG. 3C). Data are presented as means with standard deviations.

FIG. 4A presents infection levels of polarized CF airway epithelial cells with the normal strain CF07-L and the SCV strain CF07-S, 24 and 48 h post-internalization (*, P<0.05; two-way ANOVA with the Bonferroni's post test). Results are from 2 to 3 independent experiments performed in duplicate. In FIG. 4B, CF07-S cells treated with 1.25 and 12.5 µg/ml of tomatidine contained significantly less SCVs than DMSO-treated cells 48 h post-internalization. Data are from 3 independent experiments performed in duplicate. Significant differences in comparison to the control are shown (, P<0.01; *, P<0.001; one-way ANOVA with a Dunnett's post test). Data are presented as means with standard deviations.

FIG. 5A shows a broth inoculated with the normal strain CF07-L grown in absence (−) or presence (+) of 4 µg/ml of gentamicin or 0.12 µg/ml of TO. FIG. 5B shows a broth inoculated with the SCV strain CF07-S grown in absence (−) or presence (+) of 4 µg/ml of gentamicin or 0.12 µg/ml of TO. FIG. 5C shows a broth inoculated with both the normal strain CF07-L and the SCV CF07-S grown in absence (−) or presence (+) of 4 µg/ml of gentamicin and/or 0.12 µg/ml of TO.

DESCRIPTION OF ILLUSTRATIVE EMBODIMENTS

Figure 1A:
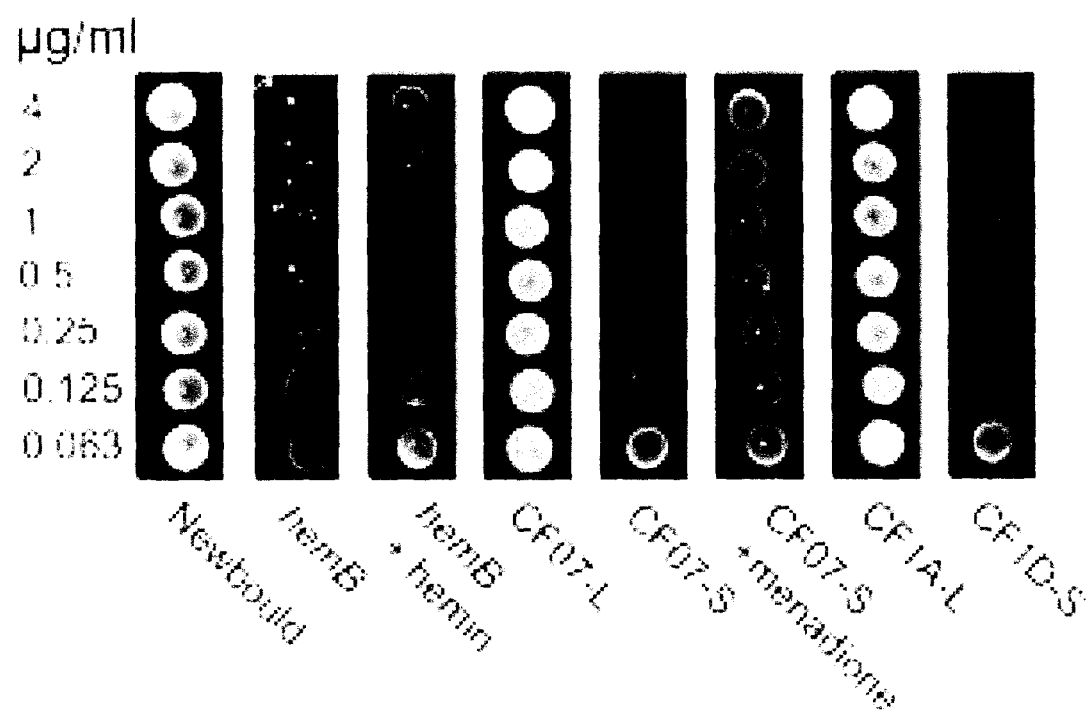
FIGS. 1A-C show the effect of various compounds, including tomatidine, on the growth of *S. aureus*.

Antimicrobial Activity of Compounds of the Present Invention

In certain embodiments, the present invention relates to the unexpected discovery that compounds of the present invention may have a very potent growth inhibitory activity against electron transport-deficient microbes whereas the growth of normal non electron transport-deficient bacterial strains is not significantly altered by compounds of the present invention. The action of compounds of the present invention on electron transport-deficient microbes is bacteriostatic and without being bound by this theory, seems to results from the inhibition of the biosynthesis of macromolecules and more specifically protein biosynthesis. Furthermore, the action of compounds of the present invention have the ability to target intracellular bacteria, i.e., to reach and act on bacteria even if they are present into a host cell. Thus, the antimicrobial activity of compounds of the present invention against electron transport-deficient microbes is clinically relevant (i.e., requires minimal amounts of compound for potency) and is also effective against intracellular pathogenic bacteria. The clinical use of the compounds of the present invention may thus help to selectively defeat difficult-to-treat and relapsing bacterial infections caused by extracellular or intracellular electron transport-deficient microbes.

The present invention also encompasses using a compound of the present invention with another active ingredient (e.g., another anibiotic agent).

Potentiating Activity of Compounds of the Present Invention

In other embodiments, the present invention hence also relates to the surprising discovery that compounds of the present invention may selectively potentiate the inhibitory activity of aminoglycoside antimicrobial agents against normal (i.e. non electron transport-deficient (e.g., non-SCVs)) bacteria) such as Staphylococcus spp. This potentiating action may be efficient against clinical isolates that are not antibiotic resistant, but also against antibiotic resistant bacteria such as methicillin-resistant Staphylococcus aureus (MRSA), aminoglycoside-resistant S. aureus and multi-resistant S. aureus. As aminoglycoside antimicrobial agents are currently used in clinic to treat, among others, staphylococcal infections, the use of compounds of the present invention in order to increase the potency of aminoglycoside-based antimicrobial therapies may be useful in human and veterinary medicine. In addition to increasing the potency of aminoglycoside-based therapies, compounds of the present invention used in combination with aminoglycosides may also reduce the development of resistance to aminoglycosides in bacteria. The present invention thus also relates to the use of at least one compound of the present invention in combination with an aminoglycoside antimicrobial agent to improve the antibiotic efficacy of the aminoglycoside (i.e., to create a synergy and to reduce the development of resistance) in a therapeutic approach that selectively treat or prevent bacterial infections in subjects in need thereof.

Antimicrobial Activity of Compounds of the Present Invention in Polymicrobic Infections In accordance with yet a further embodiment, the present invention relates to the surprising discovery that compounds of the present invention may have a very potent growth inhibitory activity against normal (i.e. non electron transport-defective bacteria (e.g., non SCV *Staphylococcus* spp.)) when such bacteria are present in a polymicrobic community comprising at least one organism producing at least one inhibitor of the electron transport chain (e.g., *Pseudomonas aeruginosa*). The clinical use of compounds of the present invention, used alone or in combination with other active ingredients, may thus help to selectively defeat difficult-to-treat and relapsing polymicrobic bacterial infections.

DEFINITIONS

The use of the word "a" or "an" when used in conjunction with the term "comprising" in the claims and/or the specification may mean "one" but it is also consistent with the meaning of "one or more", "at least one", and "one or more than one".

As used herein the term "microbe" includes without being limited to a bacterium.

As used here in the term "infection" refers to a monomicrobic or a polymicrobic infection. It refers to infections involving at least one microbial target of the present invention (e.g., an electron transport-deficient bacteria (SCVs, anaerobes, etc.), a bacterial pathogen targeted by aminoglycoside). In a particular embodiment, such bacteria are of the Firmicutes phylum. Without being so limited, infections targeted by the compounds of the present invention includes food-borne infections, an infection of the airways of cystic fibrosis patients, hospital-acquired pneumonia, or an infection associated with burns, implantation of catheter, or endotracheal tube, etc.

As used herein the terms "polymicrobic infection" are interchangable with the terms "mixed infection", "co-infection" or "polymicrobial infection". As used herein, they refer to a co-culture, an infection, a colonization, a community or a population of microbes of different species or strains found together either as planktonic organisms or embedded in a biofilm structure. More particularly, polymicrobic infections targeted by compounds of the present invention include at least one microorganism (e.g., bacteria) producing at least one electron transport inhibitor (e.g., *Pseudomonas aeruginosa* (Lightbown and Jackson, 1956; Machan et al., 1992; Mitchell et al., 2010b; Voggu et al., 2006)) and/or at least one molecule related to 4-hydroxy-2-alkylquinolines produced by certain microorganisms (e.g., bacteria) (e.g., *Burkholderia* species (Vial et al., 2008)). Without being so limited, such polymicrobic infections may be found in any pathologic situation where *staphylococci* and *P. aeruginosa* co-infect a same host (e.g., cystic fibrosis and hospital-acquired infections (e.g., pneumonia and infections associated with burns, catheters, and endotracheal tubes)) (Chastre and Fagon, 2002; Harlid et al., 1996; Harrison, 2007; Hoffman et al., 2006).

The use of the word "bacterium" in this specification and claim(s) may be interchanged with the words "bacteria", "bacterial pathogen", "infectious agent", "strain" or "bacterial strain" (e.g., living either as planktonic microorganism, embedded in a biofilm structure or intracellular).

As used herein the terms "reducing the development of resistance" toward an antimicrobial agent (e.g., aminoglycoside) refers to a reduction in the number of bacteria that become resistant to the antimicrobial agent when treated with the antimicrobial agent in combination with a compound of the present invention as compared to when treated with the antimicrobial agent alone. As used herein the term "reduce", "reduction" or "decrease" or "prevention" of development of resistance toward an antimicrobial agent refers to a reduction in development of resistance toward an antimicrobial agent of at least 10% as compared to reference (e.g., treatment with antimicrobial agent alone) development of resistance, in an embodiment of at least 20% lower, in a further embodiment of at least 30%, in a further embodiment of at least 40%, in a further embodiment of at least 50%, in a further embodiment of at least 60%, in a further embodiment of at least 70%, in a further embodiment of at least 80%, in a further embodiment of at least 90%, in a further embodiment of 100% (complete prevention).

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Compound

As used herein, the terms "molecule", "compound" and "agent" are used interchangeably and broadly to refer to natural, synthetic or semi-synthetic molecules or compounds. The term "compound" therefore denotes, for example, chemicals, macromolecules, cell or tissue extracts (from plants or animals) and the like. Non-limiting examples of compounds include peptides, antibodies, carbohydrates, nucleic acid molecules and pharmaceutical agents. The compound can be selected and screened by a variety of means including random screening, rational selection and by rational design using, for example, ligand modeling methods such as computer modeling. As will be understood by the person of ordinary skill, molecules having non-naturally occurring modifications are also within the scope of the term "compound". For example, the compounds of the present invention can be modified to enhance their activity, stability, and/or bioavailability, and also to lower its toxicity. The compounds or molecules identified in accordance with the teachings of the present invention have a therapeutic value in diseases or conditions related to microbial infections.

As used herein the term "aryl" refers to substituted or unsubstituted aryl (e.g., C5-C6), wherein the substituent, if any, is an halide, OH, OMe, $NO_2$, $NH_2$ or $CO_2H$, including heterocycles. Het cycles 1 (het1), 2 (het2) and 3 (het 3) defined herein are also examples of aryls.

As used herein the term "alkyl" refers to saturated or unsaturated (e.g., allyle), substituted or unsubstituted, linear or branched alkyl (C1 to 010), wherein the substituent is an halide, OH, OMe, $NO_2$, $NH_2$ or $CO_2H$. Without being so limited, it includes —$CH_2$—CH=$CH_2$, and —$(CH_2)_3$—CH$(CH_3)CH_2$.

As used herein the term "aralkyl" refers to a radical derived from an alkyl radical by replacing one or more hydrogen atoms by aryl groups. It includes saturated or unsaturated, substituted or unsubstituted, linear or branched aralkyl (C1 to C10), comprising wherein the substituent is an halide, OH, OMe, $NO_2$, $NH_2$ or $CO_2H$.

As used herein the term « CO » refers to a carbonyl.

As used herein the term "aminoglycoside" refers to an aminoglycoside antimicrobial agent and include without being so limited to amikacin, arbekacin, gentamicin, kanamycin, dideoxykanamycin, neomycin, neamine, lividomycin, butirosin, netilmicin, paromomycin, rhodostreptomycin, streptomycin, tobramycin, framycetin, ribostamycin, bekanamycin, dibekacin, hygromycin B, sisomicin, isepamicin, verdamicin, astromicin, apramycin, fortimycin, sorbistin, kasugamycin, istamycin, sagamicin, spectinomycin and other known aminoglycosides. The term aminoglycoside also includes herein the 4,5-disubstituted deoxystreptamines, 4,6-disubstituted deoxystreptamines, aminocyclitols, streptidines, actinanimes, deoxystreptamines, destomycins. It also includes neoglycosides or "next-generation aminoglycosides" (e.g., plazomycin, ACHN-490) namely aminoglycosides able to circumvent bacterial resistance mechanisms used against previous aminoglycosides.

As used herein the term "combination" when used in reference to the use of the compound of the invention in combination with at least one other antibiotic (e.g., aminoglycoside) means i) simultaneously (e.g., in separate compositions or a single composition); ii) simultaneously as a single dual action compound (e.g., a conjugate of the two or more, the compound of the invention chemically linked with at least another antibiotic) in a single composition; or iii) subsequently (e.g., in separate compositions wherein the compound of the present invention is administered before (e.g., immediately before) or after (e.g., immediately after) the at least other antibiotic).

The present invention encompasses therefore the use of a combination of two, three or more active ingredients including at least one compound of the present invention. A combination of three compounds in accordance of the present invention can include a compound of the present invention, an aminoglycoside and a beta-lactam (e.g., Ubrolexin™ (i.e. cephalexin and kanamycin)).

Microbial Targets

Compounds of the present invention may be used as antimicrobial agents. In this respect, the compounds of the present invention are used against "electron transport-deficient microbes". As used herein the term "electron transport-deficient microbes" refers for example to SCVs that have a defect in the electron transport chain, to bacteria that are facultative anaerobes but that are grown in anaerobic environments, to bacteria that naturally have a low redox-potential electron transport (e.g., anaerobes) and to bacteria of a polymicrobic infection that have been affected by at least one electron transport inhibitor and/or at least one molecule related to 4-hydroxy-2-alkylquinolines produced by at least one microorganism (e.g., bacteria) (e.g., *Pseudomonas aeruginosa*, *Burkholderia* species) or also present in the infection. In a specific embodiment, the electron transport-deficient microbe is a gram positive bacteria.

SCVs may have a defect in the electron transport chain caused by mutation, sub-optimal expression, sub-optimal biosynthesis or alteration of electron transport proteins, necessary coenzymes, cofactors or precursors, a defect in the bacterial $F_0F_1$-ATPase or proton pumps or an overall reduction of certain metabolic pathways such as the tricarboxilic cycle that ultimately affects and reduces electron transport. SCVs of a variety of bacterial species of human or animal origins are thus microbial targets of the compounds of the present invention. The microbial species include but are not limited to coagulase-positive and -negative *staphylococci* such as *S. aureus*, *S. intermedius*, *S. epidermidis*, *S. haemolyticus*, *S. hyicus*, *S. chromogenes*, *S. stimulans*, *S. saprophyticus*, *S. hominis*, *S. lugdunensis*, *S. capitis* as well as *Micrococcus luteus*. Also targeted are the enterococci (such as *E. faecium*, *E. faecalis*, *E. hirae*, *E. gallinarum*), the streptococci of group A, of group B, of the viridans group, of the mitis group, such as *Streptococcus pneumoniae*, *S. pyogenes*, *S. mitis*, *S. agalactiae*, *S. dysgalactiae*, *S. uberis*, *S. suis*, *S. bovis* and *S. intermedius*. Other SCV targets are from *Bacillus* spp., and *Listeria* spp. that include *Bacillus subtilis*, *Bacillus anthracis*, *Bacillus cereus*, *Bacillus coagulans*, *Listeria monocytogenes* and *Listeria ivanovii*, with also the inclusion of other bacterial genus like *Corynebacterium*, *Lactobacillus* and *Gardnerella*. The compounds of the present invention may be used against bacteria of the Firmicutes phylum. While there are currently more than 274 genera within the Firmicutes phylum, notable genera of Firmicutes include Bacilli, order Bacillales, *Bacillus*, *Listeria*, *Staphylococcus*, Bacilli, order Lactobacillales, *Enterococcus*, *Lactobacillus*, *Lactococcus*, *Leuconostoc*, *Pediococcus*, *Streptococcus*, Clostridia, *Acetobacterium*, *Clostridium*, *Eubacterium*, *Heliobacterium*, *Heliospirillum*, *Megasphaera*, *Pectinatus*, *Selenomonas*, *Zymophilus*, *Sporohalobacter*, *Sporomusa*, and Erysipelotrichi, *Erysipelothrix*.

Bacteria that can grow either in the presence or in absence of oxygen such as the facultative anaerobes (Ginnes and Stewart, 1996) are also microbial targets of the present invention. Such facultative anaerobe bacteria growing in an anaerobic environment are considered "electron transport-deficient microbes" since their electron transport chain is not functioning to the full potential in the absence of oxygen. For example, it has been shown that the membrane potential of the facultative anaerobe *S. aureus* grown anaerobically causes a substantial decrease of the electrical potential across the cytoplasmic membrane (Mates et al., 1983).

The terms "electron transport-deficient microbes" also refer to bacteria that naturally have a low redox-potential electron transport such as anaerobes. Such electron transport systems contain electron transport proteins with a low redox potential (ferridoxin-like and flavodoxin-like proteins) that allow energy production in the absence of oxygen. Anaerobes use fermentation or only parts of the Krebs' cycle and the electron transport system, which is leading to an energetic deficit in comparison to aerobic organism using their more complexed metabolic pathways (Black, 2008). Disease causing anaerobic bacteria such as of those of the *Clostridium* (e.g., *C. difficile*, *C. perfringens*, C, botulinum, *C. tetani*), *Peptococcus*, *Peptostreptococcus* and *Propionibacterium* genus can thus be considered to have a defective electron transport system generating a different membrane potential and are also microbial targets of the compounds of the present invention.

The term "electron transport-deficient microbes" also refers to bacteria of a polymicrobic infection that are affected by at least one electron transport inhibitor and/or at least one molecule related to 4-hydroxy-2-alkylquinolines produced by at least one microorganism (e.g., bacteria (e.g., *Pseudomonas aeruginosa, Burkholderia* species) also present in the infection.

In a specific embodiment, electron transport-deficient microbes according to the invention are SCVs. In another embodiment, electron transport-deficient microbes according to the invention are intracellular SCVs. In another more specific embodiment, electron transport-deficient microbes according to the invention are staphylococcal SCVs. In another embodiment, the electron transport-deficient microbe according to the invention is *Staphylococcus aureus* SCV, *Staphylococcus epidermidis* SCV, another coagulase-negative *staphylococci* SCV, *Bacillus subtilis* SCV, *Bacillus anthracis* SCV, *Bacillus cereus* SCV, *Bacillus coagulans* SCV, *Listeria monocytogenes* SCV or *Listeria ivanovii* SCV. In another specific embodiment electron transport-deficient microbes are anaerobic bacteria (e.g., *Clostridium* spp.). In another specific embodiment electron transport-deficient microbes are facultative anaerobic bacteria grown in anaerobic environments (e.g., *S. aureus*). In another specific embodiment, the electron transport-deficient microbe is a bacterium that is affected by another organism producing at list one inhibitor of the electron transport chain and/or at least one molecule related to a 4-hydroxy-2-alkylquinoline. In another specific embodiment, the organism producing at least one inhibitor of the electron transport chain is *Pseudomonas aeruginosa* or any other microorganism found in the polymicrobic infection and producing at least one electron transport inhibitor. In another specific embodiment, the polymicrobic infection is an infection of the airways of cystic fibrosis patients, hospital-acquired pneumonia, or an infection associated with burns, implantation of catheter, or endotracheal tube.

Compounds of the present invention may also be used as potentiators of antimicrobial agents. As used herein, the term "potentiator" in the context of an "antimicrobial agent potentiator" refers to an agent which increases the antimicrobial activity of another antimicrobial agent on a bacterium and thus creates a synergy, i.e., the activity of the combination of agents is superior to that observed for either agent individually.

In this respect, the compounds of the present invention may be used in combination with aminoglycosides against "normal" (i.e. non electron transport-deficient) bacterial targets of human or animal origins that include but are not limited to coagulase-positive and -negative *staphylococci* such as *S. aureus, S. intermedius, S. epidermidis, S. haemolyticus, S. hyicus, S. chromogenes, S. stimulans, S. saprophyticus, S. hominis, S. lugdunensis, S. capitis* as well as against *Micrococcus luteus*. Also targeted are the *streptococci* of group A, of group B, of the viridans group, of the mitis group, such as *S. pneumoniae, S. pyogenes, S. mitis, S. agalactiae, S. dysgalactiae, S. uberis, S. suis, S. bovis* and *S. intermedius*. Other bacterial targets of the compounds in combination with aminoglycosides are *Bacillus* spp., and *Listeria* spp. that include *Bacillus subtilis, Bacillus anthracis, Bacillus cereus, Bacillus coagulans, Listeria monocytogenes* and *Listeria ivanovii*, with also the inclusion of other bacterial genus like *Corynebacterium, Lactobacillus* and *Gardnerella*. In a specific embodiment, the non electron transport-deficient target of the compounds of the invention as potentiators of aminoglycosides is a gram positive bacteria.

In a particular embodiment, the compounds of the present invention are used as potentiators of aminoglycosides against normal staphylococcal strains (e.g., *Staphylococcus aureus, Staphylococcus epidermidis*) and other coagulase-negative *staphylococci* strains.

Subjects and Objects

As used herein the term "object" refers to an animal or to an animal tissue (e.g., skin, hands), an animal cells (e.g., in cell cultures for laboratory purpose or for use for administration to subjects), food (e.g., packaged food preparation, meat, milk, milk products, etc.), a synthetic material or a natural material. Synthetic materials include, without being so limited, working surfaces (e.g., table, counter), instruments, prosthetic devices and biomaterials. The term "Natural material" includes, without being so limited, skin grafts, tissue cultures and organs.

As used herein the term "subject" or "patient" refers to an animal, preferably a mammal such as but not limited to a human, cow, goat, ewe, ass, horse, pig, chicken, cat, dog, etc. who is the object of treatment, observation or experiment.

Excipients/Carriers

As used herein, the terms "pharmaceutically acceptable" refer to molecular entities and compositions that are physiologically tolerable and do not typically produce an allergic or similar untoward reaction, such as gastric upset, dizziness and the like, when administered to animals (e.g., cows, humans). Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin.

Routes of Administration

Compounds of the invention may be administered in a pharmaceutical composition. Pharmaceutical compositions may be administered in unit dosage form. Any appropriate route of administration may be employed, for example, transdermal (topical), parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation); transdermal (topical); transmucosal, and rectal administration.

Conventional pharmaceutical practice may be employed to provide suitable formulations or compositions to administer such compositions to patients. Methods well known in the art for making pharmaceutical compositions and formulations are found in, for example, Remington: The Science and Practice of Pharmacy, (20th ed.) ed. A. R. Gennaro A R., 2000, Lippincott: Philadelphia.

Formulations

Therapeutic formulations for oral administration, may be in the form of tablets or capsules; for transmucosal (e.g., rectal, intranasal) or transdermal/percutaneous administration may be in the form of ointments, powders, nasal drops, sprays/aerosols or suppositories; for topical administration, may be in the form of ointments, creams, gels or solutions; for parenteral administration (e.g., intravenously, intramuscularly, intradermal, intramammary, subcutaneously, intrathecally or transdermally), using for example injectable solutions. Furthermore, administration can be carried out sublingually or as ophthalmological preparations or as an aerosol, for example in the form of a spray. Intravenous, intramuscular or oral administration is a preferred form of use.

The pharmaceutical compositions of the present invention may also contain excipients/carriers such as preserving agents, solubilizing agents, stabilizing agents, wetting agents, emulsifiers, sweeteners, colorants, odorants, salts for the variation of osmotic pressure, buffers, coating agents or antioxidants. As mentioned earlier, they may also contain other therapeutically valuable agents.

Oral

For the purpose of oral therapeutic administration, the active compound can be incorporated with excipients and used for example in the form of tablets, troches, dragees, hard or soft gelatin capsules, solutions (e.g., syrups), aerosols, emulsions or suspensions, or capsules. For the preparation of formulations for oral administration, the compounds of the present invention may be admixed with pharmaceutically inert, inorganic or organic excipients (e.g., pharmaceutically compatible binding agents, and/or adjuvant). The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Examples of suitable excipients for tablets, dragees or hard gelatin capsules for example include lactose, maize starch or derivatives thereof, talc or stearic acid or salts thereof. Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

Nasal

For administration by inhalation, the compounds may be delivered in the form of an aerosol spray from pressured container or dispenser which contains a suitable propellant, e.g., a gas such as carbon dioxide, or a nebulizer. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Transmucosal or Transdermal (Topical)

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. For suppositories, and local or percutaneous application, excipients which may be used include for example natural or hardened oils, waxes, fats and semi-solid or liquid polyols.

Parenteral

Pharmaceutical compositions suitable for injectable use include sterile aqueous solutions (where water soluble) or dispersions and sterile powders for the extemporaneous preparation of sterile injectable solutions or dispersion. Solutions or suspensions used for parenteral application can include the following components: a sterile diluent such as water for injection (where water soluble), saline solution, fixed oils (e.g., paraffin oil), polyalkylene glycols such as polyethylene glycols, glycerine, propylene glycol or other synthetic solvents, oils of vegetable origin, or hydrogenated napthalenes; antibacterial agents such as benzyl alcohol or methyl parabens; antioxidants such as ascorbic acid or sodium bisulfite; chelating agents such as ethylenediaminetetraacetic acid; reducing agents such as dithiothreitol, buffers such as acetates, citrates or phosphates and agents for the adjustment of tonicity such as sodium chloride or dextrose. The pH can be adjusted with acids or bases, such as hydrochloric acid or sodium hydroxide. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. The parenteral preparation can also be enclosed in ampoules, disposable syringes or multiple dose vials made of glass or plastic.

For intravenous or intramammary administration, suitable carriers include physiological saline, bacteriostatic water, Cremophor ELTM (BASF, Parsippany, N.J.) or phosphate buffered saline (PBS).

Liposomal suspensions (including liposomes targeted to specific cell types) can also be used as pharmaceutically acceptable carriers. A variety of liposomal formulations suitable for delivering a compound to an animal have been described and demonstrated to be effective in delivering a variety of compound, including, e.g., small molecules, nucleic acids, and polypeptides.

As mentioned earlier, medicaments containing the compounds of the present invention are also an object of the present invention, as is a process for the manufacture of such medicaments, which process comprises bringing one or more of the compounds of the present invention to, if desired, one or more other therapeutically valuable substances into a galenical administration form.

Compounds

Protective Group

The compounds of the present invention may include protective groups. As used herein, and without being so limited, the term "protective group" is meant to refer to a substituent on a heteroatom that may be cleaved in specified reaction conditions to unmask the heteroatom and includes without being so limited tert-butoxycarbonyle (BOC), t-butyldimethylsilyl (TBDMS), methoxymethyl (MOM), etc. Further examples of protecting groups may be found in Protective groups in organic synthesis, 4th edition, Peter G. M. Wuts & Theodora W. Greene editors, Wiley 2007.

Salts, Esters, Hydrates and Solvates

The compounds of the present invention include pharmacologically acceptable salts and ester derivatives thereof as well as hydrates or solvates thereof and all stereoisomeric forms of the referenced compounds. The compounds and pharmacologically acceptable esters thereof of the present invention can form pharmacologically acceptable salts if necessary.

Salts

The terms "pharmacologically acceptable salt thereof" refer to a salt to which the compounds of the present invention can be converted. Preferred examples of such a salt include alkali metal salts such as a sodium salt, a potassium salt, a lithium salt, magnesium or calcium salts; alkaline earth metal salts such as a calcium salt and a magnesium salt; metal salts such as an aluminium salt, an iron salt, a zinc salt, a copper salt, a nickel salt and a cobalt salt; amine salts such as inorganic salts including an ammonium salt; organic salts or ammonium salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt and a tris(hydroxymethyl)aminomethane salt; inorganic acid salts such as hydrohalic acid salts such as a hydrofluoride, a hydrochloride, a hydrobromide or a hydroiodide, a nitrate, a perchlorate, a sulfate or a phosphate; lower alkanesulfonates such as a methanesulfonate (mesylate), trifluoromethanesulfonate or an ethanesulfonate; arylsulfonates such as a benzenesulfonate or a p-toluenesulfonate and the like, which are non toxic to living organisms; organic acid salts such as an acetate, a malate, adipate, a fumarate, a succinate, a citrate, alginate, ascorbate, benzoate, benzenesulfonate, bisulfate, butyrate, camphorate, camphorsulfonate, cinnamate, cyclopentanepropionate, digluconate, dodecylsulfate, ethanesulfonate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, sulfonate, methanesulfonate, trifluoromethanesulfonates, ethanesulfonates 2-naphthalenesulfonate, nicotinate, nitrate, oxalate, pamoate, pectinate, persulfate, 3-phenylpropionate, picrate, pivalate, propionate, tartrate, thiocyanate, tosylate, and undecanoate, a tartrate, an oxalate or a maleate; and amino acid salts such as a glycine salt, a lysine salt, an arginine salt, an ornithine salt, histidine, a glutamate or an aspartate salt. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others. For further example, see S. M. Berge, et al. "Pharmaceutical Salts," J. Pharm. Sci. 1977, 66, 1-19. Such salts can be formed quite readily by those skilled in the art using standard techniques.

More specific examples of the salts formed with an acidic group present in the compounds of the present invention include metal salts such as alkali metal salts (e.g., sodium salts, potassium salts and lithium salts), alkali earth metal salts (e.g., calcium salts and magnesium salts), aluminum salts and iron salts; amine salts such as inorganic amine salts (e.g., ammonium salts) and organic amine salts (e.g., t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts. N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

All salts are intended to be pharmaceutically acceptable salts within the scope of the invention and all salts are considered equivalent to the free forms of the corresponding compounds for purposes of the invention.

Esters

Physiologically/pharmaceutically acceptable esters are also useful as active medicaments. The term "pharmaceutically acceptable esters" embraces esters of the compounds of the present invention, in which hydroxy groups (e.g., in carboxylic acid) have been converted to the corresponding esters and may act as a prodrug which, when absorbed into the bloodstream of a warm-blooded animal, may cleave in such a manner as to release the drug form and permit the drug to afford improved therapeutic efficacy. Such esters can be formed with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms. Further examples are the esters with aliphatic or aromatic acids such as acetic acid or with aliphatic alcohol (e.g., alkyl esters, including methyl, ethyl, propyl, isopropyl, butyl, isobutyl or pentyl esters, and the like) or aromatic alcohols (e.g., benzyl ester).

Esters can be prepared from their corresponding acids or salts by a variety of methods known to those skilled in the art, such as, for example, by first transforming the acid to the acid chloride and then reacting the acid chloride with a suitable alcohol. Other suitable methods for making esters are described in Kemp and Vellaccio, 1980.

Where esters of the invention have a basic group, such as an amino group, the compound can be converted to a salt by reacting it with an acid, and in the case where the esters have an acidic group, such as a sulfonamide group, the compound can be converted to a salt by reacting it with a base. The compounds of the present invention encompass such salts.

Salts and esters of the compounds of the present invention may be prepared by known method by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis [dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of etherification of alcohols.

Hydrates

As used herein the terms, "pharmaceutically acceptable hydrate" refer to the compounds of the instant invention crystallized with one or more molecules of water to form a hydrated form.

Prodrugs and Solvates

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of the present invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention or a pharmaceutically acceptable salt, hydrate or solvate of the compound contains a carboxylic acid functional group, a prodrug can comprise an ester formed by the replacement of the hydrogen atom of the acid group with a group such as, for example, (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as 3-dimethylaminoethyl), carbamoyl-(C1-C2)alkyl, N,N-di(C1-C2)alkylcarbamoyl-(C1-C2)alkyl and piperidino-, pyrrolidino- or morpholino(C2-C3)alkyl, and the like.

Similarly, if a compound of the present invention contains an alcohol functional group, a prodrug can be formed by the replacement of the hydrogen atom of the alcohol group with a group such as, for example, (C1-C6)alkanoyloxymethyl, 1-((C1-C6)alkanoyloxy)ethyl, 1-methyl-1-((C1-C6)alkanoyloxy)ethyl, (C1-C6)alkoxycarbonyloxymethyl, N—(C1-C6)alkoxycarbonylaminomethyl, succinoyl, (C1-C6)alkanoyl, α-amino(C1-C4)alkanyl, arylacyl and α-aminoacyl, or α-aminoacyl-α-aminoacyl, where each α-aminoacyl group is independently selected from the naturally occurring L-amino acids, P(O)(OH)2, —P(O)(O(C1-C6)alkyl)$_2$ or glycosyl (the radical resulting from the removal of a hydroxyl group of the hemiacetal form of a carbohydrate), and the like.

If a compound of the present invention incorporates an amine functional group, a prodrug can be formed by the replacement of a hydrogen atom in the amine group with a group such as, for example, R-carbonyl, RO-carbonyl, NRR'-carbonyl where R and R' are each independently (C1-C10)alkyl, (C3-C7)cycloalkyl, benzyl, or R-carbonyl is a natural]-aminoacyl or natural β-aminoacyl, —C(OH)COOY1 wherein Y1 is H, (C1-C6)alkyl or benzyl, —C(OY2)Y3 wherein Y2 is (C1-C4) alkyl and Y3 is (C1-C6)alkyl, carboxy(C1-C6)alkyl, amino(C1-C4)alkyl or mono-N— or di-N,N—(C1-C6)alkylaminoalkyl, —C(Y4)Y5 wherein Y4 is H or methyl and Y5 is mono-N— or di-N,N—(C1-C6)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, MPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Stereoisomers, Diastereomers, Enantiomers, Racemates, Tautomers

The compounds of the present invention have asymmetric carbon atoms and can exist in the form of stereoisomers (e.g., diastereomers, optically pure enantiomers) or as racemates or mixtures of two or more stereoisomers of each compound. The term "compound" as used herein embraces all of these forms.

Diastereomers (sometimes called diastereoisomers) are stereoisomers that are not enantiomers. Diastereomerism occurs when two or more stereoisomers of a compound have different configurations at one or more (but not all) of the equivalent (related) stereocenters and are not mirror images of each other. When two diastereoisomers differ from each other at only one stereocenter they are epimers. Each stereocenter gives rise to two different configurations and thus to two different stereoisomers.

Diastereomers differ from enantiomers in that the latter are pairs of stereoisomers which differ in all stereocenters and are therefore mirror images of one another. Enantiomers of a compound with more than one stereocenter are also diastereomers of the other stereoisomers of that compound that are not their mirror image. Diastereomers have different physical properties and different reactivity, unlike enantiomers. Diastereomers of the present invention include tomatidine and 3-alpha-hydroxy-tomatidine for example.

For purposes of this Specification, "pharmaceutically acceptable tautomer" means any tautomeric form of any compound of the present invention.

The purification of enantiomers and the separation of isomeric mixtures of a compound of the present invention may be accomplished by standard techniques known in the art.

Dosages

The dosages in which the compounds of the present invention are administered in effective amounts depend on the nature of the specific active ingredient, the body weight, the age and the requirements of the patient and the mode of application. In general, daily dosages of about 1 mg-5000 mg, preferably 5 mg-500 mg, per day come into consideration.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the present invention can include a series of treatments.

Toxicity and Therapeutic Efficacy

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

The present invention also encompasses kits comprising the compounds of the present invention. For example, the kit can comprise one or more compounds inhibiting the growth of electron transport-deficient microbes (e.g., SCVs) or potentiating the antimicrobial activity of aminoglycoside antibiotics against normal bacterial strains (e.g., staphylococci). The kit may optionally include one or more control sample(s). The compounds or agents can be packaged in a suitable container. The kit can further comprise instructions for using the kit.

The present invention also relates to methods for preparing the above-mentioned compounds.

The present invention is illustrated in further details by the following non-limiting examples.

EXAMPLE 1

Antibacterial Activity of Tomatidine Against Electron Transport-Deficient *Staphylococcus aureus* Small-Colony Variants (SCVs) Measured with MIC Tomatidine (formula 1.1 wherein R is H) specifically and selectively inhibits the growth of *S. aureus* SCVs whereas it has no significant impact on the growth of normal *S. aureus* strains.

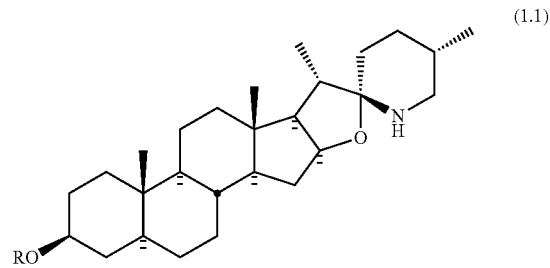

(1.1)

The symbols used herein to denote the orientation of the hydrogen atoms are those used in the tomatidine formula presented below at the left, wherein "=" denotes ⫶—H and "•" ⫶—H. They are used to identify the stereochemistry of tertiary carbons (having three direct neighbors other than hydrogens). The classical representation of the hydrogens is shown in the right for comparison purposes. Such convention is used to simplify the formulas.

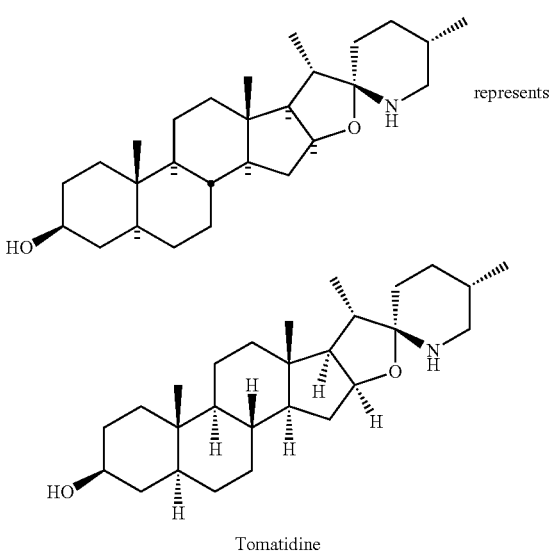

Tomatidine

Method:

The minimal inhibitory concentrations (MICs) (i.e. lowest concentration of an antimicrobial that will inhibit the visible growth of a microorganism after incubation), of tomatidine (formula 1.1 above, wherein R is H), tomatine (formula 1.2 below) and control antibiotics (gentamicin, vancomycin, erythromycin, ciprofloxacin and oxacillin) were determined against "normal" (i.e. non electron transport-deficient) (ATCC 29213, Newbould, CF07-L and CF1A-L) and electron transport-deficient SCV (NewbouldΔhemB, CF07-S and CF1D-S) *S. aureus* strains. Of note, CF07-L and CF07-S and CF1A-L and CF1D-S are genetically-related pairs of strains co-isolated from CF patients (Mitchell et al., 2010b) whereas Newbould is a laboratory strain of bovine origin (ATCC 29740). Results are reported in Table 1 below.

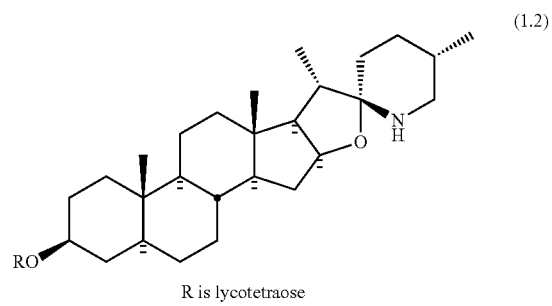

R is lycotetraose

Results:

Table 1 below shows that tomatidine's MIC against all SCVs was remarkably low (0.12 µg/ml) whereas no clinically significant MIC was measurable for normal strains. Also, no MIC was observed for tomatine, the lycotetraose-substituted derivative of tomatidine, against SCVs, which confirmed the specificity of the growth inhibitory activity of tomatidine against SCVs. MICs of gentamicin for the different strains were in accordance with the known decreased susceptibility of SCVs to aminoglycosides (Proctor et al., 2006). The MIC of erythromycin against the laboratory-derived SCV strain NewbouldΔhemB (>16 µg/ml) is explained by the insertion of the macrolide resistance gene ermA in the hemB gene of this strain to create the SCV phenotype (defective electron transport chain and respiratory deficiency) through inactivation of hemin biosynthesis (Brouillette et al., 2004). MICs obtained for the other control antibiotics were in the expected Clinical and Laboratory Standards Institute (CLSI) (2006) ranges and did not seem to vary significantly among strains. Briefly, MICs were determined using the microdilution method in 96-well microplates. Bacteria were inoculated at ~$10^5$-$10^6$ CFU/ml and incubated at 35° C. for 48 h in brain heart infusion (BHI) broth (BD, Mississauga, ON, Canada) in order to allow SCVs to reach maximal growth as previously described (Atalla et al., 2008; Mitchell et al., 2010b). Then $OD_{595\ nm}$ was read on a microplate reader. The MICs obtained against the quality control strain ATCC 29213 for all antibiotics tested were similar in BHI and in cation-adjusted Mueller-Hinton broth (CAMHB) (BD) showing that the type of cultivation medium did not influence results.

TABLE 1

Susceptibility (MIC in µg/ml) of normal and SCV *S. aureus* strains to tomatidine, tomatine and control antibiotics.

| Strain[a] | TO | TN | GEN | VAN | ERY | CIP | OXA |
|---|---|---|---|---|---|---|---|
| ATCC 29213 in BHI | >16 | >16 | 1 | 2 | 0.12-0.25 | 0.5 | 0.12-0.25 |
| ATCC 29213 in MHBCA | >16 | >16 | 0.5-1 | 1-2 | 0.12-0.5 | 0.5-1 | 0.12-0.5 |
| Newbould | >16 | >16 | 0.5-1 | 1 | 0.25 | 0.25-0.5 | 0.06-0.12 |
| NewbouldΔhemB | 0.12 | >16 | 4-8 | 2 | >16 | 0.12-0.25 | 0.03-0.06 |
| CF07-L | >16 | >16 | 1-2 | 2 | 0.25 | 0.5 | 0.06-0.12 |
| CF07-S | 0.12 | >16 | 8 | 2 | 0.12 | 0.12 | 0.06-0.12 |
| CF1A-L | >16 | >16 | 1-2 | 1-2 | 0.25 | 0.5 | 0.25 |
| CF1D-S | 0.12 | >16 | 8 | 2 | 0.12 | 0.12 | 0.06-0.12 |

[a]ATCC 29213, Newbould, CF07-L and CF1A-L are normal strains whereas NewbouldΔhemB, CF07-S and CF1D-S are SCVs.
TO: tomatidine, TN: tomatine, GEN: gentamicin, VAN: vancomycin, ERY: erythromycin, CIP: ciprofloxacin, OXA: oxacillin.

EXAMPLE 2

Antibacterial Activity of Tomatidine Against Electron Transport-Deficient *Staphylococcus aureus* Small-Colony Variants (SCVs) and Against the Anaerobic Bacterium *Clostridium perfringens* Measured with an Agar Diffusion Method Tomatidine (formula 1.1, wherein R is H) specifically and selectively inhibits the growth of all types of *S. aureus* SCVs whereas it has no significant impact on the growth of normal *S. aureus* strains. The growth of the anaerobic strain *C. perfringens* (also considered herein to be electron transport-deficient) is also inhibited by tomatidine.

Method:

The susceptibility of various *S. aureus* SCVs as well as of the anaerobe strain *Clostridium perfringens* ATCC 13124 to tomatidine was tested by an agar diffusion method. *S. aureus* strains SCV NewbouldΔhemB (hemin auxotroph), SCV CF07-S (menadione auxotroph), SCV CF6A-S (thymidine auxotroph), SCV CF41A-S (unknown auxotrophy), and strain *C. perfringens* ATCC 13124 were spread on the surface of Tryptic Soy agar plates and 50 µg of tomatidine diluted in DMSO was added to wells for diffusion. After incubation in aerobic conditions for *S. aureus* and anaerobic conditions for *C. perfringens* (using the Anaero pack system no. 10-01, Mitsubishi gas chemical co., Tokyo), the diameters of the zones of inhibition around the wells (for the DMSO control and for the tomatidine well) were measured and reported in mm in Table 2.

Results:

Table 2 shows the diameters of the zones of inhibition caused by tomatidine against various *S. aureus* SCVs as well as against an anaerobe, *C. perfringens*. Results show that all types of *S. aureus* SCVs, whether they are hemin (NewbouldΔhemB), menadione (CF07-S), thymidine (CF6A-S) or unknown auxotroph (CF41A-S), are all susceptible to the inhibitory action of tomatidine. This is also true for the *S. aureus* SCV strain CF6A-S which is multi-resistant to several antibiotics such as tobramycin (MIC>32 μg/ml), gentamicin (MIC>32 μg/ml) as well as trimetoprim (MIC>32 μg/ml). Also, as it did against the electron transport-deficient *S. aureus* SCVs, tomatidine caused a growth inhibition against the anaerobic strain *C. perfringens*, which naturally possess a low redox-potential electron transport.

TABLE 2

Diameters of the zone of inhibition (in mm) caused by tomatidine on a variety of *S. aureus* SCVs and against the anaerobic strain *C. perfringens*. Antibiotic effect of tomatidine on *Staphylococcus aureus* SCVs and *Clostridium perfringens*

| Organism | Strain | Auxo-trophy | Control (DMSO) | Tomatidine (50 μg) |
|---|---|---|---|---|
| | | | Diameter of inhibition zone (mm) | |
| *Staphylococcus aureus* | SCV NewbouldΔhemB | hemin | 0 | 23.5 |
| | SCV CF07S | menadione | 0 | 22.5 |
| | SCV CF6A-S | thymidine | 0 | 23.0 |
| | SCV CF41A-S | unknown | 0 | 21.5 |
| *Clostridium perfringens* | ATCC 13124 | | 6.5 | 11 |

*S. aureus* strains were incubated for 24 hours at 37° C. with $O_2$.
*C. perfringens* was incubated for 48 hours at 37° C. without $O_2$.

EXAMPLE 3

Effect of Inducing an Electron Transport Chain Defect in Normal *Staphylococcus aureus* Strains on their Susceptibility to Tomatidine The inhibition of electron transport by 4-hydroxy-2-heptylquinoline-N-oxide (HQNO), a known electron transport inhibitor (Hoffman et al., 2006; Mitchell et al, 2010b), sensitizes normal strains to tomatidine. This shows that tomatidine possesses a specific antibacterial activity against strains that have a defective electron transport system like SCVs.

Method:

The MICs of tomatidine, tomatine and control antibiotics (gentamicin, vancomycin, erythromycin, ciprofloxacin and oxacillin) were determined against the normal strains ATCC 29213 and CF07-L as well as against the SCV strain CF07-S in the presence of 20 μg HQNO/ml. Results are reported in Table 3 below. Also, the normal *S. aureus* strain CF07-L was inoculated at ~$10^5$-$10^6$ CFU/ml in BHI in absence or presence of HQNO and/or tomatidine at 20 μg/ml and 8 μg/ml, respectively. Cultures were incubated 48 h at 35° C./225 RPM and the growth was visually evaluated. Results are reported in FIG. 2.

Figure 2:
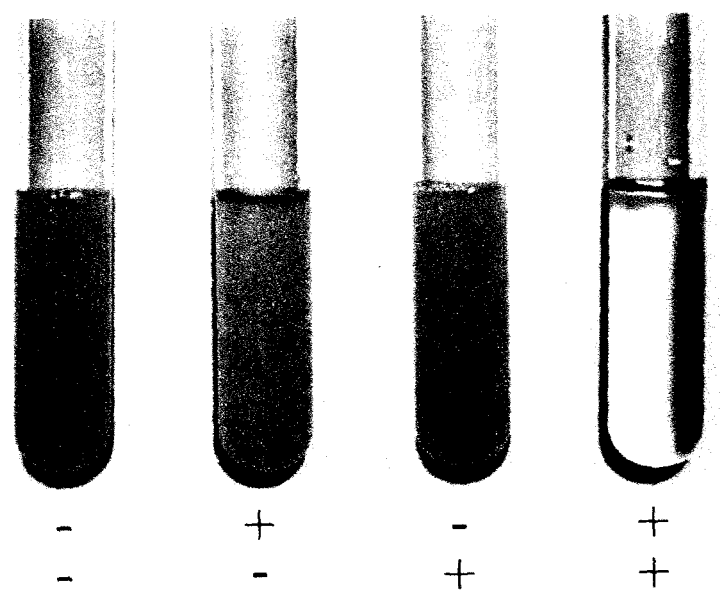
FIG. 2 shows the effect of TO and the inhibitor of the electron transport system 4-hydroxy-2-heptylquinoline-N-oxide (HQNO), each alone or in combination, on a culture of the normal *S. aureus* strain CF07-L. TO and HQNO were used at a concentration of 8 and 20 μg/ml, respectively.

Results:

As shown in Table 3 below, HQNO allowed tomatidine to inhibit the growth of normal strains as it does of SCVs. HQNO did not however alter the susceptibility of SCVs, which already have an altered electron transport, to tomatidine or any other antibiotic. HQNO increased resistance of normal strains to the aminoglycoside gentamicin (see also (Hoffman et al., 2006)), further supporting that the effect of HQNO on normal strains generates the SCV phenotype. FIG. 2 confirms that the combination of HQNO (20 μg/ml) and tomatidine (8 μg/ml) has an inhibitory activity on normal *S. aureus* strains and that this inhibitory activity is not observed with either of these molecules alone.

Accordingly, addition of 1 μg/ml sub inhibitory concentration of the proton motive force uncoupler carbonyl cyanide m-chlorophenylhydrazone, CCCP (i.e., another electron transport inhibitor), also caused ATCC 29213 to become susceptible to the growth inhibitory activity of tomatidine (tomatidine MIC of 0.12 μg/ml in presence of CCCP) and increased resistance to gentamicin (MIC of gentamicin of 4-8 μg/ml in presence of CCCP). MICs were determined as described in Example 1 above.

TABLE 3

Susceptibility (MIC in μg/ml) of normal and SCV *S. aureus* strains to tomatidine, tomatine and control antibiotics with or without the presence of HQNO.

| Strain[a] | TO | TN | GEN | VAN | ERY | CIP | OXA |
|---|---|---|---|---|---|---|---|
| ATCC 29213 | >16 | >16 | 1 | 2 | 0.12-0.25 | 0.5 | 0.12-0.25 |
| ATCC 29213 + HQNO | 0.12-0.25 | >16 | 4 | 2 | 0.25 | 0.25 | 0.12 |
| CF07-L | >16 | >16 | 1-2 | 2 | 0.25 | 0.5 | 0.06-0.12 |
| CF07-L + HQNO | 0.5 | >16 | 4 | 2 | 0.25 | 0.25 | 0.06-0.12 |
| CF07-S | 0.12 | >16 | 8 | 2 | 0.12 | 0.12 | 0.06-0.12 |
| CF07-S + HQNO | 0.12 | >16 | 4-8 | 2 | 0.06-0.12 | 0.12 | 0.06-0.12 |

[a]ATCC 29213 and CF07-L are normal strains whereas CF07-S is a SCV. 4-hydroxy-2-heptylquinoline-N-oxide (HQNO) was used at 20 μg/ml.
TO: tomatidine, TN: tomatine, GEN: gentamicin, VAN: vancomycin, ERY: erythromycin, CIP: ciprofloxacin, OXA: oxacillin.

EXAMPLE 4

Effect of Counteracting the Electron Transport Chain Defect of *Staphylococcus aureus* SCV Strains on their Susceptibility to Tomatidine The susceptibility of electron transport-deficient strains to tomatidine is abolished when the strain defect is compensated.

Method:

Normal (Newbould, CF07-L and CF1A-L), and SCV (NewbouldΔhemB (in the presence and absence of hemin), CF07-S (in the presence and absence of menadione) and CF1D-S) *S. aureus* strains were treated with various concentrations of tomatidine (4, 2, 1, 0.5, 0.25, 0.12 and 0.06 μg/ml) for 48 h in the Brain Hearth Infusion (BHI) medium at 35° C. and 10 μl samples were thereafter spotted on agar plated which were further incubated for 48 h before a picture was taken. Results are reported in FIG. 1A.

Results:

As shown in FIG. 1A, the susceptibility of the hemin-dependent electron transport-deficient SCV NewbouldΔhemB and of the menadione-dependent electron transport-deficient SCV CF07-S to tomatidine was abolished in the presence of supplemental hemin and menadione, respectively, which further confirmed that a defective electron transport is required for the antibacterial activity of tomatidine to occur.

EXAMPLE 5

Bacteriostatic Activities of Tomatidine Against Normal *Staphylococcus aureus* Strains and Small-Colony Variants (SCVs)

Time-kill experiments were performed in order to determine whether the effect of tomatidine on SCVs is bacteriostatic (prevents growth) or bactericidal (kills cells).

Method:

Bacteria were inoculated at ~$10^5$-$10^6$ CFU/ml in BHI in the absence or presence of antibiotics at the specified concentrations (concentrations of 16 µg/ml of tomatidine (TO) (n=3), 0.5 µg/ml of erythromycin (ERY) (n=3) and 1.0 µg/ml of ciprofloxacin (CIP) (n=3) were used against CF07-L (FIG. 1B), whereas concentrations of 0.25 µg/ml of TO (n=4), 16 µg/ml of TN (n=3), 0.25 µg/ml of ERY (n=3) and 0.5 µg/ml of CIP (n=2) were used against the SCV strain CF07-S). At several time points during growth at 35° C. (225 RPM), bacteria were sampled, serially diluted and plated on tryptic soy agar (TSA) for colony-forming unit (CFU) determinations (i.e., viable bacterial counts). Plates were incubated for 24 or 48 h at 35° C. for normal and SCV strains, respectively. The antibacterial activities of tomatidine and control antibiotics (erythromycin (a bacteriostatic macrolide) and ciprofloxacin (a bactericidal fluoroquinolone) against the normal CF07-L strain and the SCV CF07-S as a function of time are presented in FIGS. 1B and 1C, respectively. The antibacterial activity of tomatine against the SCV strain was also evaluated (TN in FIG. 1C).

Figure 1B:
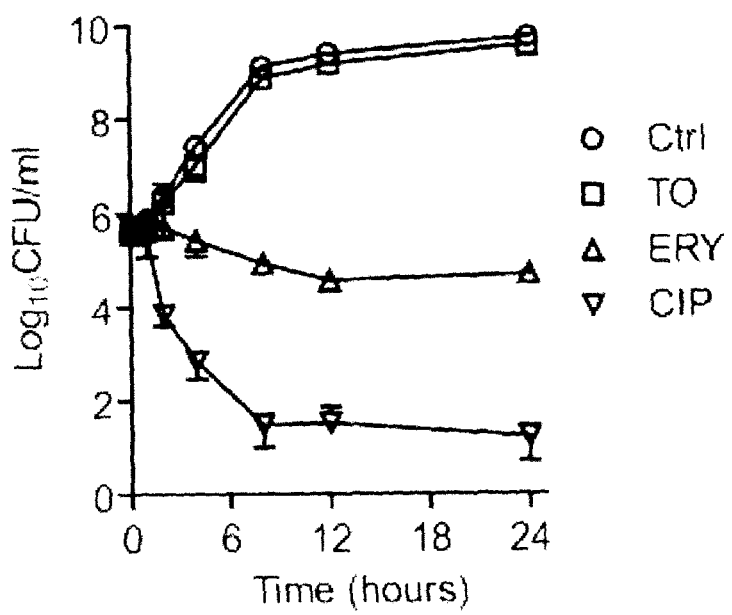
Figure 1C:
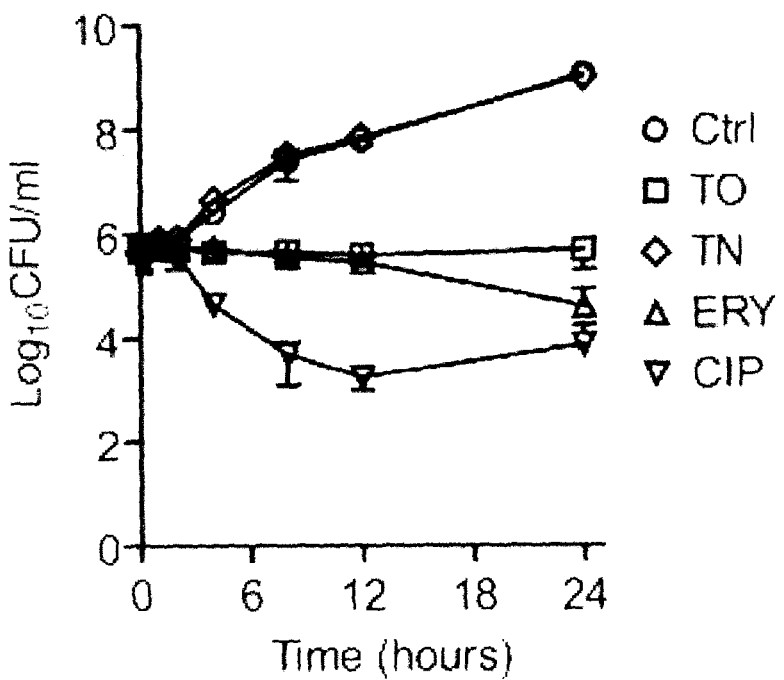

Results: FIG. 1C clearly demonstrates that the presence of tomatidine at 0.25 µg/ml (2×MIC) induced bacteriostasis in SCVs whereas it does not affect the growth of normal strains (FIG. 1B). Tomatidine is thus bacteriostatic like the widely used macrolide class of antibiotics.

EXAMPLE 6

Effect of Tomatidine on the Biosynthesis of Macromolecules in Untreated and HQNO-Treated Normal *Staphylococcus aureus* Strains Tomatidine causes inhibition of the biosynthesis of macromolecules and more specifically protein biosynthesis in electron transport-deficient *S. aureus*.

In order to get insight into the mechanism of action of tomatidine on SCVs, macromolecular biosynthesis assays were performed with the normal strain ATCC 29313 in the absence or presence of 20 µg HQNO/ml. HQNO-treated bacteria were used to create the SCV phenotype because it allowed to achieve an elevated cell densities before the addition of HQNO.

Method:

The complete defined medium (CDM) was used for macromolecular biosynthesis assays. CDM was constituted of the following chemicals per liter: 5 g glucose, 50 mg $MgSO_4$, 7 g $K_2HPO_4$, 2 g $KH_2PO_4$, 0.5 g of Na-Citrate dihydrate, 1 g $(NH_4)_2SO_4$, 1 mg thiamine, 1.2 mg niacin, 0.25 mg calcium pantothenate, 0.005 mg of biotin, 10 mg of L-tryptophan, 5 mg adenine, 5 mg guanine, 5 mg cytosine, 5 mg uracil, 100 mg L-glutamic acid, 90 mg L-aspartic acid, 80 mg L-proline, 50 mg L-arginine, 50 g glycine, 50 mg L-lysine, 60 mg L-alanine, 30 mg L-serine, 20 mg L-cysteine, 10 mg L-methionine, 50 mg L-tyrosine, 40 mg L-phenylalanine, 20 mg L-histidine, 30 mg L-threonine, 30 mg L-isoleucine, 80 mg L-valine, 90 mg L-leucine and 20 mg thymine. The medium CDM-LEU had 22.5 mg/l of L-Leucine instead of 90 mg/l whereas the medium CDM-ALA had 15 mg/l of L-alanine instead of 60 mg/l. Protein, DNA, RNA and cell wall peptidoglycan biosynthesis were evaluated by measuring the incorporation of the appropriate radiolabeled precursors into bacteria prior to treatment with trichloroacetic acid (TCA). Inocula were prepared by incubating bacteria overnight at 35° C. (225 RPM) in the CDM medium. Cultures were then adjusted to an optical density at 600 nm ($A_{600\ nm}$) of 0.1 and grown until an $A_{600}$ nm of 0.3 in CDM, CDM-LEU (protein) or CDM-ALA (cell wall) was achieved. An amount of 3 µCi/ml of [$^3$H]leucine, 1 µCi/ml of [$^3$H]thymine, 1 µCi/ml of [$^3$H]uridine or 2 µCi/ml [$^3$H] D-alanine was added to aliquots of cultures in presence of the different antimicrobial compounds at approximately 4×MIC in order to evaluate protein, DNA, RNA or cell wall peptidoglycan synthesis, respectively. The incorporation of [$^3$H]-molecules into macromolecules were allowed for 45 min for the protein and cell wall assays, and for 35 min for the DNA and RNA assays. Cold 10% TCA was then added to all samples to stop the incorporation and precipitate macromolecules for 1 h on ice. All samples were filtered through a glass microfiber filter (Piscataway, N.J., USA) by using a dot-blot filtration system. Each filter was washed with 100 µl of 10% TCA containing 1.5 M NaCl and 100 µl of 10% TCA. Filters were dried overnight and their radioactivity was measured in a liquid scintillation counter. MICs of the control antibiotics chloramphenicol, norfloxacin, rifampicin and vancomycin against *S. aureus* ATCC 29213 were 8-16, 1, 0.008-0.015 and 0.5-1 µg/ml, respectively (Data not shown).

Figure 3A:
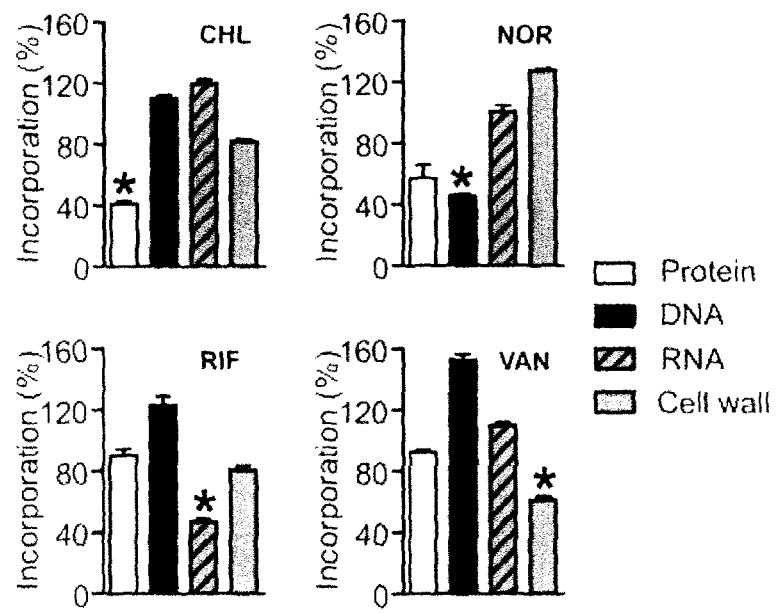
FIGS. 3A-C show the effect of various compounds on the biosynthesis of macromolecules of *S. aureus* in absence or presence of HQNO.
Figure 3B:
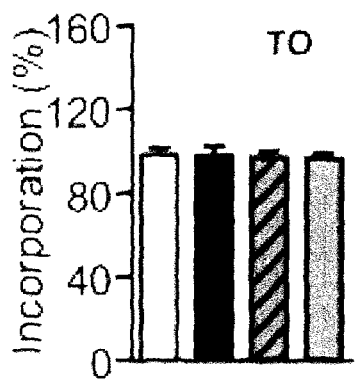
Figure 3C:
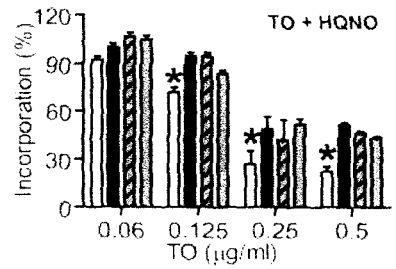

Results:

The effect of control antibiotics chloramphenicol (CHL), norfloxacin (NOR), rifampicin (RIF) and vancomycin (VAN) that are well-known to inhibit protein synthesis, DNA replication, RNA transcription and cell wall peptidoglycan synthesis, respectively, were tested on the normal strain ATCC 29213 at approximately 4×MIC (four times their minimal inhibitory concentration) (FIG. 3A). As expected, each of these antibiotics preferentially inhibited the incorporation of radiolabeled precursors into the targeted macromolecules i.e. (chloramphenicol (CHL); 64 µg/ml), DNA (Norfloxacin (NOR); 4 µg/ml), RNA (Rifampicin (RIF); 0.06 µg/ml) and cell wall peptidoglycan synthesis (Vancomycin (VAN); 4 µg/ml). Tomatidine diluted in dimethyl sulphoxide (DMSO) at a concentration of up to 125 µg/ml did not alter the synthesis of any macromolecule in ATCC 29213 in comparison to the DMSO-treated control (FIG. 3B). However, in the presence of 20 µg HQNO/ml, tomatidine decreased the biosynthesis of all macromolecules at all tested concentrations above 0.12 µg/ml when compared to the HQNO-treated control (FIG. 3C). In presence of HQNO, the inhibition of protein synthesis was significantly more affected by tomatidine than was the biosynthesis of all other macromolecules (FIG. 3C). This indicates that the primary cellular target of tomatidine is the bacterial protein biosynthesis machinery.

EXAMPLE 7

Effect of Tomatidine on the Replication of a Clinical SCV of *Staphylococcus aureus* in Polarized Airway Epithelial Cells Results herein show that tomatidine has an antimicrobial activity against intracellular SCVs. This is particularly relevant because the ability of SCVs to persist within host cells is thought to be involved in the development of chronic and difficult-to-treat infections (Sendi and Proctor, 2009). More precisely, the following results demonstrate that tomatidine can significantly decrease the infection of polarized airway epithelial cells by SCVs by inhibiting their ability to replicate inside cells.

Method:

The human airway epithelial cells, shCFTR, which mimic the CFTR defect, were derived from the Calu-3 cell line ATCC HTB 55 (Palmer et al., 2006). The shCFTR cells were cultured in Eagle's Minimum Essential Medium (EMEM) supplemented with 0.1 mM MEM nonessential amino acids, 1 mM of sodium pyruvate, 100 U/ml penicillin, 0.1 mg/ml streptomycin, 2.5 µg/ml of Fungizone and 10% fetal bovine serum (FBS) at 37° C. in 5% $CO_2$. For routine culture, 4 µg/ml of puromycin was added to culture media. All cell culture reagents were purchased from Wisent (St-Bruno, QC, Canada). Cell infection assays were performed as previously described with few adaptations for the Transwell™ system (Mitchell et al., 2010c). Cells were seeded at $2.5 \times 10^5$ cells/inserts on 12-well Transwell™ plates and cultured for 9 to 10 days in an air:liquid system. The complete medium in the basal compartment was replaced by the invasion medium (1% FBS and no antibiotics) 18 h before assays. Inocula were prepared by suspending bacteria grown 20 h on BHIA plates in ice-cold PBS. Bacteria (CF07-L or CF07-S) were then washed three times in ice-cold PBS and suspended in the invasion medium supplemented with 0.5% BSA at a density of approximately $4 \times 10^8$ CFU/ml. Cells were washed twice with PBS and 250 µl of bacterial suspension were apically added to each insert. Invasion was allowed for 3 h, inserts were emptied and washed three times with PBS. Invasion medium supplemented with 20 µg/ml of lysostaphin (Sigma) was then added to kill extracellular bacteria and the cells were further incubated 24 or 48 h in presence of lysostaphin. DMSO or the different concentrations of tomatidine were added after invasion. Cells were washed once with PBS and the invasion medium supplemented with lysostaphin, DMSO and/or tomatidine was replaced at 24 h post-internalization. Fresh invasion medium supplemented with lysostaphin was also added 1 h before cell lysis to ensure that only intracellular bacteria were counted. Following three washes with PBS, cells were detached with 100 µl of trypsin 0.25% and lyzed for 10 min by the addition of 400 µl of water containing 0.05% of Triton X-100. Lysates were serially diluted 10-fold and plated on agar for CFU determination. Plates were incubated for 24 or 48 h at 35° C. for normal and SCV strains, respectively. Results are reported in FIGS. 4A and B.

Figure 4A:
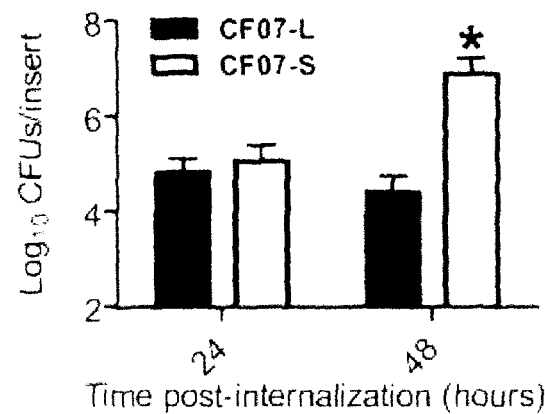
FIGS. 4A-B show the effect of tomatidine on the intracellular replication of a clinical SCV strain of S. aureus in polarized cystic fibrosis (CF) airway epithelial cells.
Figure 4B:
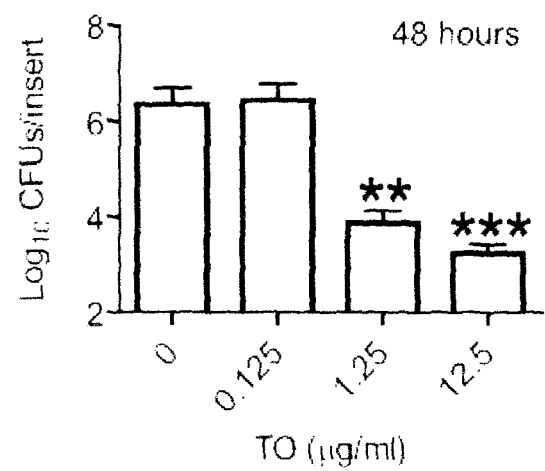

Results:

FIG. 4A shows that, although both normal and SCV strains caused similar level of infection at 24 h post-internalization, the intracellular load of the SCV strain CF07-S 48 h post-internalization was clearly larger than that resulting from the normal strain CF07-L. A significant difference between cells infected with CF07-L and CF07-S 48 h post-internalization is shown. These differences in cellular infection levels are explained by the ability of SCVs to persist and replicate within epithelial cells (Moisan et al., 2006; Sendi and Proctor, 2009). The impact of tomatidine on the infection of epithelial cells by SCVs was evaluated. FIG. 4B demonstrated that cells treated with 1.25 and 12.5 µg/ml of tomatidine (diluted in DMSO) contained significantly less SCVs CF07-S than the DMSO-treated control cells 48 h post-internalization.

EXAMPLE 8

Effect of Tomatidine on Normal S. Aureus Bacteria in Co-Culture with Pseudomonas aeruginosa Given that S. aureus and P. aeruginosa are often co-isolated from the airways of CF patients and that P. aeruginosa is known to produce respiratory inhibitors targeting S. aureus such as HQNO and pyocyanin (Mitchell et al., 2010b; Voggu et al., 2006) as well as other antisapthylococcal compounds (Kessler et al., 1993; Qazi et al., 2006, the effect of tomatidine on the viability of S. aureus in co-culture with P. aeruginosa was tested. Results herein demonstrate that tomatidine kills normal S. aureus bacteria when grown in presence of P. aeruginosa.

Methods:

S. aureus bacteria were inoculated at $\sim 10^5$-$10^6$ CFU/ml in Cation-adjusted Mueller-Hinton broth (CAMHB) and grown at 35° C. with shaking in the absence or presence of 8 µg/ml tomatidine. Bacteria were sampled, serially diluted and plated on tryptic soy agar for CFU determinations. For experiments in co-culture, both S. aureus ATCC 29213 and P. aeruginosa PA14 were inoculated at $\sim 10^5$-$10^6$ CFU/ml. Mannitol-salt agar plates were used to selectively evaluate S. aureus CFU when in co-culture with P. aeruginosa.

Results:

Table 4 shows that while tomatidine does not significantly alter the growth of the normal S. aureus strain ATCC 29213 when in mono-culture, the viability of this bacterium is decreased by the presence of tomatidine when in co-culture with the P. aeruginosa strain PA14. More precisely, exposure of ATCC 29213 to tomatidine significantly decreases its viability when in co-culture with PA14 in comparison to all other conditions (P<0.01; one-way ANOVA with Tuckey's post test). In contrast to the bacteriostatic effect of tomatidine on SCVs, tomatidine is bactericidal against S. aureus bacteria in co-culture with P. aeruginosa.

TABLE 4

Effect of tomatidine (TO) at 8 µg/ml on the viability (in $Log_{10}$ CFU/ml) of the normal S. aureus (SA) ATCC 29213 alone or in co-culture with P. aeruginosa (PA).

| | Viability of S. aureus (in $Log_{10}$ CFU/ml) at two time points [a] | |
|---|---|---|
| Conditions | 0 h | 24 h |
| SA alone | 5.3 ± 0.1 | 10.0 ± 0.1 |
| SA alone + TO | 5.1 ± 0.4 | 9.64 ± 0.08 |
| SA + PA | 5.36 ± 0.03 | 5.4 ± 0.7 |
| SA + PA + TO | 5.4 ± 0.1 | 2 ± 1 [b] |

[a] Results are presented as means ± standard deviations from 2 to 3 independent experiments.
[b] P < 0.01; one-way ANOVA with Tuckey's post test.

EXAMPLE 9

Combined Effect of Tomatidine and Gentamicin Against Heterogeneous Staphylococcus aureus Populations Composed of Both Normal and SCV Strains Tomatidine can be used in combination with classical antibiotics during therapies, especially in patients simultaneously infected by SCVs and S. aureus having the normal phenotype. Tomatidine can complement the antibacterial effect of the aminoglycoside antibiotics (e.g., gentamicin) against a bacterial population composed of both normal and SCV strains of S. aureus.

Method:

Bacteria were inoculated at ~$10^5$-$10^6$ CFU/ml in BHI in absence or presence of gentamicin and/or tomatidine at 4 and 0.12 μg/ml, respectively. Cultures were incubated 48 h at 35° C./225 RPM and the growth was visually evaluated. Results are reported in FIGS. 5A and B.

Figure 5A:
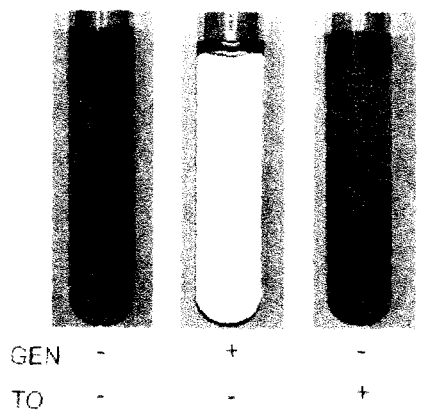
FIGS. 5A-C show the effect of tomatidine and gentamicin alone or in combination on both pure and mixed cultures of normal and SCV S. aureus strains.
Figure 5B:
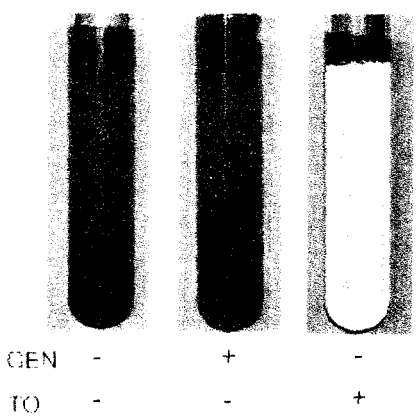
Figure 5C:
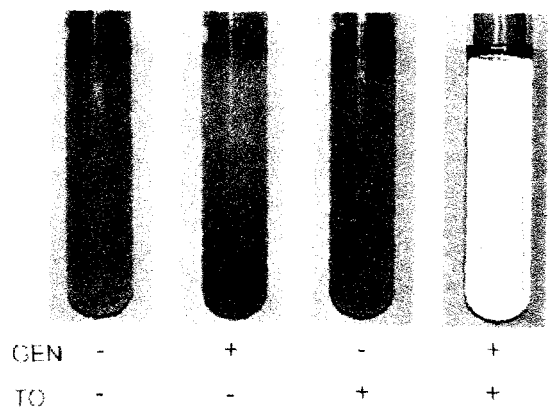

Results:

FIG. 5A shows that gentamicin at 4 μg/ml inhibits the growth of the normal strain CF07-L whereas tomatidine at 0.12 μg/ml does not. FIG. 5B shows that gentamicin at 4 μg/ml does not inhibit the growth of the SCV CF07-S while tomatidine at 0.12 μg/ml does. Finally, in FIG. 5C, a combination of gentamicin at 4 μg/ml and tomatidine at 0.12 μg/ml inhibits the growth of a heterogeneous population composed of both the normal strain CF07-L and the SCV CF07-S whereas neither antibiotic molecule alone can.

EXAMPLE 10

Potentiating Effect of Tomatidine on Aminoglycoside Antibiotics Against Normal Staphylococcal Strains Results of the assays used in this example report the unexpected discovery that tomatidine specifically and selectively increases the antibacterial activity of aminoglycoside antibiotics against Staphylococcus Spp. that are not electron transport-deficient.

Method:

The MICs of gentamicin (aminoglycoside), tobramycin (aminoglycoside), amikacin (aminoglycoside), streptomycin (aminoglycoside), kanamycin (aminoglycoside), oxacillin (beta-lactam), erythromycin (macrolide), norfloxacin (fluoroquinolone), ciprofloxacin (fluoroquinolone), tetracycline and vancomycin (glycopeptide) with or without tomatidine (TO) against normal S. aureus strain ATCC 29213 were determined using the microdilution method in 96-well microplates. Bacteria were inoculated at ~$10^5$-$10^6$ CFU/ml and incubated at 35° C. for 24 h in CAMHB. Then $OD_{595\ nm}$ was read on a microplate reader. Results are reported in Table 5 below.

Results:

Table 5 below shows that tomatidine decreases the MICs (i.e. increases the susceptibility) of the aminoglycoside antibiotics gentamicin, tobramycin, amikacin, streptomycin and kanamycin against the non electron transport-deficient S. aureus ATCC 29213. As an example, tomatidine at 8 μg/ml increases the antibacterial activity of gentamicin and tobramycin against ATCC 29213 between 8-32 and 4-8 fold, respectively.

TABLE 5

Susceptibility (MIC in μg/ml) of S. aureus ATCC 29213 to several antibiotics in absence or presence of tomatidine at 8 μg/ml.

| Antibiotic | −TO | +TO | Fold (−TO/+TO)[a] |
|---|---|---|---|
| Gentamicin | 0.5-1 | 0.03-0.06 | 8-32 |
| Tobramycin | 0.25-0.5 | 0.06 | 4-8 |
| Amikacin | 2 | 0.5 | 4 |
| Streptomycin | 4-8 | 1 | 4-8 |
| Kanamycin | 2-4 | 0.5 | 4-8 |
| Oxacillin | 0.25 | 0.25 | 1 |
| Erythromycin | 0.5 | 0.5 | 1 |

TABLE 5-continued

Susceptibility (MIC in μg/ml) of S. aureus ATCC 29213 to several antibiotics in absence or presence of tomatidine at 8 μg/ml.

| Antibiotic | −TO | +TO | Fold (−TO/+TO)[a] |
|---|---|---|---|
| Norfloxacin | 1-2 | 1-2 | 1 |
| Ciprofloxacin | 0.5 | 0.5 | 1 |
| Tetracycline | 0.25-0.5 | 0.25-0.5 | 1 |
| Vancomycin | 1 | 1 | 1 |

[a]Increased susceptibility measured in fold differences. Differences between unexposed (−TO) and exposed (+TO) results were determined for each independent experiments and are presented as intervals.

Results:

Table 6 below shows that the potentiating effect of tomatidine on the antibacterial activity of aminoglycoside antibiotics is also efficient against other clinically important Staphylococcus spp. (e.g., S. epidermidis, S. haemolyticus, S. saprophyticus and S. hominis). Results are from MIC experiments.

TABLE 6

Susceptibility (MIC in μg/ml) of several Staphylococcus spp. strains to the aminoglycoside antibiotics gentamicin and tobramycin in absence or presence of 8 μg/ml of tomatidine.

| Species | Strain | Antibiotic | −TO | +TO | Fold (−TO/+TO)[a] |
|---|---|---|---|---|---|
| S. epidermidis | ATCC 12228 | Gentamicin | 0.12 | 0.06 | 2 |
|  |  | Tobramycin | 0.12 | 0.06 | 2 |
|  | ATCC 35984 | Gentamicin | 32 | 8 | 4 |
|  |  | Tobramycin | 16 | 2 | 8 |
| S. haemolyticus | sh022 | Gentamicin | 16 | 4 | 4 |
|  |  | Tobramycin | 32 | 4 | 8 |
|  | sh032 | Gentamicin | 64 | 8 | 8 |
|  |  | Tobramycin | 32 | 2 | 16 |
| S. saprophyticus | ATCC 15305 | Gentamicin | ND | ND | ND |
|  |  | Tobramycin | 0.12 | 0.016 | 8 |
| S. hominis | ssp008c | Gentamicin | 8 | 2 | 4 |
|  |  | Tobramycin | 32 | 8 | 4 |
|  | sho23 | Gentamicin | 0.12 | 0.06 | 2 |
|  |  | Tobramycin | 4 | 1 | 4 |

[a]Increased susceptibility measured in fold differences. Differences between unexposed (−TO) and exposed (+TO) results were determined for each independent experiments and are presented as intervals.
ND not determined.

Method:

A checkerboard protocol was used in order to determine the effect of aminoglycoside antibiotics on ATCC 29213 as a function of tomatidine concentration. This checkerboard protocol (Eliopoulos and Moellering, 1996) was conducted by a microdilution method similar to that use for standard MICs determination. In 96 wells plates, antibiotics were loaded at a 4× concentration (where X is the maximal tested concentration) in well A1 and at a 2× concentration in the others wells of the column 1. Antibiotics were serially diluted 1:1 from the column 2 to column 10. Tomatidine was then loaded in wells A1 to A11 at a 4× concentration and serially diluted 1:1 from row B to row G. Row H was without tomatidine whereas column 11 was without antibiotic. Wells A12, B12, C12 and D12 are positive untreated controls whereas wells E12, F12, G12 and H12 are negative non-inoculated controls. Bacteria were inoculated at ~$10^5$-$10^6$ CFU/ml and incubated at 35° C. for 24 h in CAMHB. Then $OD_{595\ nm}$ was read on microplate reader. Results shown in Table 7 below are the MICs determined for the aminoglycosides by this checkerboard method in presence of the indicated amounts of tomatidine. The FIC index was calculated as follow (Eliopoulos and Moellering, 1996): FIC index=FICA+FICB=A/MICA+B/MICB, where A and B are MICs of compounds A and B in combination and where MICA and MICB are the MICs of compound A alone and of compound B alone, respectively, and FICA and FICB are the FICs of compound A and of compound B, respectively. The analysis of the FIC index demonstrates a total synergy if the FIC index is ≤0.5, a partial synergy if the FIC index is >0.5 and ≤0.75, an additive effect of both compound if the FIC index is >0.75 and ≤1, and an antagonistic effect if the FIC index is >2.

Results:

Table 7 below shows that in a checkerboard assay, tomatidine creates a synergy with all tested aminoglycoside antibiotics (i.e. tobramycin (TOB), gentamicin (GEN), amikacin (AMI), streptomycin (STR) and kanamycin (KAN)) with a calculated Fractional Inhibitory Concentration (FIC) index below 0.5.

TABLE 7

Susceptibility (MIC in μg/ml) of *S. aureus* ATCC 29213 to several aminoglycoside antibiotics as a function of tomatidine concentration.

| Tomatidine (μg/ml) | Gentamicin | Tobramycin | Amikacin | Streptomycin | Kanamycin |
|---|---|---|---|---|---|
| 0 | 0.5-1 | 0.25-0.5 | 2 | 4-8 | 2-4 |
| 0.06 | 0.25 | 0.25 | 2 | 4 | 2 |
| 0.12 | 0.06-0.25 | 0.03-0.12 | 0.5 | 2 | 0.5-1 |
| 0.25 | 0.06 | 0.03-0.06 | 0.25 | 1-2 | 0.5 |
| 0.5 | 0.06 | 0.03 | 0.25-0.5 | 1 | 0.5 |
| 1 | 0.03-0.06 | 0.03-0.06 | 0.25-1 | 1 | 0.5-1 |
| 2 | 0.06-0.12 | 0.03-0.06 | 0.25-1 | 1 | 0.25-0.5 |
| 4 | 0.03-0.12 | 0.03-0.06 | 0.25 | 1 | 0.5 |
| 8 | 0.03-0.06 | 0.06 | 0.5 | 1 | 0.5 |
| FIC index[a] | ≤0.116 | ≤0.133 | ≤0.133 | ≤0.199 | ≤0.193 |

[a] Although tomatidine alone did not inhibit the growth of normal *S. aureus* strains, a MIC value of 32 μg/ml was considered for tomatidine in order to approximate FIC indexes. The symbol "≤" in of the FIC index values indicates that these values are overestimated. A FIC index below 0.5 indicates a strong synergy.

EXAMPLE 11

Potentiating Effect of Tomatidine on Aminoglycoside Antibiotics Against Staphylococcal Strains of Multiple Clinical Origins and Against Multi-Resistant Staphylococcal Strains The potentiating effect of tomatidine on the antibacterial activity of aminoglycoside antibiotics against *S. aureus* is efficient against several strains isolated from human and veterinary infections, including antibiotic-resistant S, aureus strains.

Figure 6A:
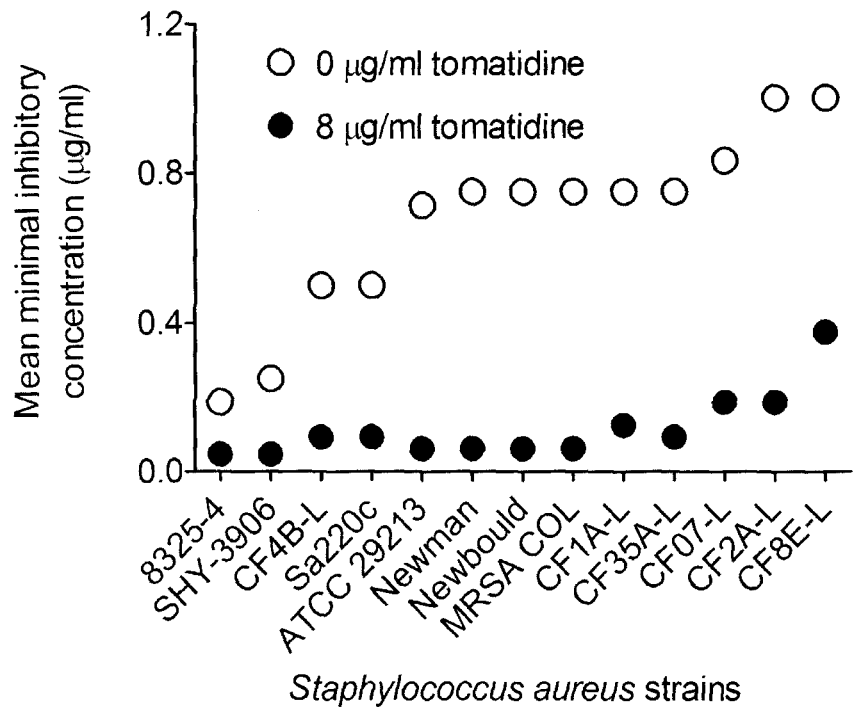
FIG. 6A displays the MIC of the aminoglycoside gentamicin in absence (0 µg/ml) or presence of tomatidine (8 µg/ml) for several normal S. aureus strains (i.e. 8325-4, SHY-3906, CF4B-L, Sa220c, ATCC 29213, Newman, Newbould, MRSA COL, CF1A-L, CF35A-L, CF07-L, CF2A-L and CF8E-L).
Figure 6B:
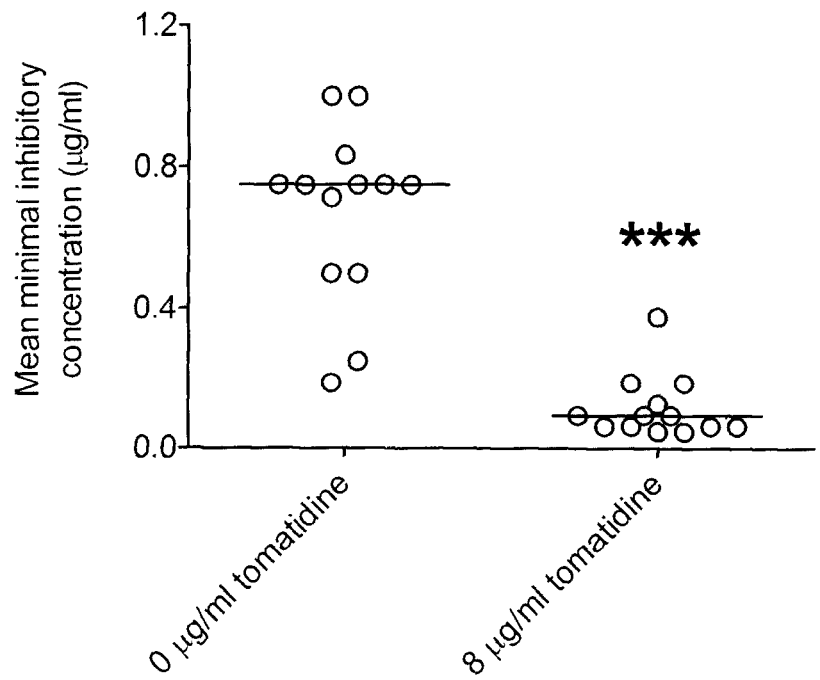
In FIG. 6B, the distribution of the MIC for gentamicin for these strains in absence (0 µg/ml) or presence of tomatidine (8 µg/ml) are compared. Median values (bars) of both distributions are indicated. Distributions were compared with a Mann Whitney test (***, P<0.001). MIC results are presented as the means from at least two independent experiments.
Figure 7A:
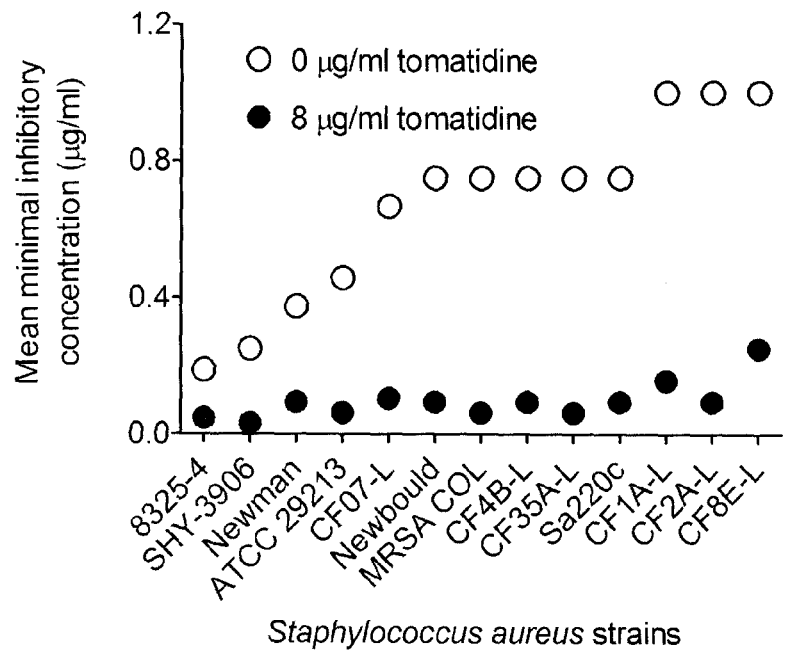
FIG. 7A displays the MIC of the aminoglycoside tobramycin in absence (0 µg/ml) or presence of tomatidine (8 µg/ml) for the same normal S. aureus strains as in FIGS. 6A and B (i.e. 8325-4, SHY-3906, Newman, ATCC 29213, CF07-L, Newbould, MRSA COL, CF4B-L, CF35A-L, Sa220c, CF1A-L, CF2A-L and CF8E-L).
Figure 7B:
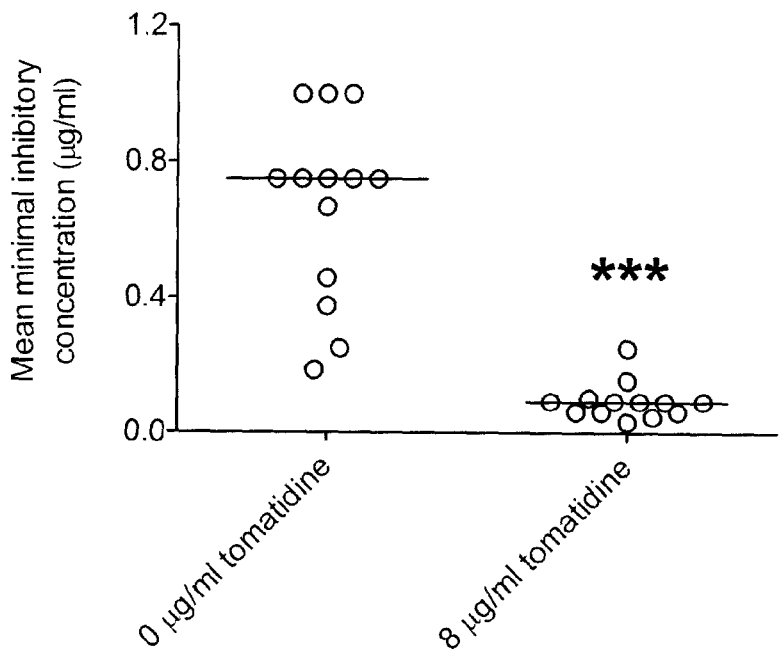
In FIG. 7B, the distribution of the MIC for tobramycin among these same strains in absence (0 µg/ml) or presence of tomatidine (8 µg/ml) were compared. Median values (bars) of both distributions are indicated. Distributions were compared with a Mann Whitney test (***, P<0.001). MIC results are presented as the means from at least two independent experiments.

Results:

Table 8 below shows the antibiotic susceptibility profile of several normal *S. aureus* strains isolated from both human and veterinary infections. While several strains are susceptible to all of the antibiotics tested (e.g., CF1A-L), others are resistant to one or several antibiotics (e.g., Sa228c) and may include methicillin-resistant (e.g., MRSA COL) or vancomycin-intermediate (e.g., Mu50) *S. aureus* and the like (MRSA, Vancomycin-intermediate *Staphylococcus aureus* (VISA), glycopeptide-intermediate *Staphylococcus aureus* (GISA), Vancomycin-resistant *Staphylococcus aureus* (VRSA)). Table 9 below shows that tomatidine decreases the MICs (i.e. increases the susceptibility) of *S. aureus* isolates, including antibiotic-resistant *S. aureus*, to gentamicin, tobramycin and kanamycin. This potentiating effect of tomatidine on the gentamicin and tobramycin activity is also illustrated in FIGS. 6A and 7A, respectively. FIGS. 6B and 7B show that this potentiating effect of tomatidine is highly significant (P<0.001). For example, tomatidine at 8 μg/ml increases in average the antibacterial activity of gentamicin and tobramycin against all tested *S. aureus* strains by 8±3 fold. The determination of MICs was performed as described in Example 10 above.

TABLE 8

Antibiotic susceptibility profile (MIC in μg/ml) of several *S. aureus* strains isolated from both human and veterinary infections

| Strain | Origin (infection) | GEN | TOB | KAN | OXA | ERY | NOR | TET | VAN | CIP |
|---|---|---|---|---|---|---|---|---|---|---|
| 8325-4 | Laboratory strain | 0.12-0.25 | 0.12-0.25 | 2-8 | 0.12 | 0.25-0.5 | 1-2 | 0.25 | 1 | 0.25-0.5 |
| Newbould | Cow (mastitis) | 0.5-1 | 0.5-1 | 4 | 0.12 | 0.5 | 0.5 | 0.25-0.5 | 0.5-1 | 0.25 |
| SHY97-3906 | Cow (mastitis) | 0.25 | 0.25 | 2 | 0.12-0.25 | 0.12-0.25 | 0.5-1 | 0.25-0.5 | 0.5-1 | 0.25 |
| ATCC 43300 | Human (HA) | 64-128 (R) | 512-1024 (R) | 512-1024 (R) | 16-32 (R) | >64 (R) | ND | 0.5 | 0.5-1.0 | 0.5 |
| ATCC BAA-41 | Human (HA) | 0.5 | 512 (R) | 256-512 (R) | >64 (R) | >64 (R) | ND | 0.5 | 1 | >64 (R) |
| N315 | Human (HA) | 1 | 512 (R) | 256 (R) | 8 (R) | >64 (R) | ND | 0.5 | 0.5 | 0.25 |
| MA078038 | Human (CA) | 0.25-0.5 | 0.5 | >1024 (R) | 64 (R) | 64 (R) | ND | 0.5 | 0.5-1.0 | 16 (R) |
| Newman | Human (Osteo) | 0.5-1 | 0.25-0.5 | 4 | 0.5-1 | 0.5 | 1 | 0.25-0.5 | 1 | 0.25 |
| ATCC 29213 | Human (SSTI) | 0.5-1 | 0.25-0.5 | 2-4 | 0.25 | 0.5 | 1-2 | 0.25-0.5 | 1 | 0.5 |
| MRSA COL | Human (SSTI) | 0.5-1 | 0.5-1 | 4 | >64 (R) | 0.5 | 2-4 | 1-2 | 2 | 0.5 |
| Mu50 | Human (SSTI) | 128 (R) | 1024 (R) | >1024 (R) | >64 (R) | >64 (R) | >64 (R) | >16 (R) | 4 (I) | 32-64 (R) |
| Sa220c | Human (SSTI) | 0.5 | 0.5-1 | 4 | 16-32 (R) | 0.5-1 | >64 (R) | 0.5 | 1 | 32 (R) |
| Sa228c | Human (SSTI) | 64-128 (R) | 1024 (R) | 512-1024 (R) | >64 (R) | >64 (R) | >64 (R) | >16 (R) | 1 | >64 (R) |

TABLE 8-continued

Antibiotic susceptibility profile (MIC in μg/ml) of several S. aureus strains isolated from both human and veterinary infections

| Strain | Origin (infection) | GEN | TOB | KAN | OXA | ERY | NOR | TET | VAN | CIP |
|---|---|---|---|---|---|---|---|---|---|---|
| CF1A-L | Human (CF lungs) | 0.5-1 | 1 | 4 | 0.25-0.5 | 0.25-0.5 | 1 | 0.25 | 1 | 0.5-1 |
| CF2A-L | Human (CF lungs) | 1 | 1 | 4 | 0.25 | 0.5 | 0.5-1 | 2 | 1 | 0.25 |
| CF4B-L | Human (CF lungs) | 0.5 | 0.5-1 | 4 | 0.5 | 0.5 | 1 | 0.25 | 1 | 0.25-0.5 |
| CF6B-L | Human (CF lungs) | 128-256 (R) | 256 (R) | 1024 (R) | 0.25-1 | 0.5-2 | >64 (R) | 0.25 | 0.5-1 | >64 (R) |
| CF7A-L | Human (CF lungs) | 0.5-1 | 1024 (R) | 256-512 (R) | >64 (R) | >64 (R) | >64 (R) | 0.25-0.5 | 1 | >64 (R) |
| CF8E-L | Human (CF lungs) | 1 | 1 | 16 | 0.125 | 0.5 | 4 | 0.25-0.5 | 1-2 | 1 |
| CF9A-L | Human (CF lunge) | 0.5-1 | 512-1024 (R) | 256 (R) | >64 (R) | >64 (R) | >64 (R) | 0.25-0.5 | 1 | >64 (R) |
| CF35A-L | Human (CF lunge) | 0.5-1 | 0.5-1 | 4 | >64 (R) | >64 (R) | >64 (R) | 0.5 | 1 | >64 (R) |
| CF07-L | Human (CF lunge) | 0.5-1 | 0.5-1 | 4 | 0.12-0.25 | 0.5 | 1-2 | 0.5 | 1-2 | 0.5 |

ATCC 29213, Newman and 8325-4 are control strains.
Newbould (ATCC 29740) and SHY-3906 are strains isolated from bovine mastitis.
MRSA COL, ATCC 43300, ATCC BAA-41, N315, MA078038, Mu50, CF7A-L, CF9A-L, CF35A-L, Sa220c and Sa228c are methicillin-resistant strains (MRSA).
Mu50 is also a vancomycin-intermediate resistant S. aureus (VISA).
CF1A-L, CF2A-L, CF4B-L, CF6B-L, CF7A-L, CF8E-L, CF9A-L, CF35A-L and CF07-L are pulmonary isolates (MRSA or not) from human patients with cystic fibrosis.
GEN: gentamicin, TOB: tobramycin, KAN: kanamycin, OXA: oxacillin, ERY: erythromycin, NOR: norfloxacin, TET: tetracycline, VAN: vancomycin, CIP: ciprofloxacin.
Intemiediate resistance (I) and resistance (R) to antibiotics.
HA: Hospital-associated isolate; CA: Community-associated isolate; SSTI: Skin and soft tissue infection/wound; CF: Cystic fibrosis; Osteo: Osteomyelitis; ND: Not determined.

TABLE 9

Susceptibility (MIC in μg/ml) of several S. aureus strains to the aminoglycoside antibiotics gentamicin, tobramycin and kanamycin in absence or presence of 8 μg/ml of tomatidine.

| Strain | Antibiotic | −TO | +TO | Fold (−TO/+TO)[a] |
|---|---|---|---|---|
| ATCC 29123 | Gentamicin | 0.5-1 | 0.03-0.06 | 8-32 |
| | Tobramycin | 0.25-0.5 | 0.03-0.06 | 4-16 |
| | Kanamycin | 2-4 | 0.5 | 4-8 |
| Newman | Gentamicin | 0.5-1 | 0.06 | 8-16 |
| | Tobramycin | 0.25-0.5 | 0.06-0.12 | 2-8 |
| | Kanamycin | 4 | 0.5 | 8 |
| 8325-4 | Gentamicin | 0.12-0.25 | 0.03-0.06 | 4 |
| | Tobramycin | 0.12-0.25 | 0.03-0.06 | 4 |
| | Kanamycin | 2-8 | 0.5-4 | 2-4 |
| Newbould | Gentamicin | 0.5-1 | 0.06 | 8-16 |
| | Tobramycin | 0.5-1 | 0.06-0.12 | 8 |
| | Kanamycin | 4 | 0.5 | 8 |
| SHY-3906 | Gentamicin | 0.25 | 0.03-0.06 | 4-8 |
| | Tobramycin | 0.25 | 0.03 | 8 |
| | Kanamycin | 2 | 0.5 | 4 |
| MRSA COL | Gentamicin | 0.5-1 | 0.06 | 8-16 |
| | Tobramycin | 0.5-1 | 0.06 | 8-16 |
| | Kanamycin | 4 | 0.5 | 8 |
| CF1A-L | Gentamicin | 0.5-1 | 0.12 | 4-8 |
| | Tobramycin | 1 | 0.06-0.25 | 4-16 |
| | Kanamycin | 4 | 0.5 | 8 |
| CF2A-L | Gentamicin | 1 | 0.12-0.25 | 4-8 |
| | Tobramycin | 1 | 0.06-0.12 | 8-16 |
| | Kanamycin | 4 | 0.5 | 8 |
| CF4B-L | Gentamicin | 0.5 | 0.06-0.12 | 4-8 |
| | Tobramycin | 0.5-1 | 0.06-0.12 | 4-16 |
| | Kanamycin | 4 | 0.5 | 8 |
| CF8E-L | Gentamicin | 1 | 0.25-0.5 | 2-4 |
| | Tobramycin | 1 | 0.25 | 4 |
| | Kanamycin | 16 | 2-8 | 2-4 |
| CF35A-L | Gentamicin | 0.5-1 | 0.06-0.12 | 8 |
| | Tobramycin | 0.5-1 | 0.06 | 8-16 |
| | Kanamycin | 4 | 1 | 4 |
| CF07-L | Gentamicin | 0.5-1 | 0.06-0.25 | 4-8 |
| | Tobramycin | 0.5-1 | 0.06-0.12 | 4-8 |
| | Kanamycin | 4 | 0.5-1 | 4-8 |
| Sa220c | Gentamicin | 0.5 | 0.06-0.12 | 4-8 |
| | Tobramycin | 0.5-1 | 0.06-0.12 | 4-16 |
| | Kanamycin | 4 | 0.5 | 8 |

[a]Increased susceptibility measured in fold differences. Differences between unexposed (−TO) and exposed (+TO) results were determined for each independent experiments and are presented as intervals.

EXAMPLE 12

Potentiating Effect of Tomatidine on Aminoglycoside Antibiotics Against Staphylococcal Strains that are Specifically Resistant to Aminoglycosides The potentiating effect of tomatidine on the antibacterial activity of aminoglycoside antibiotics against *staphylococci* is also efficient against aminoglycoside-resistant strains.

Results:

Table 10 below shows that tomatidine increased the susceptibility of gentamicin-resistant, tobramycin-resistant and kanamycin-resistant strains to gentamicin, tobramycin and kanamycin despite their resistance against one or several of these antibiotics. More particularly, the nine strains included in Table 10 below are resistant to several antibiotics (see Table 8 above) and are thus multi-resistant strains likely to cause difficult-to-treat infections. The determination of MICs was conducted as described in Example 10 above. The strains used in Table 10 below were also characterized for their content in some resistance genes responsible for aminoglycoside resistance and coding for aminoglycoside-modifying enzymes, following the PCR detection procedure of Schmitz et al (1999). The aminoglycoside resistance determinants that were detected are reported in Table 10 below.

TABLE 10

Susceptibility (MIC in µg/ml) of several aminoglycoside-resistant *S. aureus* strains to the aminoglycoside antibiotics gentamicin, tobramycin and kanamycin in absence or presence of 8 µg/ml of tomatidine.

| Strain | Resistance determinant | Antibiotic | −TO | +TO | Fold (−TO/+TO)[a] |
|---|---|---|---|---|---|
| ATCC 43300 | ND | Gentamicin | 64-128 | 16-32 | 4 |
| | | Tobramycin | 512-1024 | 128 | 4-8 |
| | | Kanamycin | 512-1024 | 256 | 2-4 |
| ATCC BAA-41 | ant(4')-Ia | Gentamicin | 0.5 | 0.12-0.25 | 2-4 |
| | | Tobramycin | 512 | 128 | 4 |
| | | Kanamycin | 256-512 | 64 | 4-8 |
| N315 | ant(4')-Ia | Gentamicin | 1 | 0.12 | 8 |
| | | Tobramycin | 512 | 128-256 | 2-4 |
| | | Kanamycin | 256 | 64 | 4 |
| MA078038 | aph(3')-IIIa | Gentamicin | 0.25-0.5 | 0.06 | 4-8 |
| | | Tobramycin | 0.5 | 0.06-0.12 | 4-8 |
| | | Kanamycin | >1024 | 1024 | >1 |
| Mu50 | aac(6')-aph(2''), ant(4')-Ia | Gentamicin | 128 | 16 | 8 |
| | | Tobramycin | 1024 | 128 | 8 |
| | | Kanamycin | >1024 | 256-512 | >2-4 |
| CF6B-L | aac(6')-aph(2'') | Gentamicin | 128-256 | 16-32 | 4-8 |
| | | Tobramycin | 256 | 16-64 | 4-16 |
| | | Kanamycin | 1024 | 128-256 | 4-8 |
| CF7A-L | ant(4')-Ia | Gentamicin | 0.5-1 | 0.12-0.25 | 2-8 |
| | | Tobramycin | 1024 | 128-512 | 2-8 |
| | | Kanamycin | 256-512 | 64-256 | 2-4 |
| CF9A-L | ant(4')-Ia | Gentamicin | 0.5-1 | 0.06-0.12 | 4-8 |
| | | Tobramycin | 512-1024 | 64-256 | 4-8 |
| | | Kanamycin | 256 | 128-256 | 1-2 |
| Sa228c | aac(6')-aph(2''), ant(4')-Ia | Gentamicin | 64-128 | 8-16 | 8 |
| | | Tobramycin | 1024 | 128-256 | 4-8 |
| | | Kanamycin | 512-1024 | 128-256 | 2-8 |

[a]Differences between unexposed (−TO) and exposed (+TO) results were determined for each independent experiments and are presented as intervals.
ND: Not determined.

EXAMPLE 13

Bacteriostatic and Bactericidal Activities of Steroid Alkaloid Compounds Alone or in Combination with Aminoglycosides The antibacterial activity of steroid alkaloids were determined in time-kill experiments using the method described in Example 5 above, alone or in combination with aminoglycosides against the electron transport-deficient variants or the normal (i.e. non electron transport-deficient) strains, respectively, of a variety of bacterial species. Bacteria were inoculated at ~$10^5$-$10^6$ CFU/ml in BHI or MHBCA in the absence or presence of antibiotics at the specified concentrations. At several time points during growth at 35° C., cultures were sampled, serially diluted and plated on TSA for CFU determinations.

Figure 8:
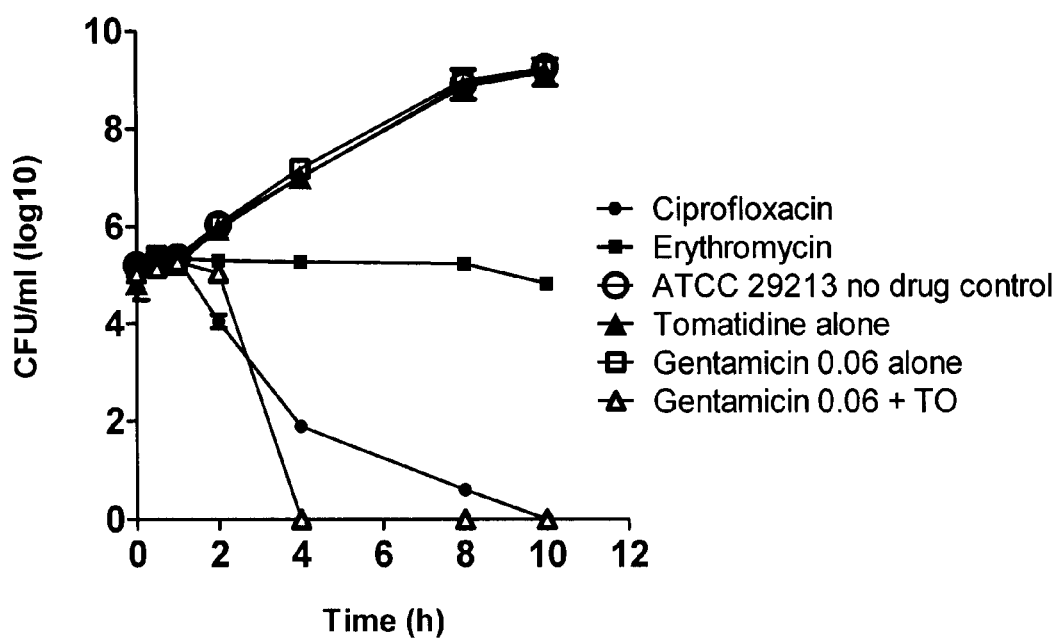
FIG. 8 shows the effect of tomatidine (at 8 µg/ml), erythromycin (at 2 to 4×MIC; 0.5 µg/ml), ciprofloxacin (at 2×MIC; 1.0 µg/ml), gentamicin (at ⅛ to ¹⁄₁₆×MIC; 0.06 µg/ml), and of the combination of gentamicin and tomatidine (TO) (at 0.06 and 8 µg/ml, respectively) on the growth and viability of the normal (i.e. non electron transport-deficient strain S. aureus ATCC 29213). The no drug control culture is also shown.

Results:

FIG. 8 shows that tomatidine greatly potentiates the bactericidal action of aminoglycosides such as gentamicin against "normal", non electron transport-deficient *S. aureus* ATCC 29213. Results show that while neither gentamicin nor tomatidine used alone at 0.06 or 8 respectively, had antibacterial activity on *S. aureus*, the combination of both provided a strong bactericidal activity; the combination killed *S. aureus* better and faster than the well-known bactericidal drug ciprofloxacin used at 2×MIC (1.0 µg/ml). The concentration of gentamicin used in the assay was 0.06 µg/ml, which represented only ⅛ to ¹⁄₁₆ of the MIC of the drug alone against *S. aureus* ATCC 29213.

EXAMPLE 14

Prevention of the Emergence of Bacteria with Decreased Susceptibility to Aminoglycoside Antibiotics with Steroid Alkaloid Compounds Regrowth of bacteria with reduced susceptibility to aminoglycosides is often observed within 24 hours following antibiotic exposure (Miller et al., 1978; Wilson and Sanders, 1976). The effect of compounds of the present invention on the emergence of bacteria with reduced susceptibility to aminoglycosides was determined. Bacteria were inoculated at ~$10^5$-$10^6$ CFU/ml in BHI or MHBCA in the absence or presence of antibiotics at the specified concentrations. At several time points during growth at 35° C., cultures were sampled, serially diluted and plated on TSA for CFU determinations.

Figure 9A:
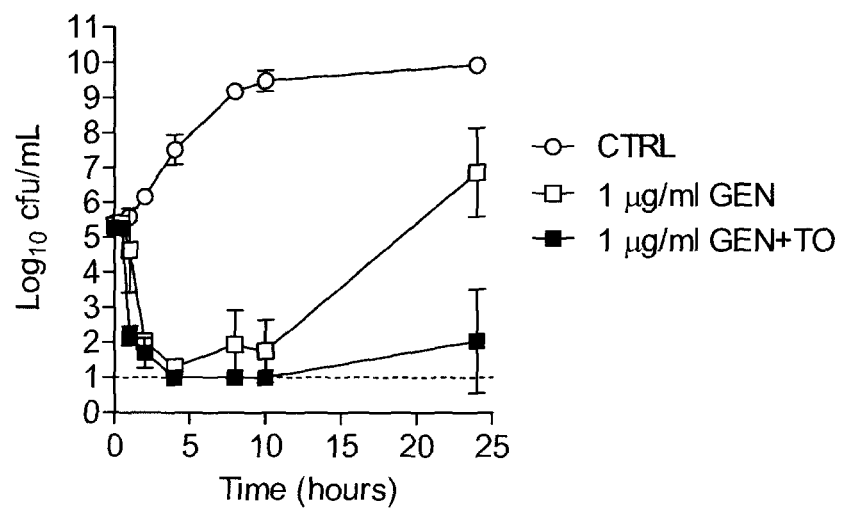
FIG. 9 shows the effect of (A) gentamicin (GEN) or (B) tobramycin (TOB) (at ~1×MIC; 1 µg/ml) alone or in combination with tomatidine (TO) (at 8 µg/ml) on the growth and viability of the strain S. aureus ATCC 29213. The no drug control culture (Ctrl) is also shown.
Figure 9B:
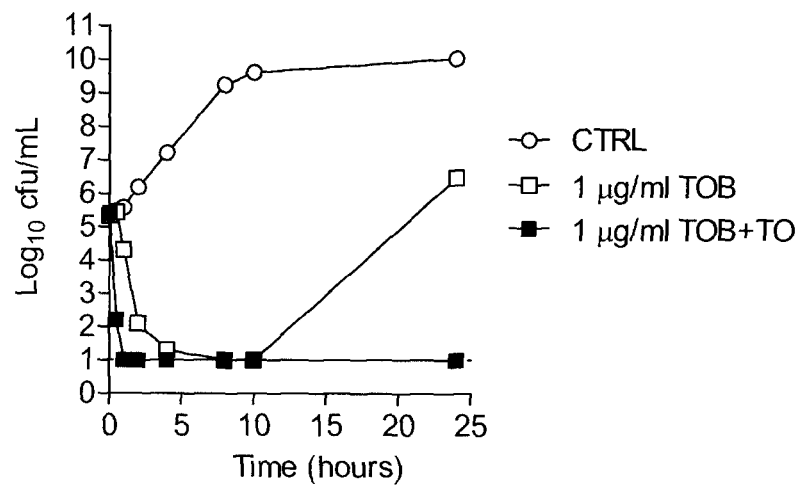
Figure 10:
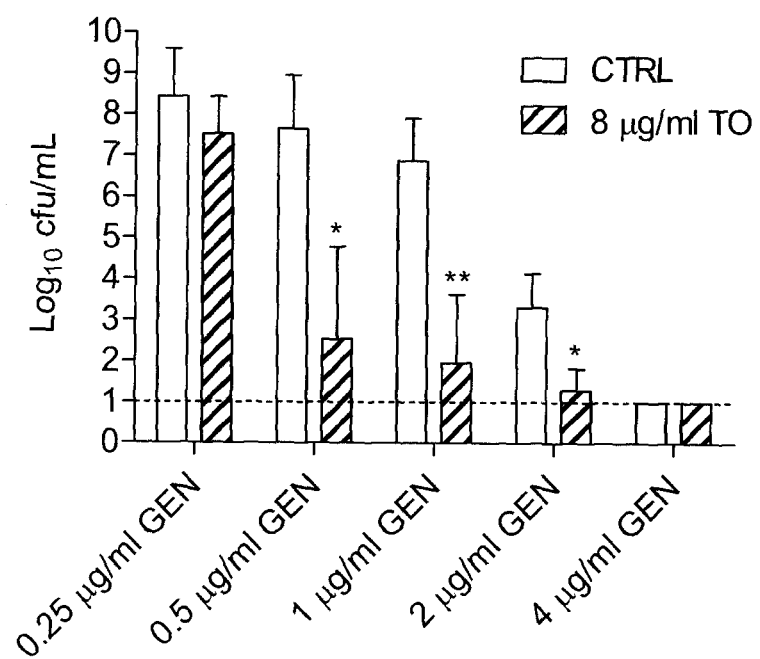
FIG. 10 shows the effect of gentamicin (GEN) at concentrations ranging from 0.25 to 4 µg/ml combined or not with 8 µg/ml of TO on the viability of 24 h cultures of the strain S. aureus ATCC 29213. Significant differences between the control (CTRL) and tomatidine (TO) conditions are shown (**P<0.01 and *P<0.05; unpaired t-test). Data are presented as means with standard deviations from at least two independent experiments.

Results:

FIGS. 9A and B show that gentamicin (GEN) and tobramycin (TOB) alone at ≥1×MIC (1 µg/ml) are bactericidal against *S. aureus* ATCC 29213 although, as anticipated for aminoglycosides, regrowth is observed within 24 h. Accordingly, colonies isolated from 24 h-cultures exposed to gentamicin were often normal-growing bacteria with a decreased susceptibility to gentamicin (MIC ranging from 1 to 4 µg/ml) or SCVs (MIC for gentamicin ranging from 4 to 8 µg/ml). Tomatidine (TO) at 8 µg/ml markedly reduced the regrowth of bacteria exposed to gentamicin (9A) or tobramycin (9B). FIG. 10 further demonstrated that the presence of tomatidine can significantly decrease the number of CFU recovered from cultures exposed to concentrations of gentamicin ranging from 0.5 to 4 µg/ml for 24 h. From these time-kill experiments, isolated colonies obtained from cultures exposed to gentamicin combined or not with 8 µg/ml tomatidine were analyzed for their susceptibility to gentamicin. When ATCC 29213 was exposed to gentamicin alone, the emergence of numerous normal-growing isolates showing decreased susceptibility to gentamicin (MIC ranging from 1 to 4 mg/L) was easily detected. The combination of tomatidine and gentamicin significantly reduced the emergence of such resistant CFU (FIG. 10).

EXAMPLE 15

Natural Steroid Alkaloids

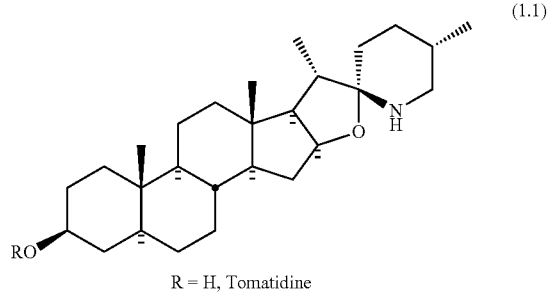

(1.1)

R = H, Tomatidine

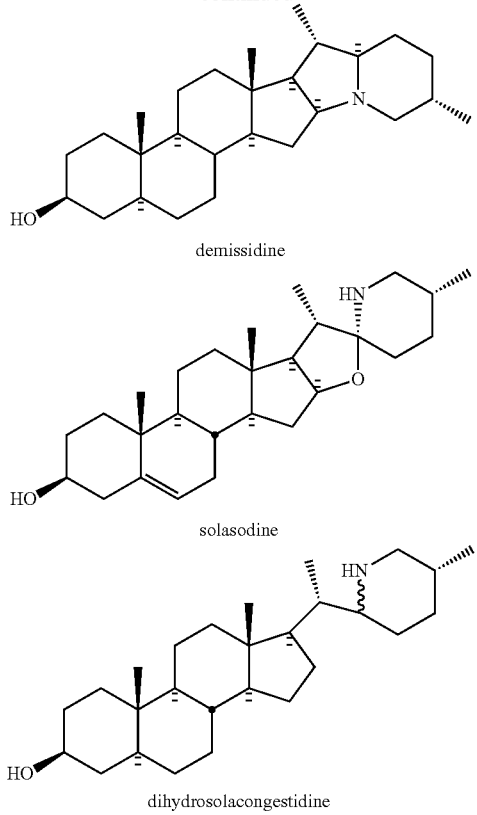

demissidine solasodine dihydrosolacongestidine

The compounds above (including tomatidine formula 1.1) are commercially available through Sigma-Aldrich, Acros or Molekula for example. Solasodan (see structure below) was purchased from Sigma.

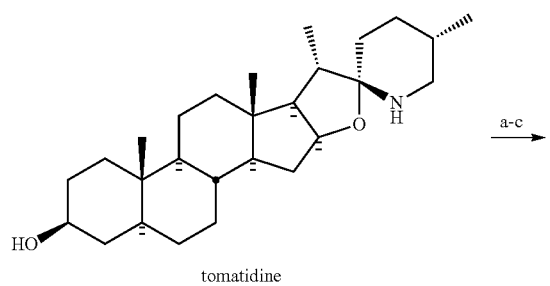

EXAMPLE 16

Synthesis of Tomatidine 3-Sulfate of Formula 1.0

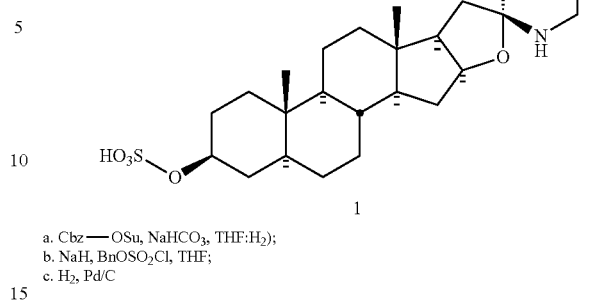

1 a. Cbz—OSu, NaHCO$_3$, THF:H$_2$);
b. NaH, BnOSO$_2$Cl, THF;
c. H$_2$, Pd/C

Tomatidine 3-sulfate 1 is synthesized in 3 steps by initially protecting the aminal via a carbobenzyloxy (Cbz) group in standard conditions. Subsequently, the free hydroxyl is sulphated using benzyloxy sulfuryl chloride and sodium hydride in THF. Finally, simultaneous hydrogenolysis of both benzyl groups will give the desired compound.

EXAMPLE 17

Synthesis of Tomatidine 3-Phosphate of Formula 1.0

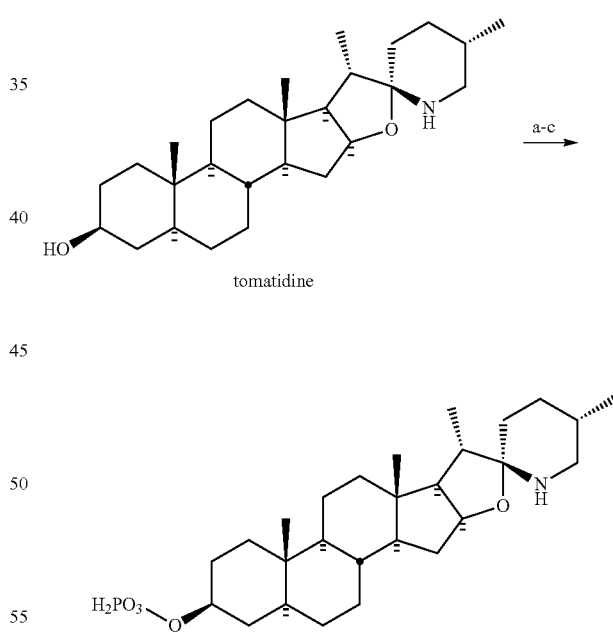

2 a. Cbz—OSu, NaHCO$_3$, THF:H$_2$);
b. NaH, (BnO)$_2$POCl, THF;
c. H$_2$, Pd/C

Tomatidine 3-phosphate 2 is synthesized in 3 steps by initially protecting the aminal via a Cbz group in standard conditions. Subsequently, the free hydroxyl is phosphorylated using bis(benzyloxy)phosphoryl chloride and sodium hydride in THF. Finally, simultaneous hydrogenolysis of both benzyl groups gives the desired compound.

EXAMPLE 18

Synthesis of 3-Substituted Tomatidine Analogues of Formula 1.0

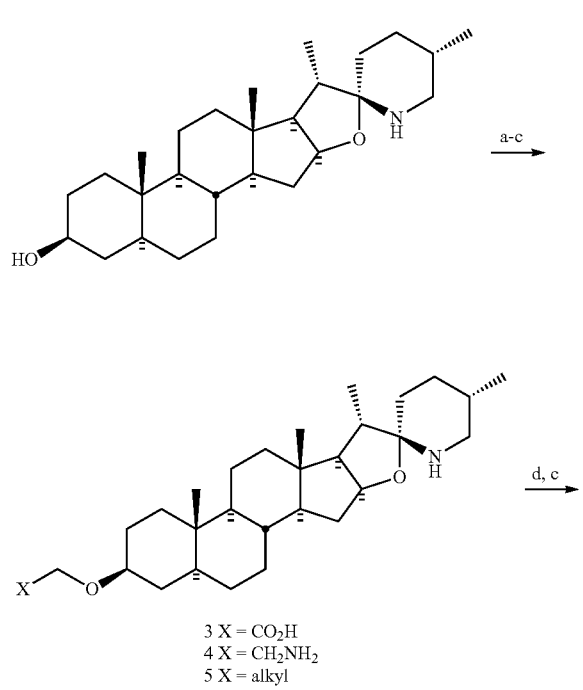

3 X = CO₂H
4 X = CH₂NH₂
5 X = alkyl

6 X = CH₂NHC(=NH)NH₂ a. Cbz—OSu, NaHCO₃, THF;
b. (i: 3): NaH, THF, BrCH₂CO₂Bn; (ii: 4) BrCH₂CH₂NHCO₂Bn, THF; (iii: 5) ICH₂alkyl, NaH, THF;
c. H₂, Pd/C;
d. CbzNH(C=NTf)NHCbz, DiPEA, DCM 3-substituted tomatidine analogs 3-5 are synthesized starting from tomatidine by initial Cbz protection of the hemiaminal portion of the molecule, followed by alkylation using sodium hydride and the required electrophile (benzyl chloroacetate for 3, Cbz-bromoethylamine for 4, iodoalkanes for 5). Subsequent hydrogenolysis of both protective groups delivers the desired compounds 3-5. Synthesis of 6 starts 4, which is reacted with Goodman's triflimide reagent. Subsequent hydrogenolysis delivers 6. Analogues bearing additional substitution on the amine moiety of 4 are synthesized by further functionalization of the primary amine using standard methods such as amide bond formation, sulfonylation or reductive amination.

EXAMPLE 19

Synthesis of 3α-hydroxytomatidine of Formula 1.0

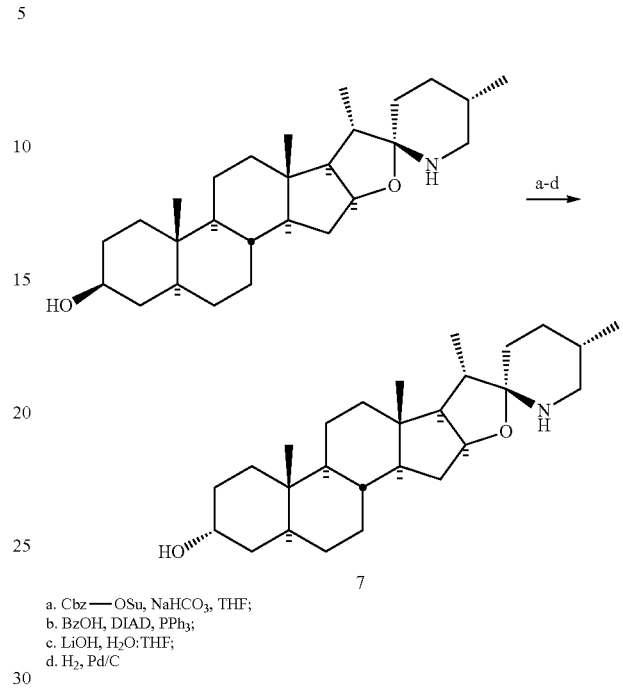

7 a. Cbz—OSu, NaHCO₃, THF;
b. BzOH, DIAD, PPh₃;
c. LiOH, H₂O:THF;
d. H₂, Pd/C

3α-hydroxytomatidine 7 is synthesized by initial protection of the amine group as described above in Example 16 followed by Mitsubobu reaction with benzoic acid, benzoate cleavage with lithium hydroxide then hydrogenolysis of the Cbz group.

EXAMPLE 20

Synthesis of 3-oxo-tomatidine and 3-aminotomatidine of Formula 1.0

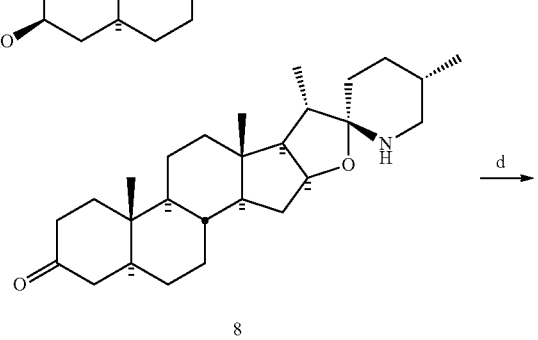

8

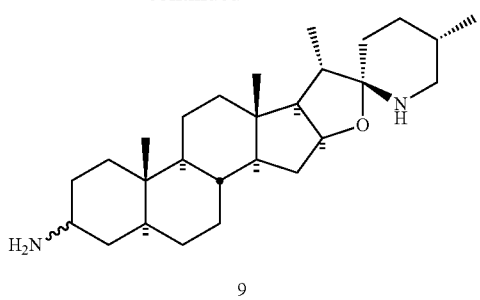

9 a. Cbz—OSu, NaHCO₃, THF;
b. Swern oxydation;
c. H₂, Pd/C;
d. (NH₄)₂CO₃, NaBH₃CN, MeOH

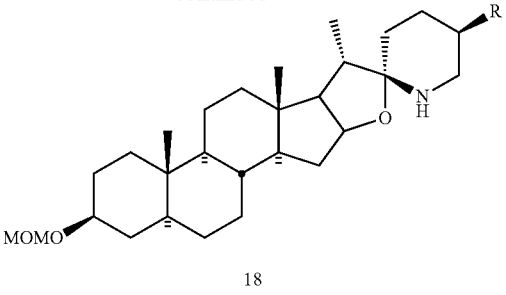

18 a. NBS, benzoyl peroxide, CCl₄;
b. DBU;
c. N-bromoacetamide, THF, H₂O;
d. BnOC(=NH)CCl₃, H⁺;
e. LDA, Comins' reagent;
f. R—C₅H₄NB(OH)₂, base, Pd(PPh₃)₄;
g. Et₃B, Bu₃SnH;
h. H₂, Pd/C;
i. HCl, EtOAc 3-oxo-tomatidine 8 is synthesized by protection of the amine group with a Cbz, followed by Swern oxidation of the alcohol and subsequent hydrogenolysis. 3-aminotomatidine 9 is obtained from 8 by reductive amination using ammonium carbonate and sodium cyanoborohydride.

EXAMPLE 21

Synthesis of Analogues 18 of Formula 1.0

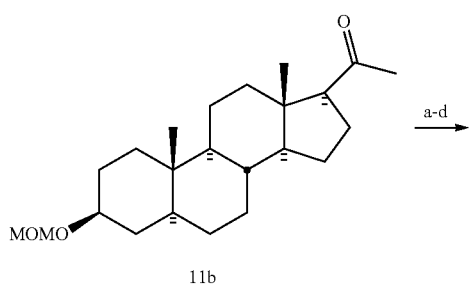

11b

Common intermediate 11b is first treated with NBS and benzoyl peroxide followed by base treatment to give the unsaturated ketone (Bolger et al., 1996). The latter undergoes bromination with N-bromoacetamide followed by opening of the bromonium ion with water (Li et al., 2009). Subsequent benzyl protection gives intermediate 17. Subsequently, the enol triflate is formed using Comins' reagent, then undergoes a Suzuki cross coupling with variously substituted pyridines. The bromide is then cleaved in reducing conditions, and the spirohemiaminal closed to give the desired analogues satisfying formula 18 having the alcohol in position 3 protected by a protective group methoxymethyl (MOM).

EXAMPLE 22

Synthesis of N-formyl tomatidine (21) of Formula 1.0

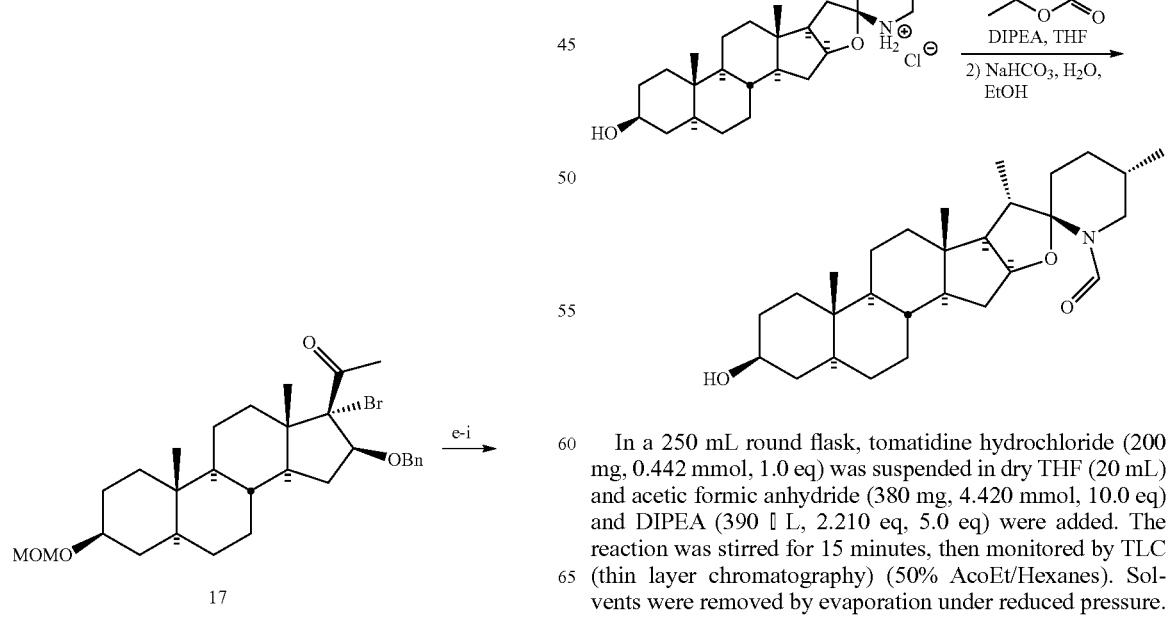

In a 250 mL round flask, tomatidine hydrochloride (200 mg, 0.442 mmol, 1.0 eq) was suspended in dry THF (20 mL) and acetic formic anhydride (380 mg, 4.420 mmol, 10.0 eq) and DIPEA (390 μL, 2.210 eq, 5.0 eq) were added. The reaction was stirred for 15 minutes, then monitored by TLC (thin layer chromatography) (50% AcOEt/Hexanes). Solvents were removed by evaporation under reduced pressure. The compound was then diluted in 125 mL EtOH and 50 mL of aqueous NaHCO₃ buffer (pH=9.5) and stirred for one week, monitored by TLC until complete disappearance of diformylated compound. EtOH was then evaporated, and the resulting aqueous phase was extracted with 3×25 mL AcOEt. The combined organic phases were dried on anhydrous MgSO₄ and evaporated under reduced pressure.

Crude product was purified by flash chromatography (25% AcOEt/Hexanes) to give 155 mg (79%) of the desired compound 21.

¹H NMR (300 MHz, CDCl₃) δ (ppm) 8.41 (s, 1H), 4.29 (d, 1H, J=11.5 Hz), 4.13 (dd., 1H, J₁=7.3 Hz, J₂=15.5 Hz), 3.58 (quint, 1H, J=4.7 Hz), 2.65 (t, 1H, J=11.5), 7.1 (quint, 1H, J=7.1 Hz), 1.9 (quint, 1H, J=5.28 Hz) 1.87 (d, 1H, J=13.7 Hz), 1.82-1.72 (m, 3H), 1.72-1.63 (m, 3H), 1.61-1.45 (m, 7H), 1.40 (d, 1H, J=13.0 Hz), 1.38-1.22 (m, 8H), 1.15 (dt, 1H, J₁=12.3 Hz, J₂=3.9 Hz), 1.12-1.06 (m, 2H), 1.05 (d, 3H, J=6.8 Hz), 0.95 (dt, 1H, J₁=13.7 Hz, J₂=3.6 Hz), 0.91 (d, 3H, J=5.9 Hz), 0.89-0.84 (m, 1H), 0.82 (s, 6H), 0.64 (dt, 1H, J₁=11.39, J₂=3.6 Hz). HRMS calculated for $C_{28}H_{45}O_3N$: 443.6618, calculated for MNa⁺: 466.6510. found: 466.3308 (MNa⁺).

EXAMPLE 23

Synthesis of N-formyl-3α-acetyltomatidine (22) of Formula 1.0

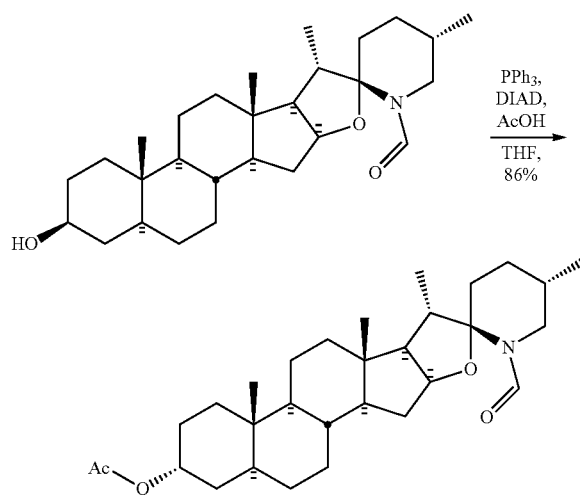

In a 10 mL round bottom flask, N-formyl tomatidine (1) (60 mg, 0.135 mmol, 1.0 eq) was dissolved in 3 mL anhydrous THF, along with triphenylphosphine (71 mg, 0.270 mmol, 2.0 eq) and acetic acid (22 µL, 378 eq, 2.8 eq). Diisopropylazodicarboxylate (40 µL, 202 mmol, 1.5 eq) was added, and the reaction was stirred at room temperature for 4 h, monitored by TLC (25% AcOEt/hexanes, rf: 0.10 (uv). An additional 20 µL DIAD, 30 mg PPh₃ and 20 µL of acetic acid were added to drive the reaction to completion, and the reaction was stirred overnight. The reaction was then concentrated under reduced pressure, suspended in water and extracted 3× with AcOEt. The combined organic fractions were washed with brine, dried on anhydrous MgSO₄ and evaporated under reduced pressure. The crude compound was purified by flash chromatography (10% AcOEt/hexanes) and 56 mg (86%) of compound 22 were obtained.

¹H NMR (300 MHz, CDCl₃) δ (ppm) 8.43 (s, 1H), 5.00 (m, 3H, DIAD) 4.31 (d, 1H, J=11.8 Hz), 4.99 (m, 1H), 4.16 (quad, 1H, J=7.1 Hz), 2.68 (t, 1H, J=12.1 Hz), 2.56 (s, 4H), 2.08-1.98 (m, 5H), 1.90 (d, 1H, J=12.4 Hz), 1.84-1.74 (m, 3H), 1.74-1.51 (m, 5H), 1.48 (s, 4H), 1.42-1.20 (m, 25H, DIAD), 1.14 (d, 2H, J=4.7 Hz), 1.08 (d, 3H, J=7.1 Hz), 0.93 (d, 4H, J=6.0 Hz), 0.85 (s, 3H), 0.83 (s, 3H), 0.81-0.73 (dt, 1H, J₁=11.5 Hz, J₂=3.3 Hz).

EXAMPLE 24

Synthesis of 3α-hydroxytomatidine hydrochloride Salt (23) of Formula 1.0

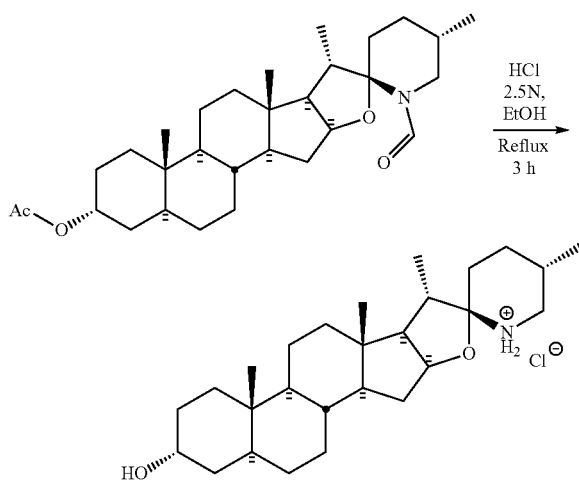

In a 25 mL round flask, 28 mg 22 (0.058 mmol) was refluxed for 3 hours in 6 mL EtOH and 3 mL aquous HCl 2.5 N. Upon completion, the ethanol and HCL were removed under reduced pressure and the remaining water was removed by lyophilization. Compound 23 was obtained as the hydrochloride salt of compound 7 (free base).

¹H NMR (300 MHz, CD₃OD) δ (ppm) 4.40 (quad, 1H, J=8.8 Hz), 3.98 (s large, 1H), 3.56 (m, 1H), 3.14 (t, 1H, J=12.6 Hz), 2.94 (t, 1H, J=11.0 Hz), 2.23 (t, 1H, J=6.0 Hz), 2.13-1.99 (m, 2H), 1.91 (t, 1H, J=7.1 Hz), 1.85-1.54 (m, 8H), 1.54-1.37 (m, 6H), 1.36-1.18 (s large, 21H), 1.12 (d, 3H, J=6.6 Hz), 1.01 (d, 3H, J=6.0 Hz), 0.93 (s, 3H), 0.86 (s large, 5H).

¹³C NMR (75.5 MHz, CD₃OD) δ (ppm) 96.2 (s), 81.1 (s), 69.1 (s), 66.9 (s), 65.7 (s), 65.4 (s), 61.7 (s), 55.6 (s), 54.2 (s), 48-46 (m, CD₃OD) 40.8 (s), 38.8 (s), 35.8 (s), 35.3 (s), 34.9 (s), 32.0 (s), 28.1 (s), 25.8 (s), 25.3 (s), 20.1 (s), 20.0 (s), 17.3 (s).

EXAMPLE 25

Synthesis of N-formyl-3-oxotomatidine (24) of Formula 1.0

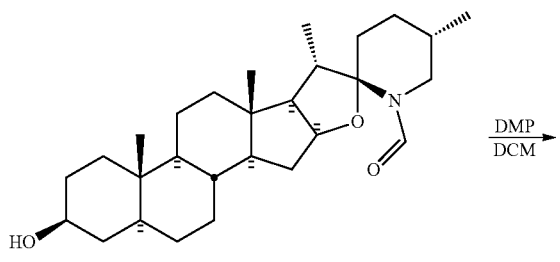

-continued

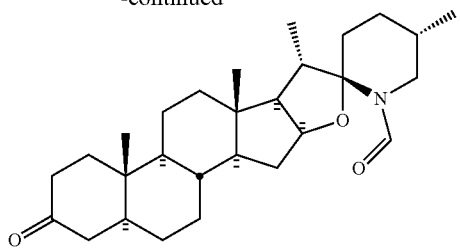

In a 10 mL round bottom flask, N-formyltomatidine 21 (50 mg, 0.113 mmol, 1.0 eq) and Dess-Martin periodinane (95 mg, 0.225 mmol, 2.0 eq) were stirred in 6.5 mL DCM. The reaction was monitored by TLC (50% AcOEt/Hexanes). Upon completion, the reaction was quenched for 30 minutes with $Na_2S_2O_3$ 0.2M, then extracted 3× with AcOEt. The combined organic phases were washed with brine, dried on anhydrous $MgSO_4$ and evaporated under reduced pressure. The crude compound was purified by flash chromatography (50% AcOEt/Hexanes) to yield 34 mg (68%) of desired compound 24.

$^1$H NMR (300 MHz, $CD_3OD$) δ (ppm) 8.46 ppm (s, 1H), 4.32 (d, 1H, J=12.8 Hz), 4.17 (quad, 1H, J=8.9 Hz), 2.69 (t, 1H, J=12.6 Hz), 2.58 (quint, 1H, J=6.6 Hz), 2.52-2.24 (m, 3H), 2.16-2.11 (m, 1H), 2.11-1.98 (m, 2H), 1.91 (d, 1H, J=14.0 Hz), 1.86-1.68 (m, 3H), 1.69-1.47 (m, 6H), 1.47-1.29 (m, 6H), 1.29-1.23 (m, 1H), 1.21 (s, 3H), 1.19-1.12 (m, 2H), 1.09 (d, 3H. J=7.1 Hz), 1.05 (s, 2H), 0.94 (d, 4H, J=5.5 Hz), 0.88 (s, 3H), 0.77 (dd, 1H, $J_1$=10.4 Hz, $J_2$=4.4 Hz).

EXAMPLE 26

Synthesis of 3-oxotomatidine hydrochloride Salt (25) of Formula 1.0

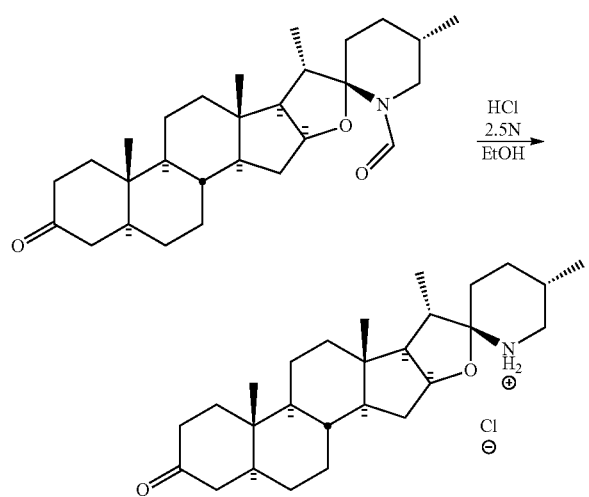

In a 25 mL round flask, 34 mg 22 (0.077 mmol) was refluxed for 2 hours in 10 mL EtOH and 5 mL aquous HCl 2.5 N. Upon completion, the ethanol and HCL were removed under reduced pressure and the remaining water was removed by lyophilization. Compound 25 was obtained as the hydrochloride salt of compound 8 (free base).

$^1$H NMR (300 MHz, $CD_3OD$) δ (ppm) 4.37 (quad, 1H, J=9.0 Hz), 3.11 (d, 2H, J=15.0 Hz), 2.89 (t, 1H, J=12.0 Hz), 2.53-2.30 (m, 1H), 2.24-2.14 (m, 1H), 2.08-1.94 (m, 3H), 1.91-1.63 (m, 7H), 1.63-1.50 (m, 5H), 1.49-1.15 (m, 12H), 1.10 (s, 2H), 1.06 (d, 3H, J=7.1 Hz), 0.96 (d, 3H, J=5.5 Hz), 0.89 (s, 3H), 0.82 (s, 3H), 0.76-0.66 (m, 1H).

$^{13}$C NMR (75.5 MHz, $CD_3OD$) δ (ppm) 100.2 (s), 96.1 (s), 81.1 (s), 61.7 (s), 55.5 (s). 54.1 (s), 42.2 (s), 40.8 (s), 40.7 (s), 39.6 (s), 35.5 (s), 34.9 (s), 34.8 (s), 32.0 (s), 31.4 (s), 28.2 (s), 28.1 (s), 27.9 (s), 25.7 (s), 25.3 (s), 20.7 (s), 17.2 (s), 15.9 (s), 13.2 (s), 10.6 (s), 10.5 (s).

EXAMPLE 27

Synthesis of O-allyl-N-formyltomatidine (55) of Formula 1.0

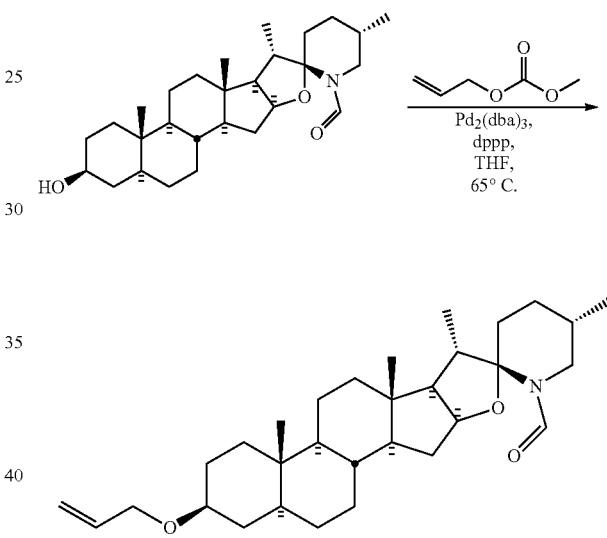

In a 3 mL round bottom flask equipped with a condenser tube and placed under argon atmosphere, compound 21 (30 mg, 0.068 mmol) was dissolved in 1 mL THF. $Pd_2(dba)_3$ (3 mg, 0.003 mmol, 0.005 eq), 1,3-bis(diphenylphosphino) propane (5 mg, 0.012 mmol, 0.18 eq) and allyl methyl carbonate (0.2 mL, 1.76 eq, 26 eq) were successively added. The reaction was brought to 65° C. for 6H, monitored by TLC. (50% AcOEt/hexanes). Upon completion, the reaction was allowed to cool to room temperature, then the solvent was removed in vacuo. The crude compound was purified by flash chromatography (20% AcOEt/Hexanes) to yield 25 mg (76%) of desired compound 55.

$^1$H NMR (300 MHz, $CDCl_3$) δ (ppm) 8.41 (s, 1H), 5.93 (ddt, 1H, $J_1$=17.3 Hz, $J_2$=10.5 Hz, $J_3$=5.7 Hz), 5.34 (d quad, 1H, $J_1$=17.1 Hz, $J_2$=1.4 Hz), 1.25 (d quad, 1H, $J_1$=10.3 Hz, $J_2$=1.3 Hz), 4.60 (dt, 2H, $J_1$=5.8 Hz, $J_2$=1.4 Hz), 4.53 (quint, 1H, J=5.5 Hz), 4.29 (d, 1H, J=11.9 Hz), 4.16-4.08 (m, 2H), 2.65 (t, 1H, J=11.3 Hz), 2.54 (t, 1H, J=7.0 Hz), 2.01-1.94 (m, 1H), 1.94-1.84 (m, 2H), 1.81-1.68 (m, 4H), 1.65 (s, 2H), 1.62-1.47 (m, 6H), 1.46-1.35 (m, 2H) 1.35-1.28 (m, 41H) 1.25 (t, 3H, J=7.3 Hz), 1.22-1.08 (m, 2H), 1.05 (d, 3H, J=7.0 Hz), 1.02-0.92 (m, 2H), 0.90 (d, 4H, J=5.8 Hz), 0.83 (s, 3H), 0.82 (s, 1H), 0.65 (dt, 1H, $J_1$=10.7 Hz, $J_2$=4.3 Hz).

EXAMPLE 28

Synthesis of O-allyltomatidine hydrochloride Salt (56) of Formula 1.0

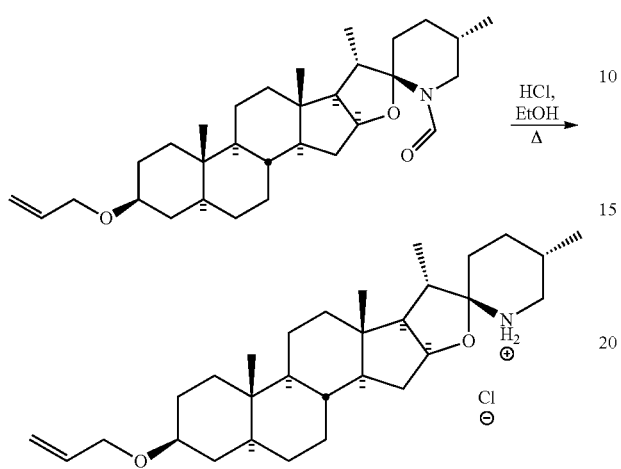

In a 20 mL vial, 55 (8.7 mg, 0.018 mmol), was dissolved in 10 mL EtOH and 3 mL conc. HCl. The mixture was brought to 65° C. for 1H, then solvent was removed in vacuo. The remaining water was lyophilized to yield 7.9 mg (90%) of crude compound 56.

$^1$H NMR (300 MHz, CD$_3$OD) δ (ppm) 5.96-5.82 (m, 1H), 5.28 (d, 1H, J=17.1 Hz), 5.18 (d, 1H, J=10.4 Hz), 4.53 (d, 2H, J=5.9 Hz), 4.47 (m, 1H), 4.36 (m, 1H), 3.58-3.42 (m, 1H), 3.15-3.04 (m, 1H), 2.87 (t, 1H, J=11.7 Hz), 2.76-2.58 (m, 1H), 2.38-2.26 (m, 1H), 2.21-1.90 (m, 4H), 1.84 (d, 2H, J=11.1 Hz), 1.78-1.44 (m, 12H), 1.40-1.10 (m, 15H), 1.09-1.92 (m, 8H), 0.87 (s, 2H), 0.86-0.79 (m, 5H), 0.75-0.57 (m, 4H).

EXAMPLE 29

Synthesis of tomatidine methanesulfonate (57) of Formula 1.0

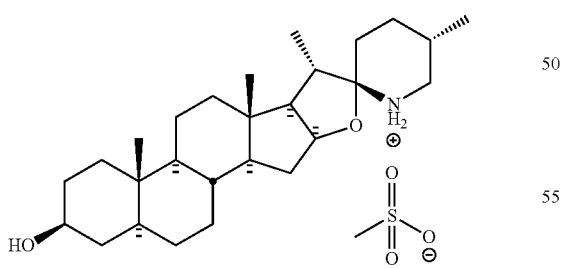

In a 25 mL round bottom flask, tomatidine (60 mg, 0.132 mmol) was suspended in 15 mL EtOH along with silver oxide (60 mg). The mixture was mixed in a sonic bath for 1H, then filtered on diatomaceous earth pad to yield 50 mg (91%) of tomatidine free base (formula 1.1, R=H).

In a 20 mL vial, 21.5 mg (0.052 mmol) of tomatidine free base was solubilised in THF. 63 µL of a solution of methanesulfonic acid 1M in THF was added (1.2 eq), and the mixture was stirred for 5 minutes. Solvent was removed in vacuo to yield 20 mg (75%) of desired compound 57.

$^1$H NMR (300 MHz, CD$_3$OD) δ (ppm) 4.37 ppm (quad, 1H, J=7.2 Hz), 3.73-3.67 (m, 1H), 4.52-3.42 (m, 1H), 3.12 (d, 1H, J=12.5 Hz), 2.89 (t, 1H, J=12.3 Hz), 2.69 (s, 3H), 2.37 (t, 1H, J=7.2 Hz), 2.24-2.13 (m, 1H), 2.08-1.96 (m, 2H), 1.90-1.81 (m, 2H), 1.78-1.64 (m, 5H), 1.63-1.42 (m, 4H), 1.40-1.32 (m, 7H), 1.31-1.13 (m, 7H), 1.08 (d, 3H, J=7.2 Hz), 0.96 (d, 3H, J=6.5 Hz), 0.89 (s, 3H), 0.84 (s, 3H), 0.74-0.62 (m, 1H).

EXAMPLE 30

Synthesis of tomatidine citrate (58) of Formula 1.0

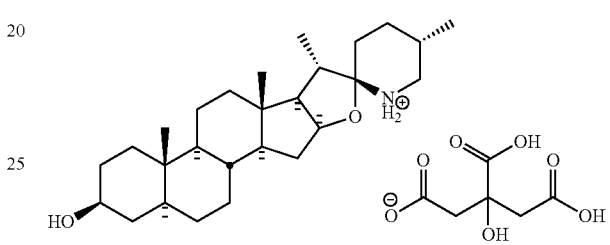

In a 25 mL round bottom flask, tomatidine (60 mg, 0.132 mmol) was suspended in 15 mL EtOH along with silver oxide (60 mg). The mixture was mixed in a sonic bath for 1H, then filtered on diatomaceous earth pad to yield 50 mg (91%) of tomatidine free base (formula 1.1, R=H).

In a 20 mL vial, 27 mg (0.065 mmol) of tomatidine free base was solubilised in THF. 235 µL of a solution of citric acid, 0.33M in THF was added (1.2 eq), and the mixture was stirred for 5 minutes. Solvent was removed in vacuo to yield 30 mg (76%) of desired compound 58.

$^1$H NMR (300 MHz, CD$_3$OD) δ (ppm) 4.40-4.29 (m, 1H), 3.54-3.39 (m, 2H), 3.22-3.10 (s large, 1H), 1.93-2.83 (m, 1H), 2.78 (quad, 10H, J=14.5 Hz), 2.33 (t, 1H, J=8.1 Hz), 2.07-1.95 (m, 3H), 1.88-1.80 (m, 12H), 1.79-1.63 (m, 8H), 1.62-1.45 (m, 5H), 1.38 (s, 15H), 1.30-1.24 (m, 4H), 1.24-1.05 (m, 9H), 1.00-0.90 (m, 6H), 0.89 (s, 4H), 0.84 (s, 4H), 0.68 (dt, 1H, J$_1$=11.8 Hz, J$_2$=4.5 Hz).

EXAMPLE 31

Synthesis of Common Intermediate 11

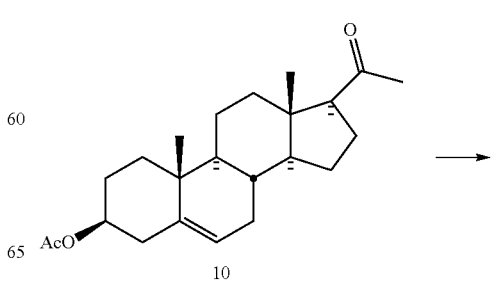

71

-continued

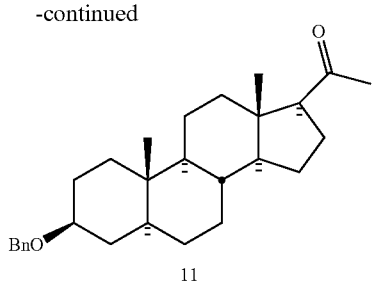

11 a. H₂, Pd/C, EtOH; b. NaOH, MeOH:H₂O; c. BnOC(=NH)CCl₃, TfOH, DCM

Intermediate 11 is synthesized from pregnenolone acetate, starting with hydrogenation that delivered the reduced product. Subsequent methanolysis of the acetyl group with methanolic sodium hydroxide was followed by benzylation using benzyl trichloroacetimidate and triflic acid, delivering intermediate 11.

EXAMPLE 32

Synthesis of Heterocyclic Analogues 12a, 12b and 13 of Formula 2.0

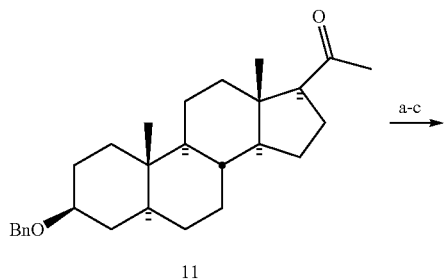

11

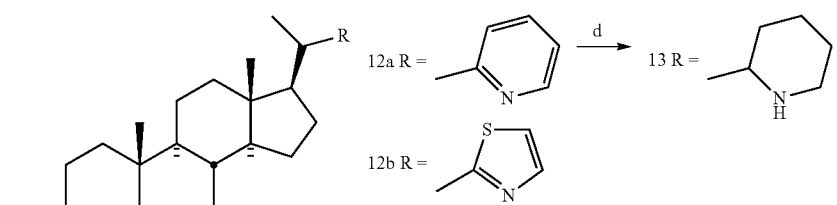

a. NaH, Comins' reagent;
b. heteroarylboronic acid, Pd(PPh₃)₄, base;
c. H₂, Pd/C;
d. H₂, PtO₂, 1000 psi Synthesis of heterocyclic analogues starts from common intermediate 11. Initial formation of the triflylenol using Comins' reagent followed by Suzuki cross-coupling with pyridineboronic acid using a palladium catalyst and subsequent hydrogenation of the double bond gives pyridine analogue 12a. Analogous derivatives with either alternative branching on the pyridine ring or additional substituents on pyridine are synthesized by the same method. Thiazole-substituted analogues 12b are synthesized using the same sequence with a cross-coupling with 2-thiazolylboronic acid. Piperidine derivatives 13 are obtained by high pressure hydrogenation of the pyridine derivative using platinum oxide.

72

EXAMPLE 33

Synthesis of Analogue 20 of Formula 2.0

Intermediate 11b is first treated with NBS and benzoyl peroxide followed by base treatment to give the unsaturated ketone (Bolger et al., 1996). The latter undergoes bromination with N-bromoacetamide followed by opening of the bromonium ion with water (Li et al., 2009). Subsequent methyl protection leads to intermediate 19. Subsequent transformations yields analogue 20 in which ring the E of tomatidine is open.

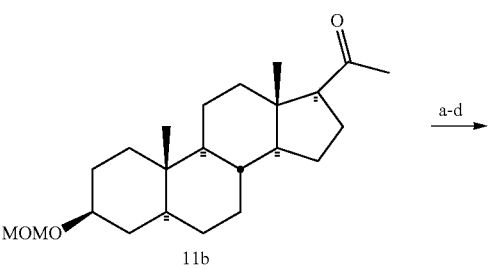

11b

-continued

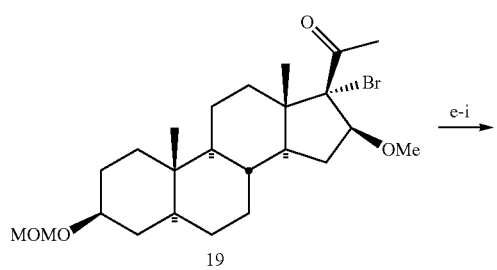

19

-continued

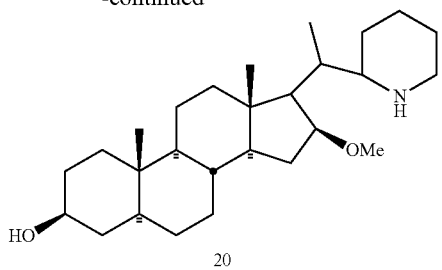
20 a. NBS, benzoyl peroxide, CCl₄; b. DBU; c. N-bromoacetamide, THF, H₂O; d. BnOC(=NH)CCl₃, H⁺; e. LDA, Comins' reagent; f. R—C₅H₄NB(OH)₂, base, Pd(PPh₃)₄; g. Et₃B, Bu₃SnH; h. H₂, Pd/C; i. HCl, EtOAc.

Pregnenolone Acetate Derivatives

EXAMPLE 34

Synthesis of O-acetyl-N-benzylpregn-5,6-en-3β-ol-20-amine (29a, 29b) of Formula 2.0

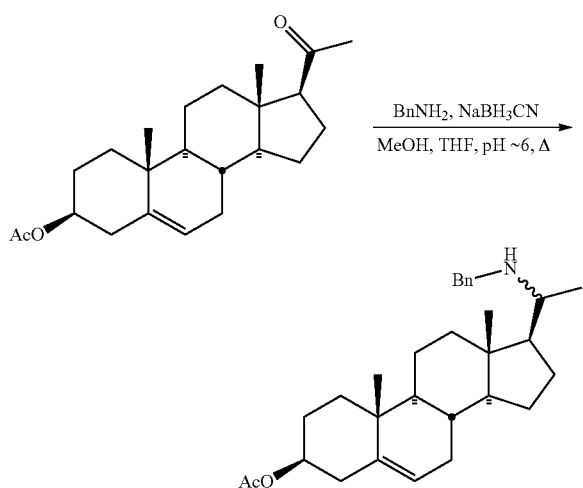

In a 25 mL round bottom flask equipped with a condenser tube, pregnenolone acetate (200 mg, 0.558 mmol) and benzylamine (366 μL, 3.347 mmol, 6.0 eq) were dissolved in 10 mL anhydrous MeOH. pH was set to with conc. acetic acid, and 10 mL anhydrous THF was added. NaBH₃CN (39 mg, 0.614 mmol, 1.1 eq) was added before the reaction was heated to reflux and stirred overnight. The next day, the reaction was monitored by TLC (25% AcOEt/Hexanes, UV/CAM, rf: 0.46 (starting material), 0.07 and 0.04 (desired compound)). The solvents were removed under reduced pressure, and the material was suspended in water. The pH was adjusted to 8 with saturated aqous NaHCO₃, then the mixture was extracted 3× with DCM. The combined organic fractions were washed with brine, dried on anhydrous MgSO₄ and the solvent was removed under reduced pressure. The crude compound was purified by flash chromatography (50% AcOEt/Hexanes) to yield 122 mg (48%) and 79 mg (32%) of each diastereisomer of the desired compound 29. The absolute stereochemistry of each compound was not identified.

$^1$H NMR (300 MHz, CD₃OH) δ (ppm) 7.34-7.21 (m, 5H), 5.36 (d, 1H, J=4.8 Hz), 3.76 (dd, 2H, J₁=80.6 Hz, J₂=12.9 Hz), 2.62 (dt, 1H, J₁=15.6 Hz, J₂=9.5 Hz), 2.31 (d, 2H, J=7.1 Hz), 2.08 (dt, 1H, J₁=12.0 Hz, J₂=3.1 Hz), 2.02 (s, 3H) 2.01-1.74 (m, 4H), 1.65-1.07 (m, 12H), 1.05 (d, 4H, J=6.1 Hz), 1.01 (s, 4H), 0.65 (s, 3H).

EXAMPLE 35

Synthesis of pregnan-3β-ol-20-amine (30a, 30b) of Formula 2.0

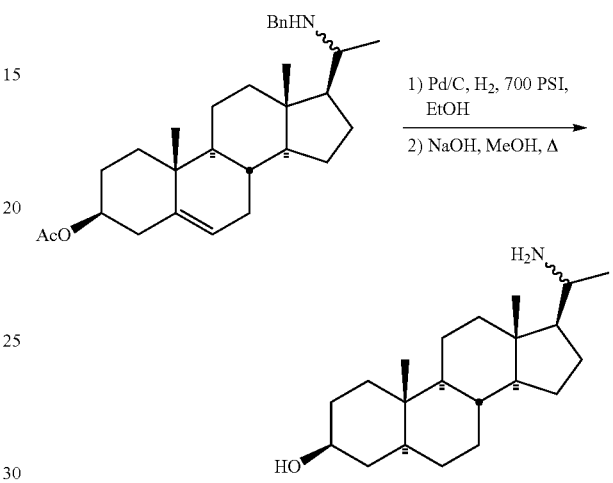

In two separate 20 mL vials, 29a and 29b (20 mg each, 0.080 mmol) were dissolved in 3 mL EtOH. Pd/C 10% w/w was added and the vials were placed under 700 PSI of hydrogen in a hydrogenation bomb overnight. The following morning, the compounds were filtered on diatomaceous earth pad and the solvent was evaporated under reduced pressure.

The compounds were then refluxed in 5 mL MeOH and 2 mL NaOH 1M for 1 h. MeOH was evaporated under reduced pressure, then wather was added to give a white solid which was isolated by filtration to yield 2 mg of 30a and 1.5 mg of 30b.

$^1$H NMR (300 MHz, CD₃OH) δ (ppm) 3.59 (sept, 1H, J=5 Hz), 2.89-2.79 (m, 1H), 1.99-1.90 (m, 1H), 1.80 (d, 1H, J=13.3 Hz), 1.75-1.62 (m, 3H), 1.60-1.48 (s large, 18H), 1.43-1.20 (m, 8H), 1.19-1.02 (m, 5H), 0.99 (d, 4H, J=5.7 Hz), 0.95-0.83 (m, 2H), 0.81 (s, 3H), 0.72 (s) 0.69-0.63 (m, 1H).

EXAMPLE 36

Synthesis of O-acetylpregn-5,6-en-3β-ol-20-((N,N-dimethylamino)propyl)amine (31) of Formula 2.0

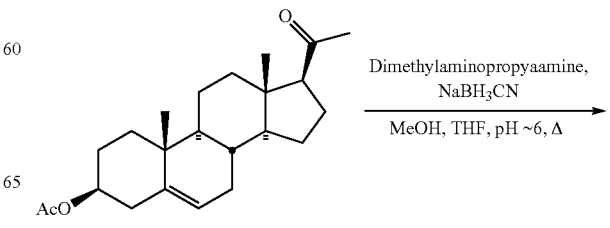

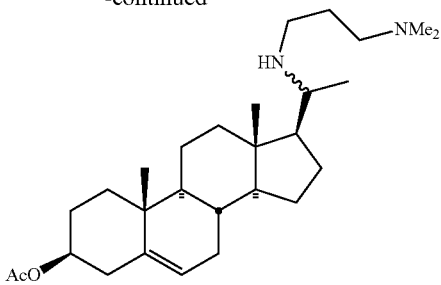

In a 25 mL round bottom flask equipped with a condenser tube, pregnenolone acetate (200 mg, 0.558 mmol) and N,N-dimethylaminopropylamine (421 µL, 3.347 mmol, 6.0 eq) were dissolved in 10 mL anhydrous MeOH. pH was set to ≈6 with conc. acetic acid, and 10 mL anhydrous THF was added. NaBH$_3$.CN (39 mg, 0.614 mmol, 1.1 eq) was added then the reaction was heated to reflux and stirred overnight. The next day, the reaction was monitored by TLC (75% AcOEt/Hexanes). The solvents were removed under reduced pressure, and the material was suspended in water. pH was adjusted to 8 with saturated aqueous NaHCO$_3$, then the mixture was extracted 3× with DCM. The combined organic fractions were washed with brine, dried on anhydrous MgSO$_4$ and the solvent was removed under reduced pressure. The crude compound 31 (141 mg, 57%) was used without further purification.

$^1$H NMR (300 MHz, CDCl$_3$) δ (ppm) 5.90-5.60 (s large, 3H), 5.27 (d, 1H, J=4.9 Hz), 5.22 (t, 1H, J=3.1 Hz), 4.55-4.43 (m, 1H), 3.31-3.12 (m, 1H), 2.97-2.32 (m, 5H), 2.22 (s, 3H), 2.17 (m, 4H), 1.93 (s, 3H), 1.87-1.69 (m, 6H), 1.68-1.54 (m, 4H), 1.52-1.29 (m, 8H), 1.27 (d, 3H, J=6.3 Hz), 1.24-1.17 (m, 2H), 1.14 (d, 3H, J=5.5 Hz), 1.11 (s, 1H), 1.09-0.98 (m, 3H), 0.94-0.88 (m, 4H) 0.78-0.74 (m, 1H), 0.65 (s, 2H), 0.62 (s, 1H).

EXAMPLE 37

Synthesis of pregnan-3β-ol-20-((N,N-dimethylamino)propyl)amine (32) of Formula 2.0

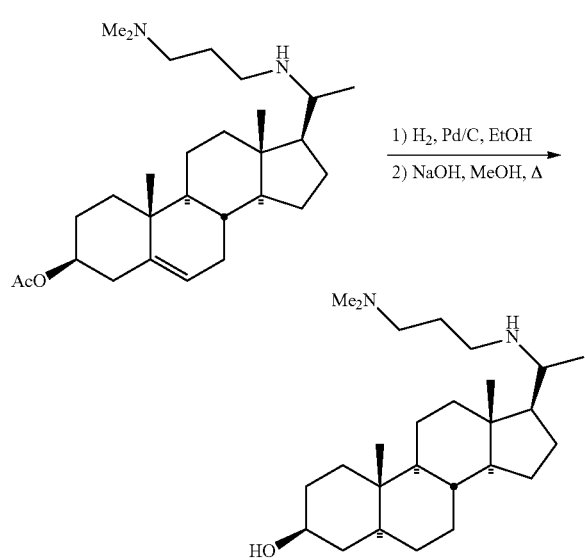

In a 50 mL round bottom flask, 31 (40 mg 0.090 mmol) was dissolved in 20 mL EtOH. Pd/C 10% w/w was added and the solution was placed under 700 PSI of hydrogen in a hydrogenation bomb for 6 h. The mixture was filtered on diatomaceous earth pad and the solvent was evaporated under reduced pressure.

The compound was then refluxed in 15 mL MeOH and 6 mL NaOH 1M for 1 h. MeOH was evaporated under reduced pressure, then water was added to give a white solid which was isolated by filtration to yield 18 mg (50%) of the desired compound 32.

$^1$H NMR (300 MHz, CDCl$_3$) δ (ppm) 3.58 (sept, 1H, J=7.6 Hz), 2.80-2.68 (m, 1H), 2.59-2.37 (m, 2H), 2.34-2.28 (m, 2H), 2.20 (s, 6H), 1.99-1.43 (m, 14H), 1.43-1.14 (m, 10H), 1.14-0.98 (m, 5H), 0.95 (d, 3H, J=5.8 Hz), 0.92-0.81 (m, 1H), 0.80 (s, 3H), 0.68 (s, 2H), 0.65 (s, 2H).

$^{13}$C NMR (75.5 MHz, CDCl$_3$) δ (ppm) 71.3 (s), 58.4 (s), 56.4 (s), 56.2 (s), 54.2 (s), 45.8 (s), 45.6 (s), 44.8 (s), 42.3 (s), 40.3 (s), 39.5 (s), 38.2 (s), 37.0 (s), 35.4 (s), 32.0 (s), 31.5 (s), 28.7 (s), 28.3 (s), 27.1 (s), 26.9 (s), 24.1 (s), 21.3 (s), 21.1 (s), 19.2 (s), 12.5 (s), 12.3.

EXAMPLE 38

General Procedure for Synthesis of Boc-diaminoalkanes (Boc=tert-butoxycarbonyle)

In a 5 mL round bottom flask, 11.5 mmol (10 eq) of desired diaminoalkane was solubilised in 2.5 mL DCM. A solution of (Boc)$_2$O (265 µL, 1.15 mmol, 1.0 eq) in 1 mL DCM was added dropwise. The resulting mixture was stirred for 24 h at room temperature, then washed with water, brine, then dried on anhydrous MgSO$_4$. The solvent was removed under reduced pressure to yield the desired compound (see also Mingyu Hu, 2011).

EXAMPLE 39

Synthesis of N-Boc-1,2-diaminoethane (33)

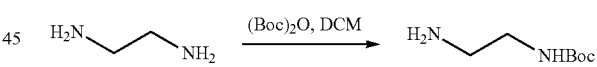

Following the procedure described in Example 38 above, 76 mg (41%) of desired compound 33 were obtained.

$^1$H NMR (300 MHz, CDCl$_3$) δ (ppm) 5.28-5.11 (s large, 1H), 3.13 (quad, 2H, J=5.7 Hz), 2.76 (t, 2H, J=5.7 Hz), 2.47-2.20 (s large, 2H), 1.38 (s, 9H).

EXAMPLE 40

Synthesis of N-Boc-1,3-diaminopropane (34)

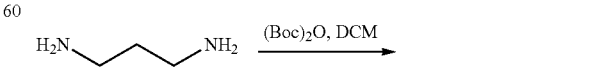

Following the procedure described in Example 38 above, 100 mg (50%) of desired compound 34 were obtained.

$^1$H NMR (300 MHz, CDCl$_3$) δ (ppm) 5.16 (s large, 1H), 3.60 (s large, 2H), 3.20 (quad, 2H, J=6.1 Hz), 2.83 (t, 2H, J=6.1 Hz), 1.69 (quint, 2H, J=6.1 Hz), 1.42 (s, 9H).

EXAMPLE 41

Synthesis of N-Boc-1,4-diaminobutane (35)

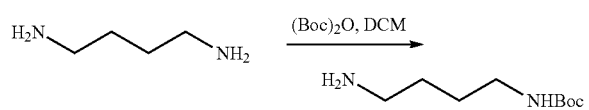

Following the procedure described in Example 38 above, 171 mg (79%) of desired product were obtained.

$^1$H NMR (300 MHz, CDCl$_3$) δ (ppm) 4.94 (s large, 1H), 3.04 (s large, 4H), 2.69 (s large, 2H), 1.45 (s large, 4H), 1.36 (s, 9H).

EXAMPLE 42

General Procedure for Reductive Amination with Pregnanolone Acetate

In a 25 mL round bottom flask equipped with a condenser tube, pregnenolone acetate (75 mg, 0.208 mmol) and corresponding amine (2-6 eq) were solubilised in 5 mL MeOH and pH was adjusted to 6 with conc. acetic acid. 5 mL THF were then added, followed by NaBH$_3$CN (15 mg, 0.230 mmol, 1.1 eq). The reaction was brought to reflux overnight and monitored by TLC. Solvents were removed under reduced pressure, and the solid was suspended in water and pH was adjusted to 8 with saturated aquous NaHCO$_3$. The mixture was extracted with 3×DCM, and the combined organic fractions were washed with brine, dried on anhydrous MgSO$_4$ and evaporated under reduced pressure. The crude compound was purified by flash chromatography (50% AcOEt/Hexanes then 10% MeOH/89% AcOEt/1% NEt$_3$).

EXAMPLE 43

Synthesis of O-acetylpregnan-3β-ol-20-(boc-aminoethyl)amine (36) of Formula 2.0

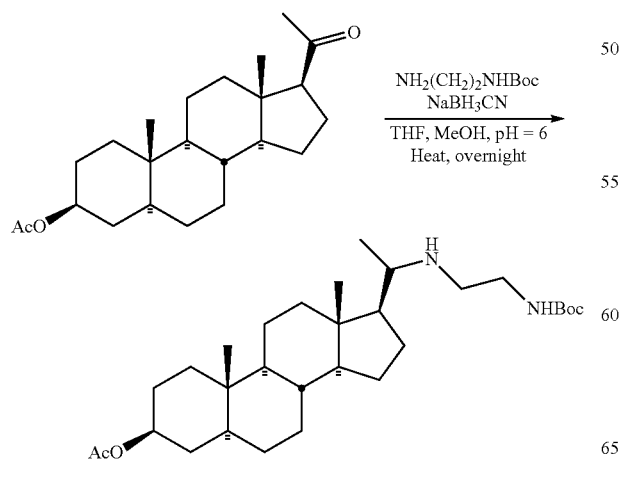

Following the procedure described in Example 42 above, 76 mg of compound 23 (0.474 mmol, 2.3 eq) was used to yield 84 mg (81%) of desired compound 36.

$^1$H NMR (300 MHz, CDCl$_3$) δ (ppm) 5.02 (d large, 1H), 4.66 (m, 1H, J=4.9 Hz), 3.27-3.05 (m, 2H), 2.85-2.68 (m, 1H), 2.65-2.45 (m, 3H), 2.03-1.92 (m, 4H), 1.88-1.51 (m, 7H), 1.47-1.35 (s large, 13H), 1.33-1.10 (m, 11H), 1.09-1.82 (m, 9H), 0.80 (s large, 4H), 0.69-0.55 d large, 4H).

EXAMPLE 44

Synthesis of O-acetylpregnan-3β-ol-20-(boc-aminopropyl)amine (37) of Formula 2.0

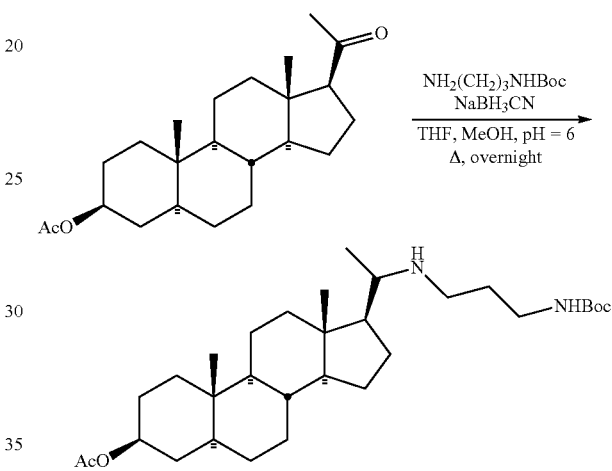

Following the procedure described in Example 42, 100 mg of compound 34 (0.574 mmol, 2.8 eq) was used to yield 51 mg (47%) of desired compound 37.

$^1$H NMR (300 MHz, CDCl$_3$) δ (ppm) 5.60 (s large, 0.2H) 5.07 (s large, 0.6H), 4.65 (sept, 1H, J=5.1 Hz), 3.16 (sept, 1H, J=3.6 Hz), 1.99 (s, 3H), 1.98-1.84 (m, 2H), 1.84-1.51 (m, 9H), 1.41 (s, 13H), 1.36-1.08 (m, 11H), 0.95 (d, 3H, J=6.1 Hz), 0.92-0.81 (m, 1H), 0.79 (s, 3H), 0.66 (s, 2H), 0.63 (s, 1H), 0.62-0.57 (m, 1H).

EXAMPLE 45

Synthesis of O-acetylpregnan-3β-ol-20-(boc-aminobutyl)amine (38) of Formula 2.0

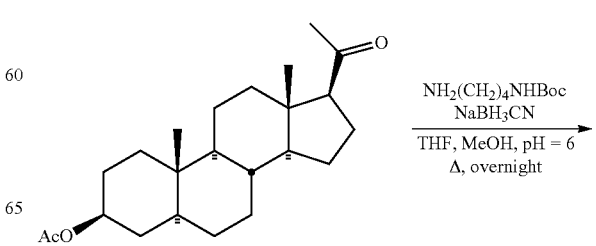

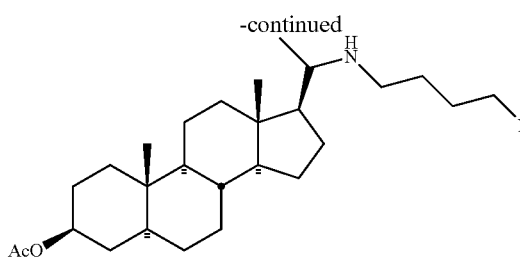

Following the procedure described in Example 42 above, 171 mg of compound 35 (0.908 mmol, 4.4 eq) was used to yield 70 mg (63%) of desired compound 38.

$^1$H NMR (300 MHz, CDCl$_3$) δ (ppm) 4.92 (d large), 4.65 (sept, 1H, J=6.2 Hz), 3.09 (s large, 2H), 2.78-2.52 (m, 2H), 2.52-2.38 (m, 1H), 1.99 (s, 3H), 1.95-1.84 (m, 1H), 1.82-1.45 (m, 10H), 1.41 (s, 10H), 1.35-1.10 (m 10H), 1.05-1.10 (m, 1H) 0.97 (d, 3H, J-5.7 Hz), 0.91-0.81 (m, 1H), 0.66 (s, 2H), 0.63 (s, 1H), 0.61-0.56 (m, 1H).

EXAMPLE 46

General Procedure for Saponification of Acetate Protective Group

In a 25 mL round bottom flask, 0.150 mmol of starting material were dissolved in 10 mL MeOH and 4 mL NaOH 1M, then refluxed overnight. The following morning, methanol was removed in vacuo and the remaining aqueous layer was extracted 3× with AcOEt. The combined organic layers were treated with brine, dried on anhydrous MgSO$_4$ and concentrated in vacuo. The crude product was used without further purification.

EXAMPLE 47

Synthesis of pregnan-3β-ol-20-(boc-aminoethyl)amine (39) of Formula 2.0

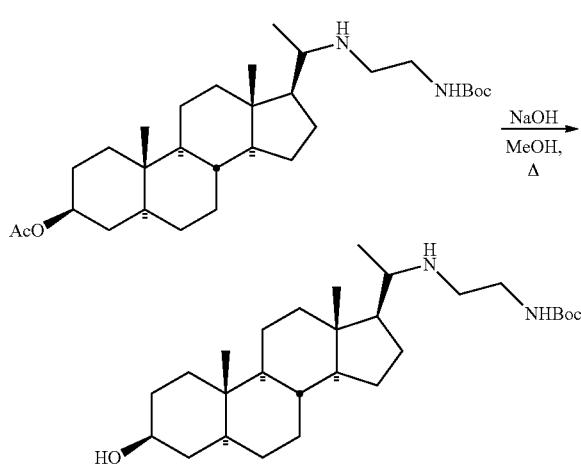

Following the procedure described in Example 46 above, 84 mg compound 36 (0.166 mmol) were used to yield 77 mg (100%) of desired compound 39.

$^1$H NMR (300 MHz, CDCl$_3$) δ (ppm) 5.08 ppm (d large, 1H), 3.57 (sept, 1H, J=5.0 Hz), 3.20 (sept, 2H, J=5.8 Hz), 2.79 (sext, 1H, J=5.8 Hz), 2.67-2.52 (m, 2H), 2.26-2.10 (m, 3H), 2.00-1.47 (m, 10H), 2.43 (s, 10H), 2.38-1.19 (m, 11H), 1.08 (quad, 3H, J=6.7 Hz), 1.05-1.00 (m, 2H), 0.98 (d, 3H, J=6.1 Hz), 0.94-0.81 (m, 2H), 0.79 (s, 3H), 0.67 (s, 2H), 0.64 (s, 1H0, 0.63-0.57 (m, 1H).

EXAMPLE 48

Synthesis of pregnan-3β-ol-20-(boc-aminopropyl)amine (40) of Formula 2.0

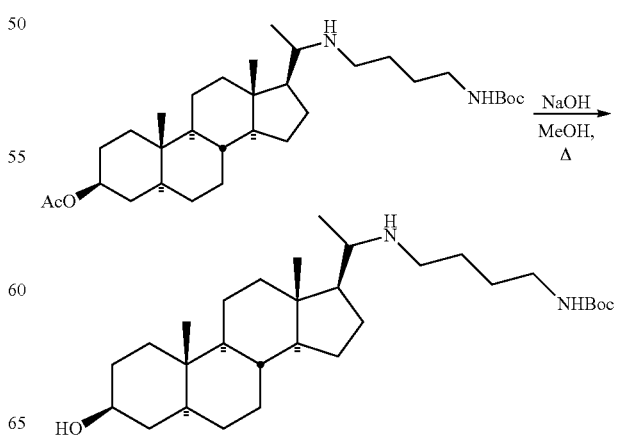

Following the procedure described in Example 46 above, 51 mg of compound 37 (0.099 mmol) were used to yield 40 mg (85%) of desired compound 40.

$^1$H NMR (300 MHz, CDCl$_3$) δ (ppm) 5.07 (s large, 1H), 3.57 (sept, 1H, 5.0 Hz), 3.17 (quad, 2H, J=5.9 Hz), 2.86-2.69 (m, 1H), 2.61-2.43 (m, 2H), 2.03-1.86 (m, 5H), 1.83-1.47 (m, 11H), 1.43 (s, 11H), 1.38-1.19 (m, 11H), 1.13-1.01 (m, 4H), 0.96 (d, 4H, J=6.3 Hz), 0.91-0.82 (m, 2H), 0.79 (s, 3H), 0.67 (s, 2H), 0.64 (s, 1H) 0.62 (dt, 1H, J$_1$=11.7 Hz, J$_2$=3.3 Hz).

EXAMPLE 49

Synthesis of pregnan-3β-ol-20-(boc-aminobutyl)amine (41) of Formula 2.0

Following the procedure described in Example 46 above, 70 mg of compound 38 (0.131 mmol) were used to yield 64 mg (98%) of desired compound 41.

$^1$H NMR (300 MHz, CDCl$_3$) δ (ppm) 4.98-4.82 (m, 1H), 3.57 (sept, 1H, J=4.9 Hz), 3.11 (quad, 2H, J=6.1 Hz), 2.75-2.65 (m, 1H0, 2.61-2.39 (m, 2H), 1.97-1.46 (m, 14H), 1.42 (s, 9H), 1.38-1.20 (M, 9H), 1.08 (d, 3H, J=6.1 Hz), 0.96 (d, 3H, J=6.1 Hz), 0.93-0.81 (m, 2H), 0.79 (s, 3H), 0.67 (s, 2H), 0.65 (s, 1H), 0.63-0.56 (m, 1H).

EXAMPLE 50

General Procedure for Boc Removal

In a 25 mL round bottom flask, the starting material was dissolved in 5 mL MeOH. A solution of anhydrous HCl (5 mL MeOH+75 µL AcCl) was added, and the reaction was allowed to stir for 1 h. The solvent was then removed in vacuo. The product was purified by trituration with ether or used as such.

EXAMPLE 51

Synthesis of pregnan-3β-ol-20-(aminoethyl)amine hydrochloride Salt (42) of Formula 2.0

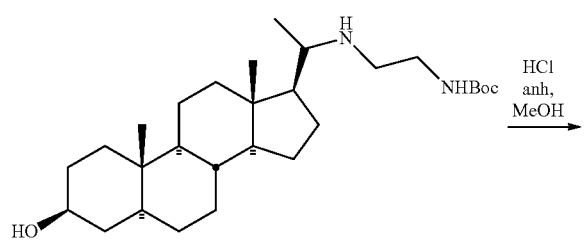

Following the procedure described in Example 50 above, 77 mg of compound 39 (0.166 mmol) were used to yield 64 mg (77%) of desired compound 42.

$^1$H NMR (300 MHz, CD$_3$OD) δ (ppm) 3.49 (sept, 1H, J=4.8 Hz), 3.41-3.31 (m, 3H), 3.30-3.24 (m, 1H), 3.11-3.01 (m, 1H), 2.05-1.83 (m, 2H), 1.82-1.61 (m, 6H), 1.58 (s, 3H), 1.43 (s, 3H), 1.40-1.29 (m, 4H), 1.30-1.21 (m, 6H), 1.17-1.06 (m, 3H), 1.03-0.86 (m, 2H), 0.82 (s, 3H), 0.76 (s, 1H), 0.73 (s, 2H), 0.69-0.61 (m, 1H).

EXAMPLE 52

Synthesis of pregnan-3β-ol-20-(aminopropyl)amine hydrochloride Salt (43) of Formula 2.0

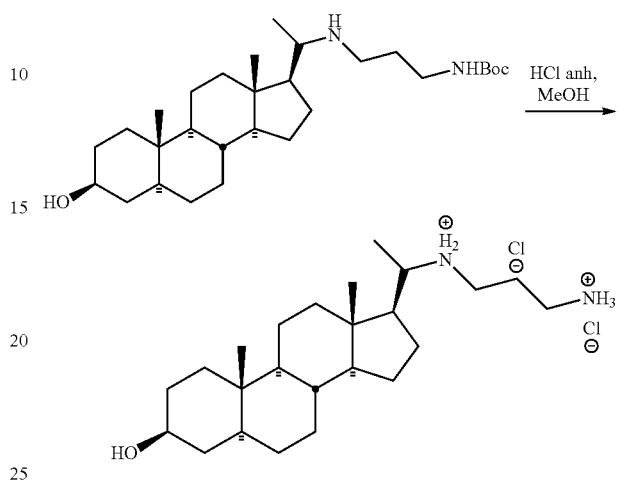

Following the procedure described in Example 50 above, 40 mg of compound 40 (0.084 mmol) were used to yield 23 mg (61%) of desired compound 43.

$^1$H NMR (300 MHz, CD$_3$OD) δ (ppm) 3.45-3.34 (m, 2H) 3.28 (quint, 2H, J=1.7 Hz), 3.13 (t, 2H, J=6.9 Hz), 3.05 (t, 2H, J=7.9 Hz) 2.09 (quint, 1H, J=7.2 Hz), 1.97-1.79 (m, 2H), 1.79-1.62 (m, 5H), 1.58 (s, 1H), 1.56-1.45 (m, 2H), 1.43 (s, 4H), 1.40-1.33 (m, 3H), 1.33-1.21 (m, 7H), 1.17-1.04 (m, 3H), 1.03-1.86 (m, 2H), 0.82 (s, 3H), 0.73 (s, 3H), 0.71-0.60 (m, 1H).

EXAMPLE 53

Synthesis of pregnan-3β-ol-20-(aminobutyl)amine hydrochloride Salt (44) of Formula 2.0

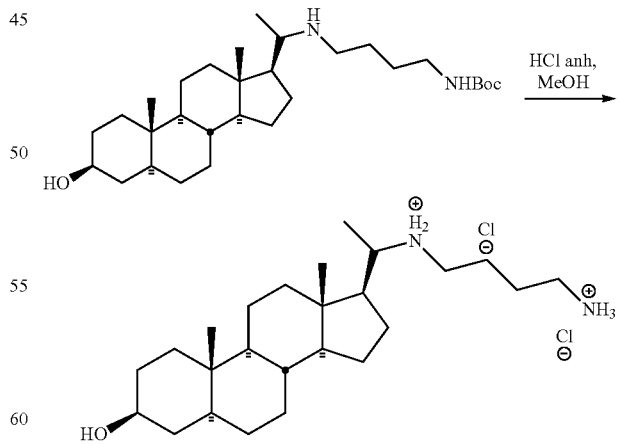

Following the procedure described in Example 50 above, 63 mg of compound 41 (0.128 mmol) were used to yield 50 mg (85%) of desired compound 44.

$^1$H NMR (300 MHz, CD$_3$OD) δ (ppm) 3.55-3.37 (m, 2H), 3.28 (m, 2H, J=1.5 Hz), 3.09-3.01 (s large, 2H), 3.01-2.92 (s large, 2H), 2.00-1.82 (m, 2H), 1.81-1.62 (m, 8H) 1.62-1.45 (m, 1H), 1.45-1.33 (m, 4H), 1.33-1.21 (m, 7H), 1.19-1.07 (m, 3H), 1.03-0.86 (m, 2H), 0.82 (s, 3H), 0.73 (s, 4H).

EXAMPLE 54

Synthesis of O-t-butyldimethylsilylpregnanolone (45) of Formula 2.0

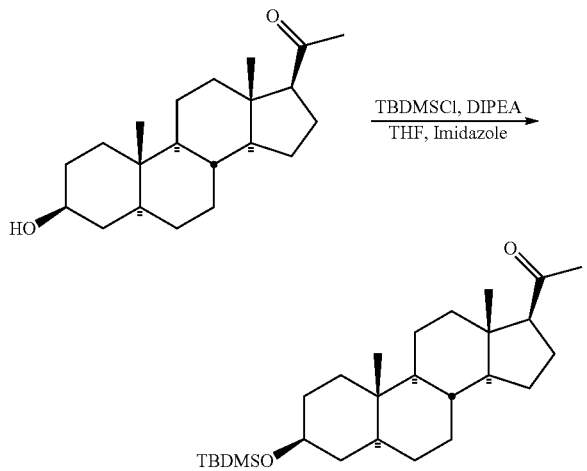

In a 250 mL round bottom flask, pregnanolone 28 (4.34 g, 13.6 mmol) was dissolved in 120 mL THF. Imidazole (2.3 g, 34 mmol, 2.5 eq), t-butyldimethylsilyl chloride (2.56 g, 17 mmol, 1.25 eq) and DIPEA (4.7 mL, 27.2 mmol, 2.0 eq) were successively added and the reaction was allowed to stir overnight at room temperature. The mixture was then concentrated under reduced pressure and diluted in AcOEt. The mixture was washed with water, 2×NaHCO₃ sat., 2× brine, dried over MgSO₄, and the solvents were removed in vacuo. The crude product was purified by flash chromatography (25% AcOEt/Hexanes) to yield 5.26 g (89%) of the desired compound 45.

¹H NMR (300 MHz, CDCl₃) δ (ppm) 3.54 (sept, 1H, J=5.8 Hz), 2.51 (t, 1H, J=9.4 Hz), 2.21-2.11 (m, 1H), 2.10 (s, 3H), 2.05-1.96 (m, 1H), 2.72-1.54 (m, 8H), 1.49-1.01 (m, 13H), 1.00-0.90 (m, 3H), 0.88 (s, 9H), 0.79 (s, 3H), 0.66 (dt, 3H, J₁=11.6 Hz, J₂=4.8 Hz), 0.59 (s, 3H), 0.05 (s, 6H).

EXAMPLE 55

Synthesis of t-Butyldimethysilylpregnane-3,20-diol (53) of Formula 2.0

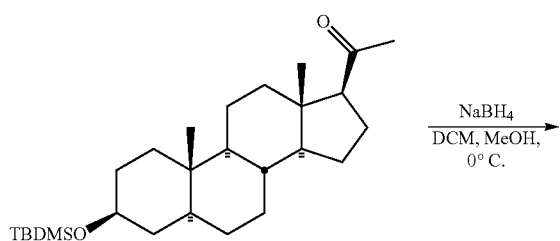

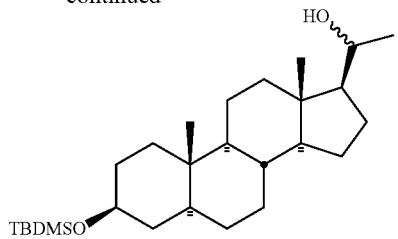

In a 25 mL round bottom flask, compound 45 (100 mg, 0.231 mmol) was dissolved in 5 mL DCM and 5 mL MeOH, then cooled at 0° C. NaBH₄ (9.6 mg, 0.254 mmol, 1.1 eq) was added and the reaction was stirred for 1 h at 0° C., monitored by TLC (50% AcOEt/Hexanes). Upon completion, the reaction was quenched with acetone for 30 minutes, then concentrated in vacuo. The resulting compound was suspended in water, and extracted 3× with AcOEt. The combined organic layers were washed with brine, dried on anhydrous MgSO₄ and concentrated in vacuo. The crude compound was purified by flash chromatography (10% AcOEt/Hexanes) to yield 66 mg (66%) of the desired compound 53.

¹H NMR (300 MHz, CDCl₃) δ (ppm) 3.78-3.66 (m, 1H), 3.54 (sept, 1H, J=5.8 Hz), 2.17 (s, 3H), 2.04-1.96 (m, 1H), 1.72-1.59 (m, 5H), 1.58-1.43 (m, 6H), 1.43-1.18 (m, 8H), 1.12 (d, 3H, J=5.8 Hz), 1.08-0.91 (m, 3H), 0.88 (s, 9H), 0.80 (s, 3H), 0.73 (s, 3H), 0.67-0.57 (m, 1H), 0.04 (s, 6H).

EXAMPLE 56

Synthesis of pregnane-3,20-diol (54) of Formula 2.0

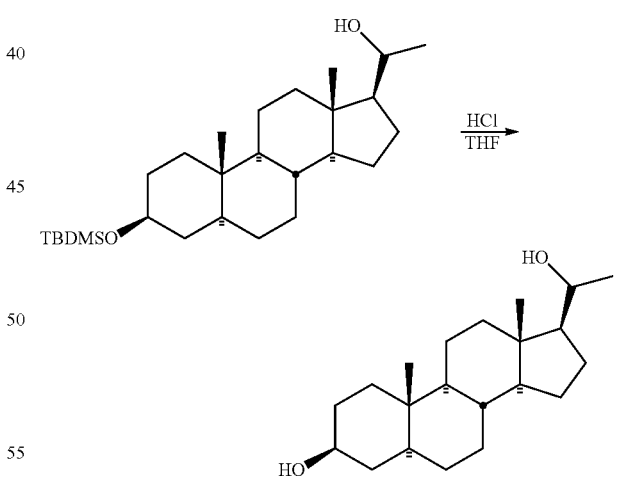

In a 5 mL round bottom flask, compound 53 (10 mg, 0.023 mmol) was dissolved in 2 mL THF and 0.5 mL HCl 1M. The reaction was stirred for 2 h, monitored by TLC. Upon completion, the reaction was concentrated in vacuo and AcOEt was added. The organic layer was washed successively with saturated aquous NaHCO₃, water and brine, then dried on anh. MgSO₄ and concentrated in vacuo. The crude material was purified by flash chromatography (50% AcOEt/Hexanes) to produce the desired compound 54 in a quantitative yield.

$^1$H NMR (300 MHz, CDCl$_3$) δ (ppm) 3.77-3.67 (m, 1H), 3.59 (sept, 1H, J=5.4 Hz), 1.85-1.45 (m, 14H), 1.44-1.18 (m, 14H), 1.13 (d, 5H, J=6.1 Hz), 1.06-0.83 (m, 5H), 0.81 (s, 3H) 0.74 (s, 3H), 0.70-0.59 (m, 1H).
$^{13}$C NMR (75.5 MHz, CDCl$_3$) δ (ppm) 71.4 (s), 70.6 (s), 58.6 (s), 55.9 (s), 54.3 (s), 44.9 (s), 42.5 (s), 40.1 (s), 38.2 (s), 37.0 (s), 35.5 (s), 35.4 (s), 32.1 (s), 31.5 (s), 28.7 (s), 25.6 (s), 24.5 (s), 23.6 (s), 21.1 (s), 12.6 (s), 12.3 (s). HRMS calculated for C$_{21}$H$_{36}$O$_2$: 320.2715. found: 320.2708.

EXAMPLE 57

Synthesis of Heterocyclic Analogues 15, 16 of Formula 3.0

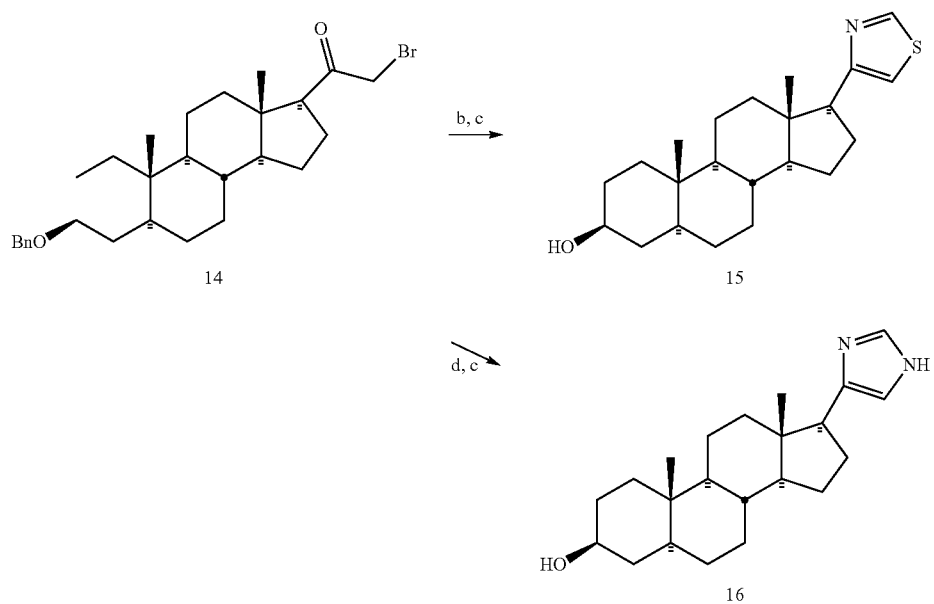

a. LDA, NBS, THF; b. thioformamide, dioxane, microwave;
c. H$_2$, Pd/C; d. HC(=NH)NH$_2$•AcOH, NH$_3$;

Thiazole analogue 15 is synthesized by initial bromination of exocyclic ketone 11 to generate intermediate bromoketone 14, treatment of bromoketone 14 with thioformamide followed by hydrogenolysis delivers analogue 15 (Ayesa et al., 2009). Treatment of bromoketone 14 with formamidine acetate followed by ammonia gives imidazole derivative 16 (Wong, 1995). Additional heterocyclic derivatives are obtained by the same approach (pyridines, substituted pyrimidines, thiazoles, imidazoles and pyridines).

EXAMPLE 58

Synthesis of Pregnanolone (28) of Formula 3.0

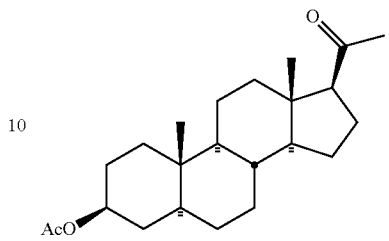

-continued

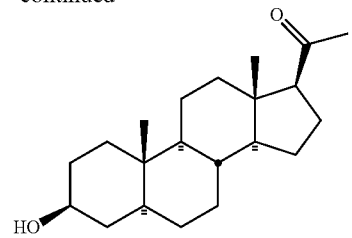

In a 500 mL round bottom flask, pregnanolone acetate (1.5 g, 4.18 mmol) was dissolved in 200 mL of MeOH, 70 mL EtOH, 80 mL H$_2$O 20 and 10 mL NaOH 1M. The mixture was refluxed for 4 hours. The organic solvents were then removed under reduced pressure as a solid suspension could be observed in the remaining aquous phase. The solid was isolated by filtration, rinsed with cold water and dried overnight at room temperature to yield 1.1 g (81%) of desired compound.

$^1$H NMR (300 MHz, CD$_3$OH) δ (ppm) 3.60 (m, 1H, J=4.5 Hz), 2.52 (t, 1H, J=8.8 Hz), 2.22-2.12 (m, 1H), 2.11 (s, 1H), 2.04-1.96 (m, 1H), 1.86-1.76 (m, 1H), 1.77-1.57 (m, 6H), 1.49-1.20 (m, 9H), 1.20-1.06 (m, 3H), 1.04-0.84 (m, 3H), 0.81 (s, 3H), 0.68 (dt, 1H, J$_1$=10.4 Hz, J$_2$=3.8 Hz), 0.60 (s, 3H).

$^{13}$C NMR (75.5 MHz, CDCl$_3$) δ (ppm) 209.7 (s), 71.2 (s), 63.8 (s), 56.7 (s), 54.2 (s), 44.8 (s), 44.3 (s), 39.1 (s), 38.2 (s), 37.0 (s), 35.5 (s), 32.0 (s), 31.4 (s), 31.0 (s), 28.6 (s), 24.4 (s), 22.8 (s), 21.3 (s), 13.5 (s), 12.3 (s). HRMS calculated for C$_{21}$H$_{34}$O$_2$: 318.2559. found: 318.2552.

EXAMPLE 59

Synthesis of O-t-butyldimethylsilyl-21-bromopregnanolone (46) of Formula 3.0

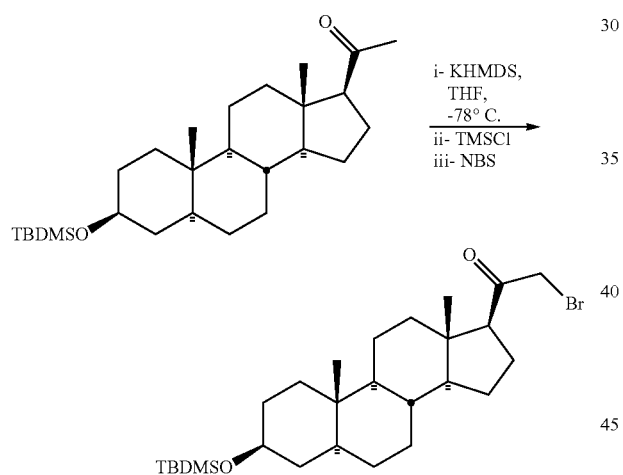

In a 50 mL round bottom flask under argon atmosphere, compound 45 (500 mg, 1.15 mmol) was cooled to −78° C. in anhydrous THF. KHMDS 1M in THF (1.27 ml, 1.27 mmol, 1.1 eq) was added and the mixture was stirred for 15 minutes. TMSCl (150 μL, 1.15 mmol, 1.0 eq) was added and the mixture was stirred for 1 h at room temperature, and monitored by TLC. (50% AcOEt/Hexanes). The reaction was cooled down to −78° C. before addition of N-Bromosuccinimide (204 mg, 1.15 mmol, 1.0 eq). After 1 hour of stirring at −78° C., the reaction was quenched with saturated aquous NaHCO$_3$ and THF was evaporated under reduced pressure. Water was added, and the solution was extracted with 3×AcOEt. The combined organic layers were washed with brine, dried on anhydrous MgSO$_4$ and concentrated in vacuo. The compound was purified by flash chromatography (2% AcOEt/Hexanes to 6% AcOEt/Hexanes) to yield 510 mg (87%) of desired compound 46.

$^1$H NMR (300 MHz, CDCl$_3$) δ (ppm) 3.87 (d, 2H, J=2.7 Hz), 3.51 (sept, 1H, J=5.3 Hz), 2.78 (t, 1H, J=8.9 Hz), 2.14 (quad, 1H, J=9.2 Hz), 1.87 (dt, 2H, J$_1$=11.7 Hz, J$_2$=2.7 Hz), 1.73-1.52 (m, 8H), 1.46-1.29 (m, 5H), 1.29-1.11 (m, 6H), 1.08-0.88 (m, 2H), 0.85 (s, 10H), 0.76 (s, 3H), 0.63 (dt, 1H, J$_1$=12.1 Hz, J$_2$=2.9 Hz), 0.59 (s, 3H), 0.01 (s, 6H).

EXAMPLE 60

General Procedure for Substitution of Bromine by Amino Compounds

In a 20 mL vial, compound 46 was solubilised in THF (≈0.1M). 2.0 eq of corresponding amine was added, and the reaction was stirred for 1 h at room temperature. THF was removed in vacuo. The obtained solid was suspended into water, and extracted 3× with AcOEt. The organic combined layers were washed with brine, dried on anhydrous MgSO$_4$ and the solvent was removed in vacuo. Crude compound was purified by flash chromatography.

Compound was then solubilised in THF:HCl (4:1 solution) and stirred for 2 h. Upon completion (TLC), saturated aq. NaHCO$_3$ was added until the solution is alkaline and THF was removed in vacuo. The remaining aquous layer was extracted 3× with AcOEt, and the combined organic layers were washed with brine, dried on anhydrous MgSO$_4$ and concentrated under reduced pressure. The crude compound was purified by flash chromatography.

EXAMPLE 61

General Procedure for Substitution of Bromine by Amino Compounds

In a 5 mL vial, compound 46 was solubilised in THF (0.09M) and 2-5 eq of corresponding amine was added. The reaction was stirred overnight, monitored by TLC for completion. The reaction was then acidified with HCl 1M, and allowed to stir upon completion, monitored by TLC. THF was removed in vacuo and the remaining water was removed via lyophilization. The crude product was purified via reverse-phase preparative chromatography.

EXAMPLE 62

Synthesis of N,N-dimethyl-21-aminopregnanolone (47) of Formula 3.0

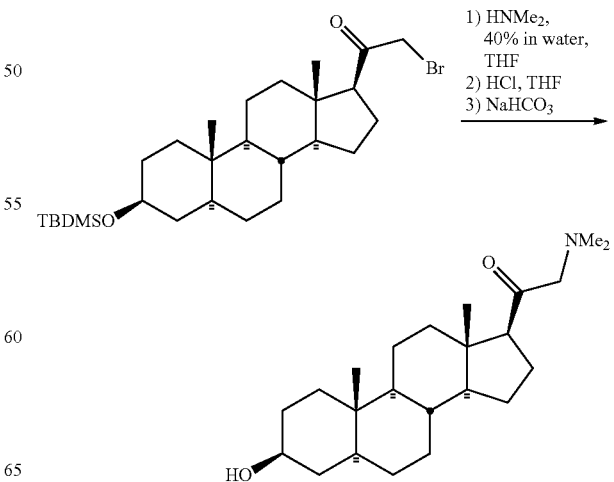

Following the procedure described in Example 60 above, 125 mg of compound 46 (0.244 mmol) were used to obtain 68 mg of silylated intermediate. Upon deprotection, 20 mg (38% overall yield) of compound 47 were obtained.

$^1$H NMR (300 MHz, CDCl$_3$) δ (ppm) 3.58 (sept, 1H, J=5.2 Hz), 3.13 (dd, 2H, J$_1$=21.4 Hz, J$_2$=21.7 Hz), 2.55 (t, 1H, J=8.8 Hz), 2.28 (s, 6H), 2.16 (d, 1H, J=9.3 Hz), 1.91-175 (m, 4H), 1.74-1.52 (m, 6H), 1.43-1.20 (m, 8H), 1.20-1.04 (m, 3H), 1.03-0.83 (m, 3H), 0.79 (s, 1H), 0.72-0.61 (m, 1H), 0.60 (s, 3H).

$^{13}$C NMR (75.5 MHz, CD$_3$OD) δ (ppm) 206.5 (s), 70.3 (s), 60.3 (s), 56.6 (s), 55.9 (s), 55.7 (s), 54.4 (s), 54.1 (s), 44.7 (s), 44.4 (s), 43.8 (s), 43.5 (s), 38.7 (s), 38.2 (s), 37.5 (s), 36.8 (s), 35.6 (s), 35.4 (s), 35.2 (s), 31.8 (s), 30.6 (s), 29.5 (s), 24.1 (s), 23.4 (s), 22.4 (s), 20.9 (s), 20.8 (s), 11.3 (s). HRMS calculated for C$_{23}$H$_{39}$O$_2$N: 362.3059. found: 362.3059.

EXAMPLE 63

Synthesis of 21-piperidinopregnanolone (48) of Formula 3.0

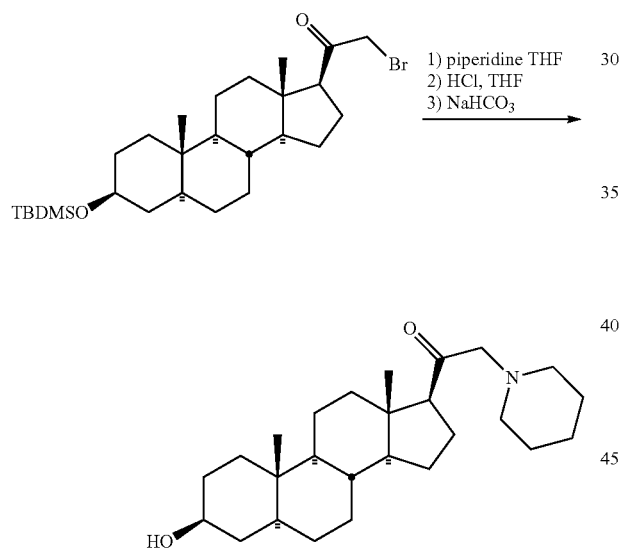

Following the procedure described in Example 60 above, 100 mg of compound 46 (0.195 mmol) were used to obtain 80 mg of silylated intermediate. Upon deprotection, 46 mg (74% overall yield) of compound 48 were obtained.

$^1$H NMR (300 MHz, CDCl$_3$) δ (ppm) 3.56 (sept, 1H, J=4.8 Hz), 3.08 (s, 2H), 2.58 (t, 1H, J=9.8 Hz), 2.37 (s large, 4H), 2.13 (d, 1H, J=10.3 Hz), 1.86 (dt, 2H, J$_1$=11.1 Hz, J$_2$=3.9 Hz), 1.78 (d, 1H, J=11.1 Hz), 1.72-1.48 (m, 10H), 1.45-1.19 (m, 10H), 1.18-1.03 (m, 3H), 1.01-0.83 (m, 3H), 0.77 (s, 3H), 0.70-0.62 (m, 1H), 0.58 (s, 3H).

$^{13}$C NMR (75.5 MHz, CD$_3$OD) δ (ppm) 213.5 (s), 71.3 (s), 60.2 (s), 58.8 (s), 56.8 (s), 54.7 (s), 54.2 (s), 44.8 (s), 39.0 (s), 38.1 (s), 37.0 (s), 35.5 (s), 34.5 (s), 32.0 (s), 31.5 (s), 28.6 (s), 25.6 (s), 24.5 (s), 23.9 (s), 23.0 (s), 21.3 (s), 13.6 (s), 12.4 (s). HRMS calculated for C$_{26}$H$_{43}$O$_2$N, 402.3372. found: 402.3380.

EXAMPLE 64

Synthesis of N-methyl-21-aminopregnanolone hydrochloride salt (49) of Formula 3.0

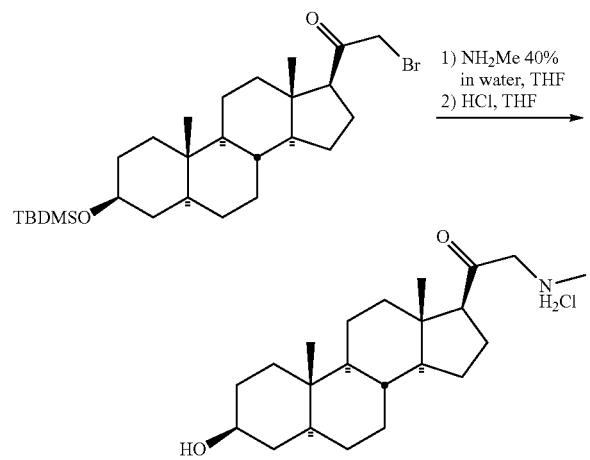

Following the procedure described in Example 61 above, 150 mg of compound 46 (0.293 mmol) were used to obtain 108 mg (96%) of crude compound. 50 mg were purified by reverse-phase preparative chromatography to yield 32 mg of pure compound 49.

$^1$H NMR (300 MHz, CDCl$_3$) δ (ppm) 3.49 (sept, 1H, J=5.1 Hz), 2.68 (s, 2H), 2.67 (t, 1H, J=9.2 Hz), 2.52 (s, 3H), 2.18-2.07 (m, 1H), 2.00-1.92 (m, 1H), 1.80-1.58 (m, 6H), 1.54-1.46 (m, 1H), 1.45-1.32 (m, 5H), 1.17-1.07 (m, 2H), 1.05-1.90 (m, 3H), 0.82 (s, 3H), 0.76-0.57 (m, 1H), 0.65 (s, 3H).

$^{13}$C NMR (75.5 MHz, CD$_3$OD) δ (ppm) 203.1 (s), 70.4 (s), 60.2 (s), 57.2 (s), 56.4 (s), 54.1 (s), 44.7 (s), 38.2 (s), 37.4 (s), 36.8 (s), 35.4 (s), 35.2 (s), 31.9 (s), 30.6 (s), 28.4 (s), 24.0 (s), 22.3 (s), 20.9 (s), 12.5 (s), 11.2 (s).

EXAMPLE 65

Synthesis of 21-piperazinopregnanolone hydrochloride Salt (50) of Formula 3.0

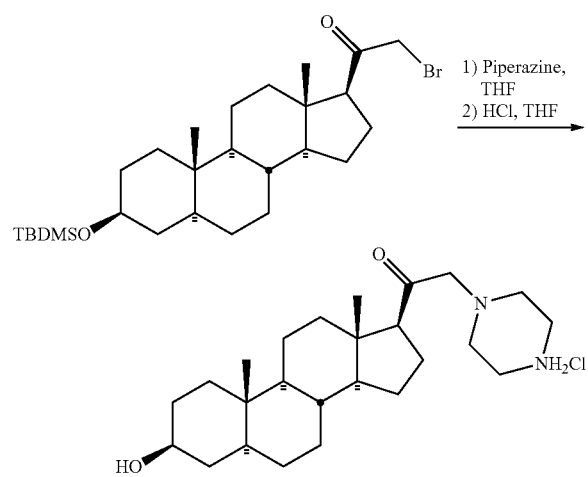

Following the procedure described in Example 61 above, 200 mg of compound 46 (0.391 mmol) were used to obtain 172 mg (100%) of the desired compound 50.

$^1$H NMR (300 MHz, CDCl$_3$) δ (ppm) 3.36 (m, 1H), 2.63 (t, 1H, J=6.9 Hz), 2.21-2.09 (m, 1H), 2.06-1.98 (m, 1H), 1.81-1.58 (m, 6H), 1.55-1.46 (m, 2H), 1.45-1.33 (m, 3H), 1.33-1.18 (m, 6H), 1.17-1.06 (m, 2H), 1.05-0.89 (m, 3H), 0.82 (s, 3H), 0.72 (dt, 1H, J$_1$=12.0 Hz, J$_2$=2.8 Hz), 0.67 (s, 3H).

$^{13}$C NMR (75.5 MHz, CD$_3$OD) δ (ppm) 202.6 (s), 70.4 (s), 64.2 (s), 60.5 (s), 56.5 (s), 54.1 (s), 44.9 (s), 44.7 (s), 40.5 (s), 40.2 (s), 38.2 (s), 37.4 (s), 36.8 (s), 35.4 (s), 35.2 (s), 31.8 (s), 30.7 (s), 28.4 (s), 24.0 (s), 22.4 (s), 20.9 (s), 12.5 (s), 11.3 (s).

EXAMPLE 66

Synthesis of Aminothiazole (51) of Formula 3.0

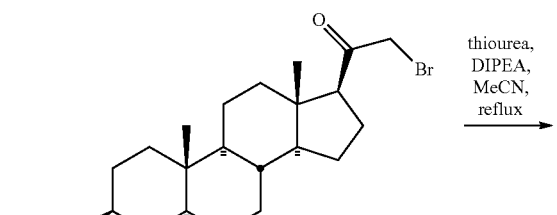

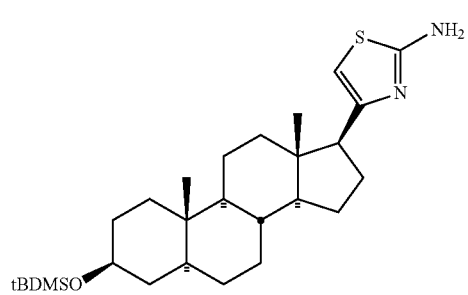

In a 50 mL round bottom flask, compound 46 (47 mg, 0.091 mmol) was dissolved in 7 mL acetonitrile. Thiourea (8 mg, 0.105 mmol, 1.15 eq) and DIPEA (31 μL, 0.178 mmol, 1.95 eq) were added and the reaction was brought to reflux for 5 h, monitored by TLC (50% AcOEt/Hexanes). Upon cooling to room temperature, solvents were removed in vacuo. The crude product was purified by flash chromatography (25% AcOEt/Hexanes) to yield 21 mg (44%) of the desired compound 51.

$^1$H NMR (300 MHz, CDCl$_3$) δ (ppm) 6.09 (s, 1H), 5.03 (s large, 2H), 3.55 (sept, 1H, J=5.3 Hz), 2.58 (t, 1H, J=9.7 Hz), 1.98-1.86 (m, 3H), 1.75-1.62 (m, 4H), 1.58-1.33 (m, 4H), 1.32-1.18 (m, 7H), 1.17-1.04 (m, 2H), 1.00-0.91 (m, 1H), 0.88 (s, 9H), 0.79 (s, 3H), 0.66 (dt, 1H, J$_1$=11.0 Hz, J$_2$=3.5 Hz), 0.49 (s, 3H), 0.10 (s, 1H), 0.04 (s, 5H).

EXAMPLE 67

Deprotection of 51 to Form Compound (52) of Formula 3.0

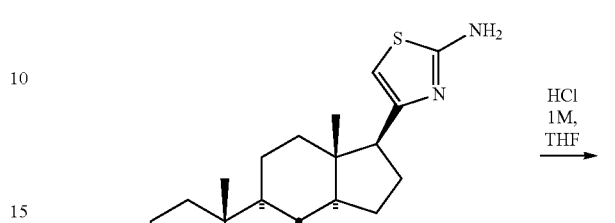

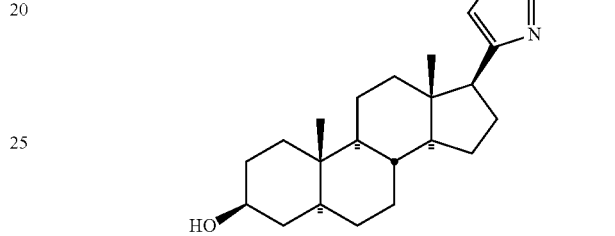

In a 10 mL round bottom flask, 5 mg compound 51 (10 mmol) was dissolved in 4 mL THF and 1 mL HCl 1M. The reaction was stirred at room temperature until completion (2 h, monitored by TLC). Solvent was removed in vacuo, and the remaining aqueous phase was removed by 2 co-evaporations with THF. The crude compound was triturated with diethyl ether to yield 4 mg of desired compound 52 (hydrochloric salt) (100% yield).

$^1$H NMR (300 MHz, CD$_3$OD) δ (ppm) 6.52 (s, 1H), 3.49 (sext, 1H, J=5.8 Hz), 2.61 (t, 1H, J=2.64 Hz), 2.07-1.86 (m, 2H), 1.81-1.79 (m, 5H), 1.56-1.08 (m, 11H), 1.05-0.91 (m, 2H), 0.82 (s, 3H), 0.72 (dt, 1H, J$_1$=11.0 Hz, J$_2$=4.2 Hz), 0.59 (s, 3H).

$^{13}$C NMR (75.5 MHz, CD$_3$OD) δ (ppm) 167.5 (s), 142-6 (s), 101.7 (s), 70.3 (s), 55.5 (s), 54.4 (s), 50.0 (s), 44.8 (s), 44.0 (s), 37.5 (s), 37.4 (s), 36.8 (s), 35.9 (s), 35.3 (s), 31.8 (s), 30.7 (s), 28.4 (s), 25.4 (s), 23.7 (s), 20.7 (s), 12.3 (s), 11.3 (s). HRMS calculated for C$_{22}$H$_{35}$ON$_2$S: 374.2392. found: 374.2388.

EXAMPLE 68

Synthesis of Compound 26 of Formula 5.0

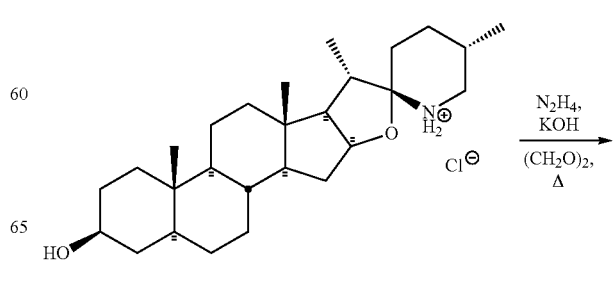

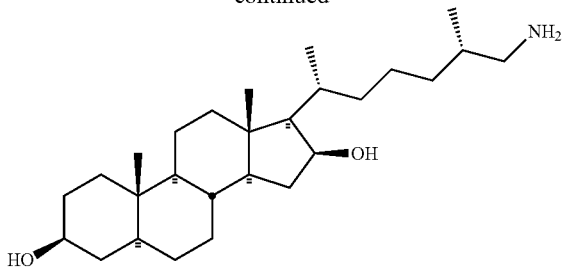

In a 5 mL round bottom flask, tomatidine hydrochloride salt (10 mg, 0.022 mmol), hydrazine (10.5 ◻ L, 0.332 mmol, 15 eq.) and KOH (18 mg, 0.320 mmol, 14.5 eq) in 2.5 mL ethylene glycol were heated to 100° C. for 1 h, then to 200° C. for 4 h. The reaction was monitored by TLC until completion, then allowed to cool to room temperature. The resulting mixture was diluted with water, then extracted 5× with diethyl ether. The organic fractions were combined, washed with brine, dried on anhydrous $MgSO_4$ and solvent was removed under reduced pressure. The crude product was purified by flash chromatography (25% AcOEt/Hexanes) to yield 5 mg (54%) of the desired compound 26.

EXAMPLE 69

Potentiating Effect of Steroid Alkaloids on Aminoglycoside Antibiotics Against Normal *S. aureus* Strains and Antimicrobial Effect of Steroid Alkaloids Against SCV *S. aureus* Bacteria Compounds of the present invention potentiate aminoglycosides' effect on normal *S. aureus* strains and are antibacterial against *S. aureus* SCVs.

Compounds of the invention were tested for their ability to potentiate the aminoglycoside antibiotic gentamicin against *S. aureus* ATCC 29213 and for their antibacterial activity against ATCC 29213 and the SCV strain NewbouldΔhemB. MICs were determined as described in the Example 10 above.

Results:

Table 11 below shows that compounds of the present invention have the ability to potentiate gentamicin against normal *S. aureus* and to inhibit the growth of SCV strain NewbouldΔhemB. Compounds were divided in categories according to their potentiating activity level with gentamicin (no or mild potentiation (1-2 fold increase in gentamicin activity) vs. moderate or strong potentiation (4-16 fold increase in gentamicin activity)) and antibacterial activity level against SCVs (low, MIC> about 8 μg/ml; moderate, MIC=about 4 to about 8 μg/ml; and strong activity, MIC about 0.5 μg/ml).

TABLE 11

Antibacterial efficacy (MIC, Minimal Inhibitory Concentration) of compounds (Cpd) of the invention as determined by 1) the susceptibility (MIC in μg/ml) of *S. aureus* ATCC 29213 to the aminoglycoside antibiotic gentamicin (GEN) in the presence of 8 μg/ml of the Cpd and/or 2) their antibacterial activity against *S. aureus* SCVs.

| Compound (Cpd) | MIC of Cpd against ATCC29213 (μg/ml) | Fold[a] (MIC of GEN alone/MIC of GEN with Cpd) | MIC of Cpd against SCV hemB[b] (μg/ml) |
|---|---|---|---|
| Tomatidine hydrochloride salt | >16 | 4-16 | ≤0.5 |
| Tomatidine mesylate (57) | >16 | 4-16 | ≤0.5 |
| Tomatidine citrate (58) | >16 | 4-16 | ≤0.5 |
| Solasodan | >16 | 1-2 | >8 |
| N-formyl tomatidine (21) | >16 | 1-2 | >8 |
| 3-alpha-hydroxytomatidine hydrochloride salt (23) | >16 | 4-16 | 4-8 |
| 3-oxotomatidine hydrochloride salt (25) | >16 | 4-16 | ≤0.5 |
| Compound 26 | >16 | 4-16 | ≤0.5 |
| Pregnanolone (28) | >16 | 1-2 | >8 |
| pregnan-3β-ol-20-amine Diasterioisomer (30a) | >16 | 1-2 | >8 |
| pregnan-3β-ol-20-amine Diasterioisomer (30b) | >16 | 1-2 | >8 |
| Pregnan-3β-ol-20-((N,N-dimethylamino)propyl)amine (32) | >16 | 4-16 | >8 |
| Pregnan-3β-ol-20-(aminoethyl)amine hydrochloride salt (42) | >16 | 1-2 | 4-8 |
| Pregnan-3β-ol-20-(aminopropyl)amine hydrochloride salt (43) | >16 | 1-2 | 4-8 |
| Pregnan-3β-ol-20-(aminobutyl)amine hydrochloride salt (44) | >16 | 1-2 | >8 |
| N,N-dimehyl-21-aminopregnanolone (47) | >16 | 1-2 | >8 |
| 21-piperidinopregnanolone (48) | >16 | 1-2 | >8 |
| N-methyl-21-aminopregnanolone hydrochloride salt (49) | >16 | 1-2 | >8 |
| 21-piperazinopregnanolone hydrochloride salt (50) | >16 | 1-2 | >8 |

TABLE 11-continued

Antibacterial efficacy (MIC, Minimal Inhibitory Concentration) of
compounds (Cpd) of the invention as determined by 1) the susceptibility
(MIC in µg/ml) of *S. aureus* ATCC 29213 to the aminoglycoside antibiotic
gentamicin (GEN) in the presence of 8 µg/ml of the Cpd and/or 2) their
antibacterial activity against *S. aureus* SCVs.

| Compound (Cpd) | MIC of Cpd against ATCC29213 (µg/ml) | Fold[a] (MIC of GEN alone/MIC of GEN with Cpd) | MIC of Cpd against SCV hemB[b] (µg/ml) |
|---|---|---|---|
| Compound 52 | >16 | 1-2 | >8 |
| pregnane-3,20-diol (54) | >16 | 1-2 | >8 |
| O-allyltomatidine hydrochloride salt (56) | 8-16 | 4-16 | ≤0.5 |

[a]The fold is the ratio of the MIC of gentamicin (GEN) alone against *S. aureus* ATCC 29213 (MIC of 0.5-1 µg/ml) over the MIC of gentamicin obtained in the presence of 8 µg/ml of compound (Cpd). The exception was Compound 56 that was used at 4 µg/ml. Results are provided in categories of synergy (no or mild synergy, 1-2 synergy fold; moderate or strong synergy, 4-16 synergy fold).
[b]Results are provided in categories of inhibitory activities against *S. aureus* SCV (strong activity, MIC ≤ 0.5 µg/ml; moderate activity, MIC = 4-8 µg/ml; low activity, MIC > 8 µg/ml).

EXAMPLE 70

Antibacterial Activity of Compounds of the Present Invention on *Bacillus* spp., and on *Listeria* spp.

Susceptibility of the *Bacillus* spp., and of the *Listeria* spp. to steroid alkaloids was determined as follows.

Method:

The effect of tomatidine on the growth of *Bacillus subtilis* strains ATCC 6633 and ATCC 9372, *Bacillus cereus* strain ATCC 11778 and *Listeria monocytogenes* strain ATCC 13932 was tested by an agar diffusion method. *Bacillus* spp. strains and *Listeria monocytogenes* were spread on the surface of Mueller-Hinton agar and Mueller-Hinton supplemented with 5% sheep blood, respectively. 35 µg of tomatidine diluted in DMSO or DMSO alone were added to wells for diffusion and plates were incubated for 24 hours at 35° C. The diameters of the zones of inhibition around the wells (for the DMSO control and for the tomatidine well) were measured and reported in mm in TABLE 12 below.

TABLE 12

Tomatidine biological activity against *Bacillus* and *Listeria* spp.

| | | Diameter of inhibition zone (mm) | |
|---|---|---|---|
| Species | Strains | DMSO | Tomatidine (35 µg) |
| *Bacillus subtilis* | ATCC 9372 | 0 | 25.5 |
| *Bacillus subtilis* | ATCC 6633 | 5 | 25.5 |
| *Bacillus cereus* | ATCC 11778 | 0 | 21.5 |
| *Listeria monocytogenes* | ATCC 13932 | 0 | 12.5 |

Together with results presented in Examples 1, 2, 8 and 10, results from TABLE 12 show that compounds of the present invention have biological activities against bacteria within the Firmicutes phylum.

EXAMPLE 71

Methods for Assessing Biological Activities of Compounds of the Invention

The biological activity of compounds of the present invention can be determined using techniques as described in Examples 1 (i.e., antibacterial activity against *S. aureus* SCVs), 2 (i.e., antibacterial activity against anaerobic bacterium (e.g., *C. perfringens*)), 8 (i.e., antibacterial activity against normal *S. aureus* in co-culture with *P. aeruginosa*), 10 (i.e., potentiating effect on aminoglycoside antibiotics against normal *S. aureus, S. epidermidis, S. haemolyticus, S. saprophyticus,* and *S. hominis*) and 70 (i.e., antibacterial activity against *Bacillus* spp. and *Listeria* spp.) above.

Also determined is the antibacterial activity against the streptococci of group A, of group B, of the viridans group, of the mitis group, whereas the strains and species are of human or animal origins, such as *S. pneumoniae, S. pyogenes, S. mitis, S. agalactiae, S. dysgalactiae, S. uberis, S. suis, S. bovis* and *S. intermedius*. Additional coagulase-positive and -negative *staphylococci* are tested including *S. intermedius, S. hyicus, S. chromogenes, S. stimulans, S. lugdenensis S. capitis*.

Additional anaerobes are tested including the *C. difficile*, the *Peptostreptococcus, Peptococcus* following the method described in Example 2 above. Cultivation techniques for aerobes, anaerobes and fastidious bacteria are as recommended by the Clinical and Laboratory Standard Institute (CLSI, 2006).

Susceptibility of other bacterial genus such as *Corynebacterium* and *Gardnerella* is also tested.

EXAMPLE 72

Inhibitory Effect of Compounds of the Present Invention Measured in Cell Cultures The compounds of the present invention are tested for their ability to inhibit the growth of microbial pathogens with electron transport deficiencies (or with normal electron transport when used in combination with aminoglycosides) during infection of cell cultures such as those used in Example 7.

EXAMPLE 73

Inhibitory Effect of Compounds of the Present Invention Measured During Infection in Animals (In Vivo)

The compounds of the present invention are able to inhibit the growth of microbial pathogens with electron transport deficiencies (or with normal electron transport when used in combination with aminoglycosides) during infection of an animal (in vivo). The antibacterial activity in vivo is demonstrated through the use of various infection models using, for example mice models of septicemia, soft tissue infections, pneumonia and mastitis.

Septicemia Model

The septicemia model (Deslouches et al, 2005) allows testing the efficacy of compounds to clear or diminish an infection. Bacteria are injected iv or ip with an inoculum that leads to 50-70% mortality in untreated mice (3-5 mice per test group). Following inoculation, compounds are administered either iv, ip, sc or im and treatment efficacy is measured by the reduction of bacterial CFU in various organs (e.g., liver, kidneys), in the peritoneal liquid or in blood or is evaluated based on the animals' survival rate.

Neutropenic Mouse Thigh Model

Compound efficacy in a neutropenic mouse thigh model is evaluated as follows (Malouin et al, 2005): Mice (immune suppressed with cyclophosphamide treatments prior to infection) are challenged with bacteria ($10^4$ CFU per thigh im). To determine efficacy, compounds are delivered iv, sc, ip or im 2 h post-infection. Mice (3-5 mice per treatment) are euthanized 8 h post-infection. The thigh tissues (two samples per animal) are recovered, homogenized, and bacterial CFU per g of tissue are determined by plating appropriate dilutions.

Lung Infection (Pneumonia) Model

Compound efficacy in a lung infection (pneumonia) model is evaluated as follow (Ragle et al, 2010): Mice are challenged with intra-tracheal injection of bacteria ($10^8$ CFU). To determine efficacy, compounds are delivered iv, sc, ip, im or by aerosol, 2 h post-infection. Mice (3-5 mice per treatment) are euthanized 24 h post-infection. The lungs are recovered, homogenized, and bacterial CFU per g of tissue are determined by plating appropriate dilutions.

Mouse Mastitis Model

Compound efficacy in a mouse mastitis model is evaluated as follow (Brouillette et al, 2004b): Lactating CD-1 mice are challenged with bacteria injected through the teat canal. A Hamilton syringe with a blunt needle is used to inoculate with $10^2$ CFU per gland in both L4 and R4 mammary glands. Compounds are delivered by an intra-mammary injection 4 h following challenge. Each experimental group is composed of 3-6 mice (i.e., 6-12 glands). Mammary glands are harvested, weighed and homogenized in PBS at 18 h. Homogenates are serially diluted and plated on agar for bacterial CFU determination.

Although the present invention has been described hereinabove by way of specific embodiments thereof, it can be modified, without departing from the spirit and nature of the subject invention as defined in the appended claims.

REFERENCES

Alexander, E. H., and Hudson, M. C. (2001) Factors influencing the internalization of *Staphylococcus aureus* and impacts on the course of infections in humans. *Appl Microbiol Biotechnol* 56: 361-366.

Allegrucci, M., and Sauer, K. (2008) Formation of *Streptococcus pneumoniae* non-phase-variable colony variants is due to increased mutation frequency present under biofilm growth conditions. *J Bacteriol* 190: 6330-6339.

Archer, G. L. (1998) *Staphylococcus aureus*: a well-armed pathogen. *Clin Infect Dis* 26: 1179-1181.

Atalla, H., Gyles, C., Jacob, C. L., Moisan, H., Malouin, F., and Mallard, B. (2008) Characterization of a *Staphylococcus aureus* small colony variant (SCV) associated with persistent bovine mastitis. *Foodborne Pathog Dis* 5: 785-799.

Ayesa, S.; Lindquist, C.; Agback, T.; Benkestock, K.; Classon, B.; Henderson, I.; Hewitt, E.; Jansson, K.; Kallin, A.; Sheppard, D.; Samuelsson, B. Solid-phase parallel synthesis and SAR of 4-amidofuran-3-one inhibitors of cathepsin S: effect of sulfonamides P3 substituents on potency and selectivity. *Bioorg Med Chem* 2009, 17, 1307-24.

Bad Bug Book. *Bacillus cereus* and other *Bacillus* spp. Foodborne Pathogenic Microorganisms and Natural Toxins Handbook. Food and Drug Administration (www.fda.gov)

Bednarek, P., and Osbourn, A. (2009) Plant-microbe interactions: chemical diversity in plant defense. *Science* 324: 746-748.

Beierlein J M, Anderson A C. 2011. New developments in vaccines, inhibitors of anthrax toxins, and antibiotic therapeutics for *Bacillus anthracis*. Curr Med. Chem. 18(33): 5083-94.

Black, J. G. (2008) *Microbiology: Principles and Explorations* 7th ed. John Wiley & Sons.

Bolger, M. B.; Wieland, S.; Hawkinson, J. E.; Xia, H.; Upasani, R.; Lan, N. C. In vitro and in vivo activity of 16,17-dehydro-epipregnanolones: 17,20-bond torsional energy analysis and D-ring conformation. *Pharm Res* 1996, 13, 1488-94. Bouarab, K., El ordi, M., Gattuso, M., Moisan, H. and Malouin, F. (2007) Plant stress response agents affect *Staphylococcus aureus* virulence genes. Abstr. 47th Intersci. Conf. *Antimicrob. Agents Chemother.*, abstr. C1-1483.

Brouillette, E., Martinez, A., Boyll, B. J., Allen, N. E., and Malouin, F. (2004) Persistence of a *Staphylococcus aureus* small-colony variant under antibiotic pressure in vivo. *FEMS Immunol Med Microbiol* 41: 35-41.

Brouillette, E., G. Grondin, C. Lefebvre, B. G. Talbot, and F. Malouin. 2004b. Mouse mastitis model of infection for antimicrobial compound efficacy studies against intracellular and extracellular forms of *Staphylococcus aureus*. Vet. Microbiol. 101:253-262.

Bryan, L. E., and Kwan, S. (1981) Mechanisms of aminoglycoside resistance of anaerobic bacteria and facultative bacteria grown anaerobically. *J Antimicrob Chemother* 8 Suppl D: 1-8.

Canadian Cystic Fibrosis Foundation (2007) Patient data registry report. Toronto, ON, Canada.

Casey, A. L., Lambert, P. A., and Elliott, T. S. (2007) Staphylococci. *Int J Antimicrob Agents* 29 Suppl 3: S23-32

Chambers, H. F., and Deleo, F. R. (2009) Waves of resistance: *Staphylococcus aureus* in the antibiotic era. *Nat Rev Microbiol* 7: 629-641.

Chastre, J., and Fagon, J. Y. (2002) Ventilator-associated pneumonia. *Am J Respir Crit. Care Med* 165: 867-903.

Chatterjee, I., Herrmann, M., Proctor, R. A., Peters, G., and Kahl, B. C. (2007) Enhanced post-stationary-phase survival of a clinical thymidine-dependent small-colony variant of *Staphylococcus aureus* results from lack of a functional tricarboxylic acid cycle. *J Bacteriol* 189: 2936-2940.

Clinical and Laboratory Standards Institute (CLSI) (2006) Methods for dilution antimicrobial susceptibility tests for bacteria: Approved Standard.

Cystic Fibrosis Foundation (2008) Patient registry annual report. Washington, D.C.

Dasenbrook, E. C., Checkley, W., Merlo, C. A., Konstan, M. W., Lechtzin, N., and Boyle, M. P. (2010) Association between respiratory tract methicillin-resistant *Staphylococcus aureus* and survival in cystic fibrosis. Jama 303: 2386-2392.

Deslouches, B., K. Islam, J. K. Craigo, S. M. Paranjape, R. C. Montelaro, and T. A. Mietzner. 2005. Activity of the De Novo Engineered Antimicrobial Peptide WLBU2 against *Pseudomonas aeruginosa* in Human Serum and Whole Blood: Implications for Systemic Applications. *Antimicrob. Agents chemother.* 49: 3208-3216

Eliopoulos, G. M., and R. C. Moellering. 1996. Antimicrobial combinations. In Antibiotics in Laboratory Medicine, 4th ed. (V. Lorian, Ed.), pp 330-396. Williams and Wilkins, Baltimore, Md.

Friedman, M. (2002) Tomato glycoalkaloids: role in the plant and in the diet. J Agric Food Chem 50: 5751-5780.

Galli, J., Ardito, F., Calo, L., Mancinelli, L., Imperiali, M., Parrilla, C., Picciotti, P. M., and Fadda, G. (2007) Recurrent upper airway infections and bacterial biofilms. *J Laryngol Otol* 121: 341-344.

Gibson, R. L., Burns, J. L., and Ramsey, B. W. (2003) Pathophysiology and management of pulmonary infections in cystic fibrosis. *Am J Respir Crit. Care Med* 168: 918-951.

Ginnes, R. B., and V. Stewart. 1996. Respiration. In *Escherichia coli* and *Salmonella*, cellular and molecular biology, p. 217-261. Ed. F. C. Neidhardt. American Society for Microbiology, Washington.

Goerke, C., and Wolz, C. (2004) Regulatory and genomic plasticity of *Staphylococcus aureus* during persistent colonization and infection. *Int J Med Microbiol* 294: 195-202.

Gonzalez-Lamothe, R., Mitchell, G., Gattuso, M., Diarra, M. S., Malouin, F., and Bouarab, K. (2009) Plant antimicrobial agents and their effects on plant and human pathogens. *Int J Mol Sci* 10: 3400-3419.

Guillet, C., O. Join-Lambert, A. Le Monnier, A. Leclercq, F. Mecha M.-F. Mamzer-Bruneel, M. K. Bielecka, M. Scortti, O. Disson, P. Berche, J. Vazquez-Boland, O. Lortholary and M. Lecuit. 2010. Human Listeriosis Caused by *Listeria ivanovii*. Emerging Infectious Diseases, 16:136-138.

Harlid, R., Andersson, G., Frostell, C. G., Jorbeck, H. J., and Ortqvist, A. B. (1996) Respiratory tract colonization and infection in patients with chronic tracheostomy. A one-year study in patients living at home. *Am J Respir Crit. Care Med* 154: 124-129.

Hecht, D. W. (2006) Anaerobes: antibiotic resistance, clinical significance, and the role of susceptibility testing. *Anaerobe* 12: 115-121.

Harrison, F. (2007) Microbial ecology of the cystic fibrosis lung. *Microbiology* 153: 917-923.

Hoffman, L. R., Deziel, E., D'Argenio, D. A., Lepine, F., Emerson, J., McNamara, S., Gibson, R. L., Ramsey, B. W., and Miller, S. I. (2006) Selection for *Staphylococcus aureus* small-colony variants due to growth in the presence of *Pseudomonas aeruginosa*. *Proc Natl Acad Sci USA* 103: 19890-19895.

Jacques, M., Aragon, V., and Tremblay, Y. D. (2011) Biofilm formation in bacterial pathogens of veterinary importance. *Anim Health Res Rev* 11: 97-121.

Kessler, E., Safrin, M., Olson, J. C., and Ohman, D. E. (1993) Secreted LasA of *Pseudomonas aeruginosa* is a staphylolytic protease. *J Biol Chem* 268: 7503-7508.

Kloos, W. E., and Bannerman, T. L. (1994) Update on clinical significance of coagulase-negative *staphylococci*. *Clin Microbiol Rev* 7: 117-140.

Li, W.; Dang, Y.; Liu, J. O.; Yu, B. Expeditious synthesis of hippuristanol and congeners with potent antiproliferative activities. *Chemistry* 2009, 15, 10356-9.

Lightbown, J. W., and Jackson, F. L. (1956) Inhibition of cytochrome systems of heart muscle and certain bacteria by the antagonists of dihydrostreptomycin: 2-alkyl-4-hydroxyquinoline N-oxides. *Biochem J* 63: 130-137.

Lyczak, J. B., Cannon, C. L., and Pier, G. B. (2002) Lung infections associated with cystic fibrosis. *Clin Microbiol Rev* 15: 194-222.

Machan, Z. A., Taylor, G. W., Pitt, T. L., Cole, P. J., and Wilson, R. (1992) 2-Heptyl-4-hydroxyquinoline N-oxide, an antistaphylococcal agent produced by *Pseudomonas aeruginosa*. *J Antimicrob Chemother* 30: 615-623.

Malouin, F., E. Brouillette, A. Martinez, B. J. Boyll, J. L. Toth, J. L. Gage and N. E. Allen. 2005. Identification of antimicrobial compounds active against intracellular *Staphylococcus aureus*. FEMS Immunol. Med. Microbiol. 45:245-252.

Martin-Hernandez, A. M., Dufresne, M., Hugouvieux, V., Melton, R., and Osbourn, A. (2000) Effects of targeted replacement of the tomatinase gene on the interaction of *Septoria lycopersici* with tomato plants. *Mol Plant Microbe Interact* 13: 1301-1311.

Mates, S. M., L. Patel, H. R. Kaback, and M. H. Miller. 1983. Membrane potential in anaerobically growing *Staphylococcus aureus* and its relationship to gentamicin uptake. Antimicrob. Agents Chemother. 23:526-530.

Mead, P. S., Slutsker, L., Dietz, V., McCaig, L. F., Bresee, J. S., Shapiro, C., Griffin, P. M., and Tauxe, R. V. (1999) Food-related illness and death in the United States. *Emerg Infect Dis* 5: 607-625.

Melter, O., and Radojevic, B. (2010) Small colony variants of *Staphylococcus aureus*-review. *Folia Microbiol (Praha)* 55: 548-558.

Miller, M. H., Wexler, M. A., and Steigbigel, N. H. (1978) Single and combination antibiotic therapy of *Staphylococcus aureus* experimental endocarditis: emergence of gentamicin-resistant mutants. *Antimicrob Agents Chemother* 14: 336-343.

Mingyu, H., Lin, L., Hao, W., Ying, S., Peng-Yu. Y., Mahesh. U., Qing-Hua, X., and Shao, Q. Y. (2011) Multicolor, One- and Two-Photon Imaging of Enzymatic Activities in Live Cells with Fluorescently Quenched Activity-Based Probes (qABPs), JACS 133(31): 12009-12020.

Mitchell, G., Brouillette, E., Seguin, D. L., Asselin, A. E., Jacob, C. L., and Malouin, F. (2010a) A role for sigma factor B in the emergence of *Staphylococcus aureus* small-colony variants and elevated biofilm production resulting from an exposure to aminoglycosides. *Microb Pathog* 48: 18-27.

Mitchell, G., Seguin, D. L., Asselin, A. E., Deziel, E., Cantin, A. M., Frost, E. H., Michaud, S., and Malouin, F. (2010b) *Staphylococcus aureus* sigma B-dependent emergence of small-colony variants and biofilm production following exposure to *Pseudomonas aeruginosa* 4-hydroxy-2-heptylquinoline-N-oxide. *BMC Microbiol* 10: 33.

Mitchell, G., Bilodeau, G., Grondin, G., Cantin, A. and Malouin, F (2010c) Defects in the cystic fibrosis transmembrane conductance regulator (CFTR) increase *Staphylococcus aureus* intracellular infection of human pulmonary cells. Abstr. 100th Gen. Meet. Am. Soc. Microbiol., abstr. D-1179.

Mitchell, G., Gattuso, M., Bouarab, K. and Malouin, F (2009) Tomatidine (TO) affects virulence regulators of prototypical *Staphylococcus aureus* (SA) and small-colony variants (SCV) of cystic fibrosis patients. Abstr. 49th Intersci. Conf. *Antimicrob. Agents Chemother., abstr.* C1-1341.

Moisan, H., Brouillette, E., Jacob, C. L., Langlois-Begin, P., Michaud, S., and Malouin, F. (2006) Transcription of virulence factors in *Staphylococcus aureus* small-colony variants isolated from cystic fibrosis patients is influenced by SigB. *J Bacteriol* 188: 64-76.

Nagy, E. (2010) Anaerobic infections: update on treatment considerations. Drugs 70: 841-858. Osbourn, A. E. (1996) Preformed Antimicrobial Compounds and Plant Defense against Fungal Attack. Plant *Cell* 8: 1821-1831.

Palmer, M. L., Lee, S. Y., Maniak, P. J., Carlson, D., Fahrenkrug, S. C., and O'Grady, S. M. (2006) Protease-activated receptor regulation of Cl-secretion in Calu-3 cells requires prostaglandin release and CFTR activation. *Am J Physiol Cell Physiol* 290: C1189-1198.

Parkins, M. D., and Elborn, J. S. (2010) Newer antibacterial agents and their potential role in cystic fibrosis pulmonary exacerbation management. *J Antimicrob Chemother* 65: 1853-1861.

Peter G. M. Wuts & Theodora W. Greene editors, Protective groups in organic synthesis, 4th edition, Wiley 2007.

Proctor, R. A., von Eiff, C., Kahl, B. C., Becker, K., McNamara, P., Herrmann, M., and Peters, G. (2006) Small colony variants: a pathogenic form of bacteria that facilitates persistent and recurrent infections. *Nat Rev Microbiol* 4: 295-305.

Pyorala, S., and Taponen, S. (2009) Coagulase-negative *staphylococci*-emerging mastitis pathogens. *Vet Microbiol* 134: 3-8.

Qazi, S., Middleton, B., Muharram, S. H., Cockayne, A., Hill, P., O'Shea, P., Chhabra, S. R., Camara, M., and Williams, P. (2006) N-acylhomoserine lactones antagonize virulence gene expression and quorum sensing in *Staphylococcus aureus*. *Infect Immun* 74: 910-919.

Ragle, B. E., Karginov, V. A., and Bubeck Wardenburg, J. (2010) Prevention and treatment of *Staphylococcus aureus* pneumonia with a beta-cyclodextrin derivative. *Antimicrob Agents Chemother* 54, 298-304

Roddick, J. G. (1974) Steroidal glycoalkaloid alpha-tomatine. *Phytochemistry* 13: 9-25.

Ruiz-Rubio, M., Perez-Espinosa, A., Lairini, K., Roldan-Arjona, T., Dipietro, A., and Anaya, N. (2001) Metabolism of the tomato saponin alpha-tomatine by phytopathogenic fungi. In *Studies in Natural Products Chemistry. Vol. 25.* Rahman, A. (ed). Oxford: Elsevier, pp. 293-326.

Rupnik, M., Wilcox, M. H., and Gerding, D. N. (2009) *Clostridium difficile* infection: new developments in epidemiology and pathogenesis. *Nat Rev Microbiol* 7: 526-536.

Sears, P. M., and McCarthy, K. K. (2003) Management and treatment of staphylococcal mastitis. *Vet Clin North Am Food Anim Pract* 19: 171-185, vii.

Sears, P. M. and K. K. McCarthy (2003) Management and treatment of staphylococcal mastitis. Vet. Clin. Food Anim. Pract. 19:171-185.

Sendi, P., and Proctor, R. A. (2009) *Staphylococcus aureus* as an intracellular pathogen: the role of small colony variants. *Trends Microbiol* 17: 54-58.

Shah, P. M. (2005) The need for new therapeutic agents: what is the pipeline? *Clin Microbiol Infect* 11 Suppl 3: 36-42.

Sibley, C. D., Parkins, M. D., Rabin, H. R., and Surette, M. G. (2009) The relevance of the polymicrobial nature of airway infection in the acute and chronic management of patients with cystic fibrosis. *Curr Opin Investig Drugs* 10: 787-794.

Sibley, C. D., and Surette, M. G. (2011) The polymicrobial nature of airway infections in cystic fibrosis: Cangene Gold Medal Lecture. *Can J Microbiol* 57: 69-77.

Simons, V., Morrissey, J. P., Latijnhouwers, M., Csukai, M., Cleaver, A., Yarrow, C., and Osbourn, A. (2006) Dual effects of plant steroidal alkaloids on *Saccharomyces cerevisiae*. *Antimicrob Agents Chemother* 50: 2732-2740.

Schmitz, F.-J., A. C. Fluit, M. Gondolf, R. Beyrau, E. Lindenlauf, J. Verhoef, H.-P. Heinz and M. E. Jones. 1999. The prevalence of aminoglycoside resistance and corresponding resistance genes in clinical isolates of *staphylococci* from 19 European hospitals. J. Antimicrob. Chemother. 43: 253-259

Songer, J. G. (2010) Clostridia as agents of zoonotic disease. *Vet Microbiol* 140: 399-404.

Songer, J. G., and F. A. Uzal. 2005. Clostridial enteric infections in pigs. J. Vet. Diagn. Invest. 17:528-536.

Stepan, J., Pantucek, R., and Doskar, J. (2004) Molecular diagnostics of clinically important *staphylococci*. *Folia Microbiol (Praha)* 49: 353-386.

Stewart, P. S. (2002) Mechanisms of antibiotic resistance in bacterial biofilms. *Int J Med Microbiol* 292: 107-113

Talbot, G. H., Bradley, J., Edwards, J. E., Jr., Gilbert, D., Scheld, M., and Bartlett, J. G. (2006) Bad bugs need drugs: an update on the development pipeline from the Antimicrobial Availability Task Force of the Infectious Diseases Society of America. *Clin Infect Dis* 42: 657-668.

Tenhagen, B. A., G. Koster, et al. (2006). "Prevalence of mastitis pathogens and their resistance against antimicrobial agents in dairy cows in Brandenburg, Germany." J Dairy Sci 89(7): 2542-51.

Tuchscherr, L., Medina, E., Hussain, M., Volker, W., Heitmann, V., Niemann, S., Holzinger, D., Roth, J., Proctor, R. A., Becker, K., Peters, G., and Loffler, B. (2011) *Staphylococcus aureus* phenotype switching: an effective bacterial strategy to escape host immune response and establish a chronic infection. *EMBO Mol Med* (in press).

Van Immerseel, F., J. De Buck, F. Pasmans, G. Huyghebaert, F. Haesebrouck, and R. Ducatelle. 2004. *Clostridium perfringens* in poultry: an emerging threat for animal and public health. *Avian Pathol.* 33:537-549.

Vergison, A., O. Denis, A. Deplano, G. Casimir, G. Claeys, F. DeBaets, K. DeBoeck, N. Douat, H. Franckx, J. Gigi, M. leven, C. Knoop, P. Lebeque, F. Lebrun, A. Malfroot, F. Paucquay, D. Pierard, J. Van Eldere and M. J. Struelens. 2007. National survey of molecular epidemiology of *Staphylococcus aureus* colonization in Belgian cystic fibrosis patients. *J. of Antimicrob Chemother.* 59:893-899.

Vial, L., Lepine, F., Milot, S., Groleau, M. C., Dekimpe, V., Woods, D. E., and Deziel, E. (2008) *Burkholderia pseudomallei, B. thailandensis*, and *B. ambifaria* produce 4-hydroxy-2-alkylquinoline analogues with a methyl group at the 3 position that is required for quorum-sensing regulation. J Bacteriol 190: 5339-5352.

Voggu, L., Schlag, S., Biswas, R., Rosenstein, R., Rausch, C., and Gotz, F. (2006) Microevolution of cytochrome bd oxidase in *Staphylococci* and its implication in resistance to respiratory toxins released by *Pseudomonas*. *J Bacteriol* 188: 8079-8086.

Vuong, C., and Otto, M. (2002) *Staphylococcus epidermidis* infections. *Microbes Infect* 4: 481-489.

Wellinghausen, N., Chatterjee, I., Berger, A., Niederfuehr, A., Proctor, R. A., and Kahl, B. C. (2009) Characterization of clinical *Enterococcus faecalis* small-colony variants. *J Clin Microbiol* 47: 2802-2811.

Wilson, S. G., and Sanders, C. C. (1976) Selection and characterization of strains of *Staphylococcus aureus* displaying unusual resistance to aminoglycosides. *Antimicrob Agents Chemother* 10: 519-525.

Witte, W., Cuny, C., Klare, I., Nubel, U., Strommenger, B., and Werner, G. (2008) Emergence and spread of antibiotic-resistant Gram-positive bacterial pathogens. *Int J Med Microbiol* 298: 365-377.

Wong, W. C. G., C. *Synthesis* 1995, 139.

The invention claimed is:

1. A method of preventing or treating an infection caused by a bacterial pathogen of the Firmicutes phylum in a subject, said method comprising administering to said subject a therapeutically effective amount of a compound or a composition comprising the compound and a pharmaceutically acceptable carrier, in combination with an aminoglycoside antibiotic, the compound being;

(i) a compound of formula:

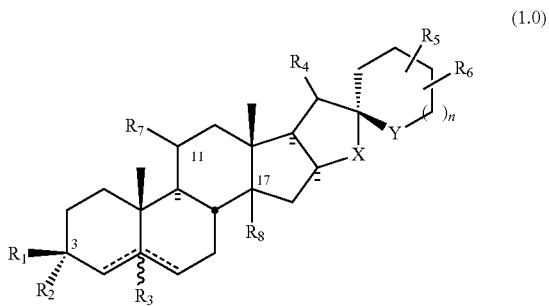

(1.0)

wherein, (1) R1 is H, OH, $NH_2$, NHR12, N(R12)(R12'), OR12 or SR12; and R2=H; or
(2) R2 is H, OH, $NH_2$, NHR12, N(R12)(R12'), OR12 or SR12; and R1=H; or
(3) R1 and R2 together form =O or =NR12;
R3 is α-H, β-H, α-alkyl, β-alkyl, α-OH or β-OH, or is absent when the double bond is present either in C4=C5, or in C5=C6;
- - - - - is an optional double bond;
R4-R6 are identical or different and are H, alkyl, OH, OR18, NHR18 or N(R18)(R18');
R7 is H, α-OH or β-OH;
R8 is α-H, α-OH or β-OH;
X and Y are identical or different and are O, NR19, or $CH_2$;
R12 and R12' are identical or different and are H, alkyl, aryl, COalkyl, COaryl, $CO_2$alkyl, $CO_2$aryl, CONHalkyl, CONHaryl, $SO_3H$, $SO_2$alkyl, $SO_2$aryl, $SO_2N(R14)_p$, $PO_3H_2$, CO—CH(R20)$NH_2$, $(CH_2)_n$—NH—R14, C(=NH)NHR21, $CH_3OCH_2$, Silylalkyl, $(CH_2)_mCO_2H$, $(CH_2)_mSO_3H$, $(CH_2)_mNH_2$, $(CH_2)_mNHC(=NH)NH_2$, $(CH_2)_m$—C(=NH)$NH_2$, NHalkyl or NHaryl;
R14, R22 and R22' are identical or different and are H, alkyl, aryl, COalkyl, $CO_2$alkyl, COaryl, $CO_2$aryl, $SO_2$alkyl, $SO_2$aryl, $SO_2N(alkyl)p'$ or CO—CH(R20)$NH_2$;
R18 and R18' are identical or different and are H, alkyl, aryl, COalkyl, COaryl, CONHalkyl, CONHaryl, $SO_3H$, $SO_2$alkyl, $SO_2$aryl, $SO_2N(alkyl)_{p''}$, $PO_3H_2$, CO—CH(R20')$NH_2$, $(CH_2)_{n''}$—NH—R22, C(=NH)NHR21',
$(CH_2)_mCO_2H$, $(CH_2)_mSO_3H$, $(CH_2)_mNH_2$, $(CH_2)_mNHC(=NH)NH_2$, $(CH_2)_{m'}$—C(=NH)$NH_2$, NHalkyl or NHaryl;
R19 is H, alkyl, aryl, COH, COalkyl, COaryl, $CO_2$alkyl, $CO_2$aryl, CONHalkyl, CONHaryl, $SO_3H$, $SO_2$alkyl, $SO_2$aryl, $SO_2N(Ralkyl)_{p'''}$, $PO_3H_2$, CO—CH(R20")$NH_2$, $(CH_2)_{n'''}$—NH—R22', C(=NH)NHR21",
$(CH_2)_{m''}CO_2H$, $(CH_2)_{m''}SO_3H$, $(CH_2)_{m''}NH_2$, $(CH_2)_{m''}NHC(=NH)NH_2$, $(CH_2)_{m'''}$—C(=NH)$NH_2$, NHalkyl or NHaryl;
R20, R20' and R20" are identical or different and correspond to the side chain of any L- and D- amino acid;
R21, R21' and R21" are identical or different and are H, alkyl, OH, Oalkyl, Oaryl, NHalkyl, NHaryl, $N(alkyl)_2$, $N(aryl)_2$, or N(alkyl)(aryl);
n, n', n" and n''' are identical or different and are 0-5;
m, m' and m" are identical or different and are 1-5; and
p, p', p" and p''' are identical or different and are 1-2;
or a salt, stereoisomer or any mixture of stereoisomers of the compound of formula 1.0,
whereby said bacterial infection is prevented or treated.

2. A method of disinfecting and/or sterilizing an object of a Firmicutes phylum bacterium, said method comprising applying an effective amount of the compound as defined in claim 1 or of a composition comprising said compound, and an aminoglycoside antibiotic, to said object, whereby said object is disinfected and/or sterilized.

3. The method of claim 2, wherein said object is an animal, an animal tissue, animal cells, food, a synthetic material or a natural material.

4. The method of claim 1, wherein the *Firmicutes phylum* is a *staphylococcus*.

5. The method of claim 4, wherein the *staphylococcus* is an antibiotic-resistant *Staphylococcus*.

6. The method of claim 4, wherein the *staphylococcus* is a *Staphylococcus aureus*, a *Staphylococcus epidermidis*, a *Staphylococcus haemolyticus*, a *Staphylococcus saprophyticus*, or a *Staphylococcus hominis*.

7. The method of claim 6, wherein the *staphylococcus* is a *Staphylococcus aureus*.

8. The method of claim 7, wherein said *staphylococcus* is a methicillin-resistant *Staphylococcus aureus* (MRSA), community acquired MRSA, a vancomycin-intermediate *Staphylococcus aureus* (VISA), a vancomycin-resistant *Staphylococcus aureus* (VRSA) or a glycopeptide-resistant *Staphylococcus aureus* (GISA).

9. The method of claim 1, wherein the infection is a polymicrobial infection further involving at least one microorganism that produces at least one electron transport inhibitor including *Pseudomonas aeruginosa*.

10. The method of claim 1, wherein the subject has cystic fibrosis.

11. The method of claim 1, wherein the subject has a polymicrobic hospital-acquired pneumonia or a polymicrobic infection associated with a burn, a catheter, or an endotracheal tube.

12. The method of claim 1, wherein the aminoglycoside antibiotic is amikacin, gentamicin, kanamycin, streptomycin or tobramycin.

13. The method of claim 1, further comprising a beta-lactam antibiotic.

14. The method of claim 1, wherein said subject or object is food, a cow or a human.

15. A kit comprising the compound as defined in claim 1, an aminoglycoside antimicrobial agent, and instructions to use same in (a) the prevention or treatment of a microbial infection; or (b) the disinfection, sterilization and/or antisepsis of an object.

16. The kit of claim 15, wherein the aminoglycoside antibiotic is amikacin, gentamicin, kanamycin, streptomycin or tobramycin.

17. The kit of claim 15, further comprising a beta-lactam antibiotic.

18. The method of claim 1, wherein the compound is of formula 1.0 and wherein
(i) R1 is OR12 or H;
(ii) R2 is OR12 or H;
(iii) R3 is H;
(iv) R4 is an alkyl;
(v) R5 is H;
(vi) R6 is an alkyl;
(vii) R7 is H;
(ix) R8 is H;
(x) n is 1;
(xi) X is O;
(xii) Y is NR19;
(xiii) there is no double bond; or
(xiv) any combination of (i) to (xiii).

19. The method of claim 1, wherein the compound is of formula 1.0 and wherein:
(i) R1 is OR12 and R2 is H;
(ii) R3 is H;
(iii) R4 is CH3;
(iv) R5 is H;
(v) R6 is CH3;
(vi) R7 is H;
(vii) R8 is H;
(viii) n is 1;
(ix) X is O;
(x) Y is NR19;
(xi) there is no double bond; or
(xii) any combination of (i) to (xi).

20. The method of claim 1, wherein the compound is of formula 1.0 and wherein R3 is H, R4 is alkyl, R5 is H, R6 is alkyl, R7 is H, R8 is H, n is 1, X is O, Y is NR19 or N$^+$R(19)(R19') and there is no double bond.

21. The method of claim 20, wherein Y is NR19.

22. The method of claim 21, wherein (a) R1 is H, R2 is OR12, R4 is CH$_3$ and R6 is CH$_3$; or (b) R1 is OR12, R2 is H, R4 is CH$_3$ and R6 is CH$_3$; or (c) R1 is NH2 and R2 is H or R1 is H and R2 is NH2, R4 is CH$_3$, R6 is CH$_3$, and R19 is H.

23. The method of claim 22 (b), wherein (i) R12 is SO$_3$H and R19 is H; or (ii) R12 is PO$_3$H$_2$ and R19 is H; or (iii) R12 is (CH$_2$)$_m$—CO$_2$H, m is 1 and R19 is H; or (iv) R12 is (CH$_2$)$_m$NH$_2$, m is 2 and R19 is H; or (v) R12 is alkyl, and R19 is H; or (vi) R12 is (CH$_2$)$_m$NHC(=NH)NH$_2$, m is 2 and R19 is H; or (vii) R12 is H and R19 is COH; or (viii) R12 is an alkyl and R19 is COH.

24. The method of claim 22 (a), wherein (i) R12 is a CH$_3$OCH$_2$ and R19 is H; or (ii) R12 is COalkyl, and R19 is COH.

25. The method of claim 24 (ii), wherein COalkyl is COCH$_3$.

26. The method of claim 22, wherein the compound is a methanesulfonate salt of the compound as defined in claim 22 (a), wherein R12 is H and R19 is H.

27. The method of claim 22, wherein the compound is a citrate salt of a compound as defined in claim 22 (a), wherein R12 is H and R19 is H.

28. The method of claim 21, wherein (i) R1 and R2 together form =O, R4 is CH$_3$, R6 is CH$_3$ and R19 is (C=O)H; or (ii) R1 and R2 together form =O, R4 is CH$_3$, R6 is CH$_3$ and R19 is H.

29. The method of claim 23 (viii), wherein the alkyl is —CH$_2$—CH=CH$_2$.

30. The method of claim 23 (v), wherein the alkyl is —CH$_2$—CH=CH$_2$.

31. The method of claim 1, wherein the compound is of formula 1.1:

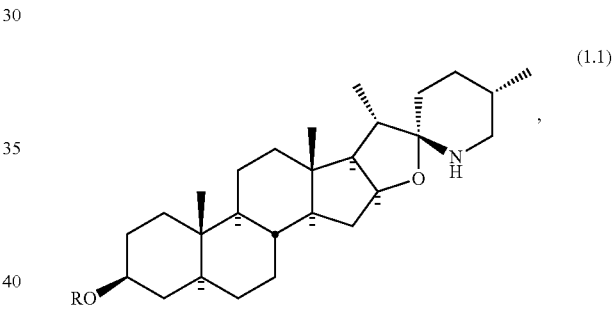

(1.1)

wherein R is defined as R12 in claim 1.

32. The method of claim 1, wherein the Firmicutes Phylum bacteria is a Bacillales.

* * * * *